US012762702B2

(12) United States Patent
Attili et al.

(10) Patent No.: US 12,762,702 B2
(45) Date of Patent: Oct. 13, 2026

(54) COMPREHENSIVE HEALTH ASSESSMENT SYSTEM DRIVEN BY AI POWERED BREAST IMAGES ANALYSIS

(71) Applicant: COGNITIVECARE INC., Milpitas, CA (US)

(72) Inventors: Suresh Venkata Satya Attili, Hyderabad (IN); Naresh Nelaturi, Guntur (IN); Venkata Narasimham Peri, Plano, TX (US); Manoj Ramesh Teltumbade, Pittsburgh, PA (US); Sheena Gill, Centreville, VA (US)

(73) Assignee: COGNITIVECARE INC

( * ) Notice: Subject to any disclaimer, the term of this patent is extended or adjusted under 35 U.S.C. 154(b) by 126 days.

(21) Appl. No.: 18/820,726

(22) Filed: Aug. 30, 2024

(65) Prior Publication Data

US 2026/0044953 A1 Feb. 12, 2026

Related U.S. Application Data

(60) Provisional application No. 63/681,897, filed on Aug. 12, 2024.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4312* (2013.01); *A61B 5/7275* (2013.01);
(Continued)

(58) Field of Classification Search
CPC ......... G06T 7/0012; G06T 2207/20081; G06T 2207/20084; G06T 2207/30068;
(Continued)

(56) References Cited

U.S. PATENT DOCUMENTS

| | | | | |
|---|---|---|---|---|
| 2018/0075628 | A1 * | 3/2018 | Teare | G06V 10/82 |
| 2022/0044762 | A1 * | 2/2022 | Van Der Baan | G16H 50/20 |
| 2024/0127431 | A1 * | 4/2024 | Park | G06N 3/04 |

OTHER PUBLICATIONS

Tsai, Hsin-Tien, et al. "Multi-gene signature of microcalcification and risk prediction among Taiwanese breast cancer." Scientific Reports 10.1 (2020): 18276. (Year: 2020).*

* cited by examiner

*Primary Examiner* — Andrew M Moyer
(74) *Attorney, Agent, or Firm* — Davé Law Group, LLC; Raj S. Davé

(57) ABSTRACT

According to an embodiment, disclosed is a system comprising a processor configured to receive an image of a breast of a patient and patient data comprising genetic data; extract features from the image and the patient data, using one or more machine learning models, wherein the features comprise a presence of a calcification and a calcification pattern to generate a breast calcification vector; augment the breast calcification vector with the genetic data; determine, using the machine learning models, a first risk for a breast cancer; a second risk to one or more organs of the patient, wherein the organs comprises one or more of heart, kidney, lungs, pancreas, and brain; predict, a third risk based on one or more of a healing response, a tumor flow and growth, inflammation and degeneration, a disease relapse, an adverse event, and a clinical response; and determine, an overall risk to the patient.

20 Claims, 31 Drawing Sheets

(51) Int. Cl.
*G06V 10/764* (2022.01)
*G06V 10/77* (2022.01)
*G16H 50/20* (2018.01)
*G16H 50/30* (2018.01)

(52) U.S. Cl.
CPC ........ *G06V 10/764* (2022.01); *G06V 10/7715* (2022.01); *G16H 50/20* (2018.01); *G16H 50/30* (2018.01); *G06T 2207/20081* (2013.01); *G06T 2207/20084* (2013.01); *G06T 2207/30068* (2013.01); *G06T 2207/30096* (2013.01); *G06V 2201/031* (2022.01)

(58) Field of Classification Search
CPC ........ G06T 2207/30096; A61B 5/4312; A61B 5/7275; G06V 10/764; G06V 10/7715; G06V 2201/031; G16H 50/20; G16H 50/30; G16H 30/40; G16H 50/70
See application file for complete search history.

| Info. L1 | Info. L2 | Info. L 3 | Info. L4 | Info. L5 | Sub score range (0 to 1) & Stratification | Assessment & management of | Score | Score | Ground Truth (clinical fact validation) |
|---|---|---|---|---|---|---|---|---|---|
| Consortium of Image analysis DL Models: for Identification/ quantification of Mammograms for Location, Spread, Nature, Shape, Size, Density, Anatomy, Distribution, Involvement, Continuity, Etiologic, Characterization | Outcome of the ML Model 1: Quantified Calcification Vector with Elements (scores) Location, Spread, Nature, Shape, Size, Density, Anatomy, Distribution, Involvement, Continuity, Etiologic, Characterization | Embedding Calcification vector information is Augmented with Genetics, Clinical, Medical, Labs in the ML Model 2 and estimating score BICV | Consortium of Assessment ML Models: Generates 16 outcomes, with one outcome from each model | Leveraging statistical models for computation of BIC – V & BIC – BStatistical models to compute BRIC C-G | BICV Cardiovascular | Cardiovascular | **BIC-V** | Comprehensive score: **BRIC-G** | Cardiac-specific imaging like ECHO, MRI, CT angiograms, and Holter test results. |
| | | | | | Cardiac contractile | | | | |
| | | | | | Cardiac Rhythm | | | | |
| | | | | | Renovascular & Renal Perfusion | Kidneys and the blood vessels | | | Renal function tests, renal Doppler, and angiography |
| | | | | | Retinopathy | Retina | | | Retinal evaluations and neuroimaging (MRI of the brain) |
| | | | | | Pancreatic | Pancreatic Diseases/Cancer | | | Imaging of the pancreas (ERCP, MRCP, MRI/CT scans) |
| | | | | | Cerebrovascular and CNS | Neurological and Cerebrovascular health | | | Brain imaging (MRI, EEG, MMS) for neurological assessment |
| | | | | | Pulmonary/COPD | Lung function and COPD | | | Pulmonary imaging (CT chest), and functional tests (DLCO) |
| | | | | | Chronic Disease | Chronic Disease | | | clinical evaluation for subsequent development of chronic disease conditions |
| | | | | | Critical Vascular Perfusion (Low/Medium/High) | Vascular system's ability to deliver adequate Blood Flow to various organs and tissues | | | organ specific serum markers and imaging- ex- bone/muscle etc |
| | | | | | Healing | Organ Biology | **BIC-B** | | Healing Time |
| | | | | | Tumor Flow and Growth | | | | Ki-67 index/Grade/ Vascularity/LVI/PNI and morphology |
| | | | | | Inflammation/Degeneration | | | | Development or association with arthritis, inflammatory bowel disease, RA, SLE, auto immune disorders Chronic inflammation etc |
| | | | | | Relapse | | | | overall survival/ progression free survival/ tumour free period / |
| | | | | | Adverse Events | | | | QOL score/ TWISTT score/ CTC AE incidence and prevalence |
| | | | | | Clinical Response | | | | PET CT/ RECIST criteria/ Serum markers/ Clinical Improvement/Pathological response etc |

FIG. 2

| NO. | SUB SCORE BIC V | GENETIC MARKERS INPUT |
|---|---|---|
| 1 | Cardiovascular | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |
| 2 | Cardiac Contractile | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |
| 3 | Cardiac Rhythm | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |
| 4 | Renovascular & Renal Perfusion | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |
| 5 | Retinopathy | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |
| 6 | Pancreatic | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |
| 7 | Cerebrovascular & CNS | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |
| 8 | Pulmonary/COPD | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |
| 9 | Chronic Disease | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |
| 10 | Critical Vascular Perfusion | APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1 |

FIG. 21A

| NO. | SUB SCORE BIC B | GENETIC MARKERS INPUT |
|---|---|---|
| 11 | Healing | BRCA 1& 2, PTEN, PALB 2, TP53, ATM, RB, CDH1&2CHECK2/ NF1NBN / STK11/ MSI/BARD/ BRIPRAD/ POLE |
| 12 | Tumor Flow and Growth | BRCA 1& 2, PTEN, PALB 2, TP53, ATM, RB, CDH1&2CHECK2/ NF1NBN / STK11/ MSI/BARD/ BRIPRAD/ POLE |
| 13 | Relapse | BRCA 1& 2, PTEN, PALB 2, TP53, ATM, RB, CDH1&2CHECK2/ NF1NBN/ STK11/MSI/BARD/ BRIPRAD/ POLE |
| 14 | Adverse Events | BRCA 1& 2, PTEN, PALB 2, TP53, ATM, RB, CDH1&2CHECK2/ NF1NBN/ STK11/MSI/BARD/ BRIPRAD/ POLE |
| 15 | Clinical Response | BRCA 1& 2, PTEN, PALB 2, TP53, ATM, RB, CDH1&2CHECK2/ NF1NBN/ STK11/MSI/BARD/ BRIPRAD/ POLE |
| 16 | Inflammation / Degeneration | TNF/ IL6&1beta/ MMP3,COL2A1, APOE /PSEN1SNAK/ PARKIN/ HLA/ NOD2 |

FIG. 21B

| NO. | SUB SCORE BIC V | CLINICAL AND LABS |
|---|---|---|
| 1 | Cardiovascular | • Vitals/BMI/Family Hist/past CAD/CVD NASH/ retinopathy<br>• Hb/NLR/NPR/CRP/Lipid profile/APO LipoA&B/ESR/ CPK/S Create/ ALT,AST ratio/S K,CA,Na/ Trop levels/ BNPs |
| 2 | Cardiac Contractile | • Vitals/BMI/Family Hist/past CAD/CVD NASH/retinopathy/6 Min walk test<br>• Hb/NLR/NPR/CRP/Lipid profile/APO LipoA&B/ESR/ CPK/S Create/ ALT,AST ratio/S K,CA,Na/ Trop levels/ BNPs/ TMT/ |
| 3 | Cardiac Rhythm | • Vitals/BMI/Family Hist/past CAD/CVD NASH/ retinopathy<br>• Hb/NLR/NPR/CRP/Lipid profile/APO LipoA&B/ESR/ CPK/S Create/ ALT,AST ratio/S K,CA,Na/ Trop levels/ BNPs |
| 4 | Renovascular & Renal Perfusion | • Vitals/BMI/Family Hist/past CAD/CVD NASH/ retinopathy/edema/U output/mental status/skin changes<br>• Hb/NLR/NPR/CRP/Lipid profile/ESR/ Urea/ Uric acid/S Create/ S K,CA,Na/ BNPs/ CUE/ 24 Hr urine protein/ Protein Create ratio/EPO/VMA/ CAtahola |
| 5 | Retinopathy | • Vitals/BMI/Family Hist/past CAD/CVD NASH<br>• Hb/NLR/NPR/CRP/Lipid profile/APO LipoA&B/ESR/ CPK/S Create/ HbA1C/ Bilirubin |
| 6 | Pancreatic | • Vitals/BMI/Family Hist/past CAD/CVD NASH/ Abdominal findings/ food habits<br>• Hb/NLR/NPR/CRP/Lipid profile/APO LipoA&B/ESR/ Amylase/ Lipase/CA 19.9/S Create/ ALT,AST ratio/S Bilirubin |
| 7 | Cerebrovascular & CNS | • Vitals/BMI/Family Hist/past CAD/CVD NASH/ retinopathy/seizures/Stroke/neuropathy<br>• Hb/NLR/NPR/CRP/Lipid profile/APO LipoA&B/ESR/ CPK/S Create/ ALT,AST ratio/S K,CA,Na/ Trop levels/ BNPs |
| 8 | Pulmonary/COPD | • Vitals/BMI/Family Hist/past CAD/CVD NASH/ retinopathy<br>• Hb/NLR/NPR/CRP/Lipid profile/APO LipoA&B/ESR/ CPK/S Create/ ALT,AST ratio/S K,CA,Na/ Trop levels/ BNPs |
| 9 | Chronic Disease | • Vitals/BMI/Family Hist/past CAD/CVD NASH/ retinopathy<br>• Hb/NLR/NPR/CRP/Lipid profile/APO LipoA&B/ESR/ CPK/S Create/ ALT,AST ratio/S K,CA,Na/ Trop levels/ BNPs |
| 10 | Critical Vascular Perfusion | • Vitals/BMI/Family Hist/past CAD/CVD NASH/ retinopathy<br>• Hb/NLR/NPR/CRP/Lipid profile/APO LipoA&B/ESR/ CPK/S Create/ ALT,AST ratio/S K,CA,Na/ Trop levels/ BNPs |

FIG. 22A

| NO. | SUB SCORE BIC B | CLINICAL AND LABS |
|---|---|---|
| 11 | Healing | • Vitals/BMI/Family Hist/past CAD/CVD NASH/ retinopathy/cancer treatment<br>• CEA/ CA19.9/ CA15.3/ CA125/ PSA/Estradiol/ CBC RFT/LFT/TFT/ Lipid |
| 12 | Tumor Flow and Growth | • Vitals/BMI/Family Hist/past CAD/CVD NASH/ retinopathy/cancer treatment<br>• CEA/ CA19.9/ CA15.3/ CA125/ PSA/Estradiol/ CBC RFT/LFT/TFT/ Lipid |
| 13 | Relapse | • Vitals/BMI/Family Hist/past CAD/CVD NASH/ retinopathy/cancer treatment<br>• CEA/ CA19.9/ CA15.3/ CA125/ PSA/Estradiol/ CBC RFT/LFT/TFT/ Lipid |
| 14 | Adverse Events | • Vitals/BMI/Family Hist/past CAD/CVD NASH/ retinopathy/cancer treatment<br>• CEA/ CA19.9/ CA15.3/ CA125/ PSA/Estradiol/ CBC RFT/LFT/TFT/ Lipid |
| 15 | Clinical Response | • Vitals/BMI/Family Hist/past CAD/CVD NASH/ retinopathy/cancer treatment<br>• CEA/ CA19.9/ CA15.3/ CA125/ PSA/Estradiol/ CBC RFT/LFT/TFT/ Lipid |
| 16 | Inflammation / Degeneration | • Vitals/BMI/Family Hist/past CAD/CVD NASH/ retinopathy/cancer treatment/ Joint pains/ Osteopenia<br>• CRP/TNF/IL6/ESR/Inflammation markers/ RFT/LFT/TFT/ NLR/ NPR/Hb/MCV |

FIG. 22B

COMPREHENSIVE HEALTH ASSESSMENT SYSTEM DRIVEN BY AI POWERED BREAST IMAGES ANALYSIS

CROSS-REFERENCE TO RELATED APPLICATIONS

This application claims the benefit under 35 U.S.C § 119 of U.S. Provisional Application No. 63/681,897, filed on Aug. 12, 2024, which is hereby incorporated by reference in its entirety.

FIELD OF INVENTION

This application pertains generally to detecting and quantifying cancer risk and related risks to other organs. More particularly, it pertains to artificial intelligence (AI)/machine learning (ML) models, trained with patient data, for identifying patients with an increased risk for developing cancer/risk and the type of cancer/risk to any other organ given patient data.

BACKGROUND

In this section Prior Art is quoted.

"Cardiovascular disease (CVD) is a leading cause of death for women among non-communicable diseases worldwide. Although women are typically underserved in screening for cardiovascular-related disease. A large proportion of cardiovascular events occur in women whose 10-year estimated risk of CVD is low, and thus guidelines would not routinely recommend therapy. Thus, alternative, and complimentary methods of risk estimation are needed to identify women who might benefit from therapy." [U.S. patent Ser. No. 11/246,550B2, titled, "Method for detection and quantification of arterial calcification"].

"Cancer detection poses significant technical challenges as compared to detecting viral or bacterial infections since cancer cells, unlike viruses and bacteria, are biologically similar to and hard to distinguish from normal, healthy cells. For this reason, tests used for the early detection of cancer often suffer from higher numbers of false positives and false negatives than comparable tests for viral or bacterial infections or for tests that measure genetic, enzymatic, or hormonal abnormalities. This often causes confusion among healthcare practitioners and their patients leading in some cases to unnecessary, expensive, and invasive follow-up testing while in other cases to a complete disregard for follow-up testing resulting in cancers being detected too late for useful intervention. Physicians and patients' welcome tests that yield a binary decision or result, e.g., either the patient is positive or negative for a condition, such as observed in the over the counter pregnancy test kits which present, for example, an immunoassay result in the shape of a plus sign or a negative sign as an indication of pregnancy or not. However, unless the sensitivity and specificity of diagnosis approaches 99%, a level not obtainable for most cancer tests, such binary outputs can be highly misleading or inaccurate" [US Patent Application Publication, US20200005901A1, titled, "Cancer classifier models, machine learning systems and methods of use"].

Therefore, there is a need for a system and a method to determine risk assessment to other organs given a cancer is detected enabling physicians to provide a comprehensive assessment of the overall health of the patient.

SUMMARY

The following presents a summary to provide a basic understanding of one or more embodiments described herein. This summary is not intended to identify key or critical elements or delineate any scope of the different embodiments and/or any scope of the claims. The sole purpose of the summary is to present some concepts in a simplified form as a prelude to the more detailed description presented herein.

According to an embodiment, disclosed is a system comprising a processor executing one or more machine learning models; wherein the processor storing instructions in a non-transitory memory that, when executed, cause the processor to receive a first input comprising an image of a breast of a patient; receive a second input comprising a patient data, wherein the patient data comprises genetic data of the patient; extract features from the image and the patient data, using the machine learning models, wherein the features comprise a presence of a calcification and a calcification pattern to generate a breast calcification vector; augment the breast calcification vector with the genetic data to generate a feature vector; determine, using the machine learning models, a first output comprising a first risk for a breast cancer; determine, using the machine learning models, a second output comprising a second risk to one or more organs of the patient, wherein the organs comprises one or more of heart, kidney, lungs, pancreas, and brain; predict, using the machine learning models, a third output comprising a third risk based on one or more of a healing response, a tumor flow and growth, inflammation and degeneration, a disease relapse, an adverse event, and a clinical response of the patient; and determine, using a statistical model, a fourth output comprising an overall risk to the patient based on the first risk, the second risk, and the third risk; wherein the machine learning models are pre-trained, wherein pre-training comprises training the machine learning models using training data from plurality of patients, wherein the training data corresponding to each patient from the plurality of patients comprises one or more of breast images, chest images, organ images, genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

According to an embodiment of the system, the image comprises one or more of mammogram image, ultrasound image, computed tomography image, and magnetic resonance image.

According to an embodiment of the system, the system comprises a deep learning model for image analysis and for extracting of the features from the image.

According to an embodiment of the system, the system comprises a preprocessing module configured to normalize quality of the image across different imaging modalities.

According to an embodiment of the system, the system comprises a feature extraction module configured to extract the features from pre-processed data obtained from the image.

According to an embodiment of the system, the features comprises one or more of a ratio of fat to fiber, connective tissue density, and echogenicity of lumps.

According to an embodiment of the system, the system is configured to classify a breast tissue from the image into one of several predefined categories based on the features.

According to an embodiment of the system, the fourth output is a quantified score as Breast Risk Indicator for Calcification and Cancer-General (BRICC-G) score.

According to an embodiment of the system, the presence of the calcification is identified via a calcification detection module.

According to an embodiment of the system, the calcification detection module is further configured to identify and classify a type of calcification as one of ductile, vascular, and parenchymal calcification.

According to an embodiment of the system, the calcification detection module is further configured to quantify the calcification to provide an assessment of reversibility.

According to an embodiment of the system, the calcification pattern comprises one of more modules comprising deep learning models to determine one or more of a location, a spread, a nature, a size, a shape, a density, an anatomy, a distribution, an involvement, a continuity, an etiologic, and a characterization of breast arterial calcifications.

According to an embodiment of the system, the system further comprises a spread detection module configured to detect the spread of abnormalities within the image and determine a quantifying measure by generating a spread index representing an extent of each abnormality of the abnormalities.

According to an embodiment of the system, the system further comprises a malignant detection module configured to detect the nature of the calcification pattern, wherein the nature is one of a benign and a malignant; and wherein the nature of the calcification pattern is detected based on the features extracted from textural and morphological data; and wherein the nature of the calcification pattern is classified as one of normality and abnormality.

According to an embodiment of the system, the system further comprises a size characterization module, wherein the size characterization module is configured to calculate the size, comprising a dimension and outputting the dimension, of the calcification.

According to an embodiment of the system, the system further comprises a shape detection module configured to determine geometric properties that define the shape of abnormalities; and quantify characteristics of the shape of the calcification.

According to an embodiment of the system, the system further comprises a tissue density prediction module for density levels of tissue configured to determine the density by processing the image to evaluate the density of a tissue and determine levels of the density.

According to an embodiment of the system, the system further comprises an anatomy prediction module configured for mapping anatomical features, identify anatomical landmarks and relation of anatomical features and the anatomical landmarks to normalities and abnormalities to determine mapping data of the anatomy.

According to an embodiment of the system, the system further comprises an abnormality distribution assessment module for evaluating the distribution of abnormalities within a tissue of the breast and extracting a summary of the distribution.

According to an embodiment of the system, the system further comprises an involvement assessment module for detecting the involvement of abnormalities with surrounding tissues, for analyzing the images to determine how abnormalities interact or invade adjacent tissues and outputting the involvement data.

According to an embodiment of the system, the system further comprises a continuity assessment module for assessing the continuity of abnormalities in tissues for determining abnormalities as isolated or continuous with other tissue structures in the image; outputting the continuity data.

According to an embodiment of the system, the system further comprises an etiologic module for determining etiologic factors of abnormalities in the image to determine potential causes or contributing factors of the abnormalities and outputting the etiologic data.

According to an embodiment of the system, the system further comprises a characterizing module for the characterization of abnormalities to provide a profile of the abnormalities and to output the profile data.

According to an embodiment of the system, the genetic data comprises one or more of Apolipoprotein E (APOE); Lipoprotein(a) (LPA), Low-Density Lipoprotein Receptor (LDLR), Proprotein Convertase Subtilisin/Kexin Type 9 (PCSK9), Tumor Necrosis Factor-alpha (TNF-alpha), Vitamin D Receptor (VDR), Transcription Factor 7-Like 2 (TCF7L2), Potassium Inwardly-Rectifying Channel Subfamily J Member 11 (KCNJ11), Peroxisome Proliferator-Activated Receptor Gamma (PPARG), Calpain 10 (CAPN10), Angiotensin-Converting Enzyme (ACE), Angiotensinogen (AGT), Angiotensin II Receptor Type 1 (AGTR1), Nitric Oxide Synthase 3 (NOS3), Cytochrome P450 Family 11 Subfamily B Member 2 (CYP11B2), Apolipoprotein B (APOB), Cholesteryl Ester Transfer Protein (CETP), Hepatic Lipase (LIPC), Apolipoprotein A5 (APOA5), 3-Hydroxy-3-Methylglutaryl-CoA Reductase (HMGCR), Interleukin 6 (IL6), Matrix Metallopeptidase 9 (MMP9), Cyclin Dependent Kinase Inhibitor 2A (CDKN2A), Advanced Glycation End Product-Specific Receptor (AGER), Secreted Phosphoprotein 1 (SPP1), Collagen Type I Alpha 1 (COL1A1), Matrix Gla Protein (MGP), Osteopontin (OPN), Solute Carrier Family 20 Member 1 (SLC20A1), Breast Cancer 1 (BRCA 1), Breast Cancer 2 (BRCA 2), Phosphatase and Tensin Homolog (PTEN), Partner and Localizer of BRCA2 (PALB 2), Tumor Protein P53 (TP53), Ataxia Telangiectasia Mutated (ATM), Retinoblastoma Protein (RB), Cadherin 1 (CDH1), Chromodomain Helicase DNA Binding Protein 1 (CHD1), Checkpoint Kinase 2 (CHEK2), Neurofibromatosis Type 1 (NF1), Nijmegen Breakage Syndrome 1 (NBN), Serine/Threonine Kinase 11 (STK11), Microsatellite Instability (MSI), BRCA1 Associated RING Domain 1 (BARD1), BRCA1 Interacting Protein C-Terminal Helicase 1 (BRIP1), Polymerase Epsilon (POLE), Tumor Necrosis Factor (TNF), Interleukin 6 and Interleukin 1 beta (IL6 & IL1beta), Matrix Metalloproteinase 3 (MMP3), Collagen Type II Alpha 1 (COL2A1), Apolipoprotein E (APOE), Presenilin 1 (PSEN1), Small Nuclear Ribonucleoprotein-Associated Polypeptide N (SNAK), Parkin RBR E3 Ubiquitin Protein Ligase (PARKIN), Human Leukocyte Antigen (HLA), Nucleotide-Binding Oligomerization Domain Containing 2 (NOD2).

According to an embodiment of the system, the second risk comprises one or more of cardiovascular risk, cardiac contractile risk, cardiac rhythm risk, renovascular and renal perfusion risk, retinopathy risk, pancreatic risk, cerebrovascular and Central Nervous System (CNS) health risk, pulmonary risk, chronic disease risk, vascular perfusion risk.

According to an embodiment of the system, the system determines the cardiovascular risk by augmenting the breast calcification vector with the genetic data and the clinical data, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1, and the clinical data comprises one or more of vitals, BMI, family history, past Coronary Artery Disease (CAD), Cardiovascular Disease (CVD), Nonalcoholic Steatohepatitis (NASH), retinopathy, Hemoglobin (Hb), Neutrophil to Lymphocyte Ratio (NLR), Neutrophil to Platelet Ratio (NPR), C-reactive protein (CRP), Lipid profile, Apolipoprotein Lipoprotein A & B (APO Lipo A & B), Erythrocyte Sedimentation Rate (ESR), Creatine Phosphokinase/Serum Creatinine (CPK/S Create), Alanine Aminotransferase, Aspartate Aminotransferase Ratio (ALT, AST ratio), Serum Potassium (S K), Calcium (CA), Sodium (Na), Troponin Levels (Trop levels), B-type Natriuretic Peptides (BNPs), and the system outputs a BIC-V cardiovascular risk score and a BIC-V cardiovascular risk assessment from the BIC-V cardiovascular risk score.

According to an embodiment of the system, the system determines the cardiac contractile risk by augmenting the breast calcification vector with the genetic data, the clinical data, and patient specific data relevant to myocardial health, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises one or more of vitals, BMI, family history, past CAD, CVD NASH, retinopathy, 6 minute walk test, Hb, NLR, NPR, CRP, Lipid profile, APO, Lipo A&B, ESR, CPK, S Create, ALT, AST ratio, S K, CA, Na, Trop levels, BNPs, TMT, and outputs a cardiac contractile score; and a cardiac contractile risk assessment from the cardiac contractile risk.

According to an embodiment of the system, the system determines the cardiac rhythm risk by augmenting the breast calcification vector with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A; and wherein the clinical data comprises one or more of vitals, BMI, family history, past CAD, CVD NASH, retinopathy, Hb, NLR, NPR, CRP, Lipid profile, APO, Lipo A&B, ESR, CPK, S Create, ALT, AST ratio, S K, CA, Na, Trop levels, BNPs and outputs a cardiac rhythm risk score; and a cardiac rhythm risk assessment from the cardiac rhythm risk score.

According to an embodiment of the system, the system determines the renovascular and renal perfusion risk by augmenting the breast calcification vector with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises one or more of vitals, BMI, family history, past CAD, CVD NASH, retinopathy, edema, U output, mental status, skin changes, Hb, NLR, NPR, CRP, Lipid profile, ESR, Urea, Uric acid, S Create, S K, CA, Na, BNPs, CUE, 24 hour urine protein, protein creatinine ratio, Erythropoietin (EPO), Vanillylmandelic acid (VMA), CAtahola; and wherein the system further determines a renal calcification vector from a renal image and augments the feature vector with the renal calcification vector; and outputs a renovascular and renal perfusion risk score and a renovascular and renal perfusion risk assessment from the renovascular and renal perfusion risk score.

According to an embodiment of the system, the system determines the retinopathy risk by augmenting the breast calcification vector with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises one or more of vitals, BMI, family history, past CAD, CVD NASH, Hb, NLR, NPR, CRP, Lipid profile, APO, Lipo A&B, ESR, CPK, S Create, HbA1C, Bilirubin; and wherein the system further determines a retinal calcification vector from a retinal image and augments the feature vector with the retinal calcification vector; and outputs a retinopathy risk score and a retinopathy risk assessment from the retinopathy risk score.

According to an embodiment of the system, the system determines the pancreatic risk by augmenting the breast calcification vector with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises one or more of vitals, BMI, family history, past CAD, CVD NASH, abdominal findings, food habits, Hb, NLR, NPR, CRP, Lipid profile, APO, Lipo A&B, ESR, Amylase, Lipase, CA 19.9, S Create, ALT, AST ratio, S Bilirubin; and wherein the system further determines a pancreatic calcification vector from a pancreatic image and augments the feature vector with the pancreatic calcification vector; and outputs a pancreatic risk score and a pancreatic risk assessment from the pancreatic risk score.

According to an embodiment of the system, the system determines the cerebrovascular and CNS health risk by augmenting the breast calcification vector with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises one or more of vitals, BMI, family history, past CAD, CVD NASH, retinopathy, seizures, stroke, neuropathy, Hb, NLR, NPR, CRP, Lipid profile, APO, Lipo A&B, ESR, CPK, S Create, ALT, AST ratio, S K, CA, Na, Trop levels, BNPs; and wherein the system further determines a cerebral calcification vector from a neuro image and augments the feature vector with the cerebral calcification vector; and outputs a cerebrovascular and CNS health risk score and a cerebrovascular and CNS health risk assessment from the cerebrovascular and CNS health risk score.

According to an embodiment of the system, the system determines the pulmonary risk by augmenting the breast calcification vector with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises one or more of vitals, BMI, family history, past CAD, CVD NASH, retinopathy, Hb, NLR, NPR, CRP, Lipid profile, APO, Lipo A&B, ESR, CPK, S Create, ALT, AST ratio, S K, CA, Na, Trop levels, BNPs; and outputs a pulmonary risk score and a pulmonary risk assessment from the pulmonary risk score.

According to an embodiment of the system, the system determines the chronic disease risk by augmenting the breast calcification vector with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises one or more of vitals, BMI, family history, past CAD, CVD NASH, retinopathy, Hb, NLR, NPR, CRP, Lipid profile, APO, Lipo A&B, ESR, CPK, S Create, ALT, AST ratio, S K, CA, Na, Trop levels, BNPs; and wherein the system further determines a systemic calcification vector from a systemic image and augments the feature vector with the systemic calcification vector; and outputs a chronic disease risk score and a chronic disease risk assessment from the chronic disease risk score.

According to an embodiment of the system, the system determines the vascular perfusion risk by augmenting the breast calcification vector with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises one or more of vitals, BMI, family history, past CAD, CVD NASH, retinopathy, Hb, NLR, NPR, CRP, Lipid profile, APO, Lipo A&B, ESR, CPK, S Create, ALT, AST ratio, S K, CA, Na, Trop levels, BNPs; and wherein the system further determines a vascular calcification vector from a vascular image and augments the feature vector with the vascular calcification vector; and outputs a vascular perfusion risk score and a vascular perfusion risk assessment from the vascular perfusion risk score.

According to an embodiment of the system, the system determines the healing response by augmenting the breast calcification vector with the genetic data, the clinical data, a classification vector indicative of electrical pathways; patient specific data with arrhythmias, wherein the genetic data comprises Breast cancer gene 1 (BRCA1), Breast cancer gene 2 (BRCA2), Phosphatase and tensin homolog (PTEN), Partner and localizer of BRCA2 (PALB2), Tumor protein p53 (TP53), Ataxia telangiectasia mutated (ATM), Retinoblastoma protein (RB), Cadherin 1 (CDH1), Cadherin 2 (CDH2), Checkpoint kinase 2 (CHEK2), Neurofibromatosis type 1 (NF1), Nibrin (NBN), Serine/threonine kinase 11 (STK11), Microsatellite instability (MSI), BRCA1 associated RING domain protein (BARD1), BRCA1 interacting protein C-terminal helicase 1 (BRIP1), DNA polymerase epsilon (POLE); and wherein the clinical data comprises one or more of vitals, BMI, family history, past CAD, CVD NASH, retinopathy, cancer treatment; Carcinoembryonic antigen (CEA), Cancer antigen 19.9 (CA19.9), Cancer antigen 15.3 (CA15.3), Cancer antigen 125 (CA125), Prostate-specific antigen (PSA), Estradiol (E2), Complete blood count (CBC), Renal function test (RFT), Liver function test (LFT), Thyroid function test (TFT), Lipid; and wherein the system further determines a regeneration site calcification vector from a healing or regeneration site image and augments the feature vector with the regeneration site calcification vector; and outputs a healing response score and a healing or recovery assessment from the healing response score.

According to an embodiment of the system, the system determines the tumor flow and growth by augmenting the breast calcification vector with the genetic data, the clinical data, a classification vector indicative of electrical pathways; patient specific data with arrhythmias, wherein the genetic data comprises Breast cancer gene 1 (BRCA1), Breast cancer gene 2 (BRCA2), Phosphatase and tensin homolog (PTEN), Partner and localizer of BRCA2 (PALB2), Tumor protein p53 (TP53), Ataxia telangiectasia mutated (ATM), Retinoblastoma protein (RB), Cadherin 1 (CDH1), Cadherin 2 (CDH2), Checkpoint kinase 2 (CHEK2), Neurofibromatosis type 1 (NF1), Nibrin (NBN), Serine/threonine kinase 11 (STK11), Microsatellite instability/BRCA1 associated RING domain protein (MSI/BARD1), BRCA1 interacting protein C-terminal helicase 1 (BRIP1), DNA polymerase epsilon (POLE); and wherein the clinical data comprises one or more of vitals, Body mass index (BMI), family history, past CAD, CVD NASH, retinopathy, cancer treatment; CEA, CA19.9, CA15.3, CA125, PSA, Estradiol, CBC RFT, LFT, TFT, Lipid; and wherein the system further determines a tumor morphology calcification vector from a tumor morphology and associated vascular structures image and augments the feature vector with the tumor morphology calcification vector; and outputs a tumor flow and growth score and a tumor flow and growth assessment from the tumor flow and growth score.

According to an embodiment of the system, the system determines the inflammation and degeneration by augmenting the breast calcification vector with the genetic data, the clinical data, a classification vector indicative of electrical pathways; patient specific data with arrhythmias, wherein the genetic data comprising one or more of TNF, IL6, IL1B, MMP3, COL2A1, APOE, PSEN1, SNAK, PARKIN, HLA, NOD2; and wherein the clinical data comprises one or more of vitals, BMI, family history, past Coronary Artery Disease (CAD), Cardiovascular Disease (CVD), Nonalcoholic Steatohepatitis (NASH), retinopathy, cancer treatment, joint pains, osteopenia, C-Reactive Protein (CRP), Tumor Necrosis Factor (TNF), Interleukin 6 (IL6), Erythrocyte Sedimentation Rate (ESR), inflammation markers Renal Function Test (RFT), Liver Function Test (LFT), Thyroid Function Test (TFT), Neutrophil-to-Lymphocyte Ratio (NLR), Neutrophil-to-Platelet Ratio (NPR), Hemoglobin (Hb), Mean Corpuscular Volume (MCV); and wherein the system further determines a degenerative area calcification vector from an area image affected by inflammatory or degenerative changes and augments the feature vector with the degenerative area calcification vector; and outputs an inflammation and degeneration score and an inflammation and degeneration assessment from the inflammation and degeneration score.

According to an embodiment of the system, the system determines the disease relapse by augmenting the breast calcification vector with the genetic data, the clinical data, a classification vector indicative of electrical pathways; patient specific data with arrhythmias, wherein the genetic data comprises BRCA 1, BRCA 2, PTEN, PALB 2, TP53, ATM, RB, CDH1, CDH2, CHEK2, NF1, NBN, STK11, MSI, BARD, BRIPRAD, POLE; and wherein the clinical data comprises one or more of vitals, BMI, family history, past CAD, CVD NASH, retinopathy, cancer treatment, CEA, CA19.9, CA15.3, CA125, PSA, Estradiol, CBC RFT, LFT, TFT, lipid; and wherein the system further determines a diagnostic image calcification vector from a diagnostic image and augments the feature vector with the diagnostic image calcification vector; and outputs a disease relapse score and an disease relapse assessment from the disease relapse score.

According to an embodiment of the system, the system determines the adverse event by augmenting the breast calcification vector with the genetic data, the clinical data, a classification vector indicative of electrical pathways; patient specific data with arrhythmias, wherein the genetic data comprises BRCA 1, BRCA 2, PTEN, PALB 2, TP53, ATM, RB, CDH1, CDH2, CHEK2, NF1, NBN, STK11, MSI, BARD, BRIPRAD, POLE; and wherein the clinical data comprises one or more of vitals, BMI, family history, past CAD, CVD NASH, retinopathy, cancer treatment, CEA, CA19.9, CA15.3, CA125, PSA, Estradiol, CBC RFT, LFT, TFT, lipid; and wherein the system further determines a treatment cycle calcification vector from a treatment evaluation image taken during a treatment cycle and augments the feature vector with the treatment cycle calcification vector; and outputs an adverse event score and an adverse event assessment from the adverse event score.

According to an embodiment of the system, the system determines the clinical response by augmenting the breast calcification vector with the genetic data, the clinical data, a classification vector indicative of electrical pathways; patient specific data with arrhythmias, wherein the genetic data comprises BRCA 1, BRCA 2, PTEN, PALB 2, TP53, ATM, RB, CDH1, CDH2, CHEK2, NF1, NBN, STK11, MSI, BARD, BRIPRAD, POLE; and wherein the clinical data comprises one or more of vitals, BMI, family history, past CAD, CVD NASH, retinopathy, cancer treatment, CEA, CA19.9, CA15.3, CA125, PSA, Estradiol, CBC RFT, LFT, TFT, lipid; and wherein the system further determines a post treatment calcification vector from a post treatment evaluation image and augments the feature vector with the post treatment calcification vector; and outputs a clinical response score and a clinical response assessment from the clinical response score.

According to an embodiment, disclosed is a method comprising receiving a first input comprising an image of a breast of a patient; receiving a second input comprising a patient data, wherein the patient data comprises genetic data of the patient; extracting features from the image and the patient data, using machine learning models, wherein the features comprise a presence of a calcification and a calcification pattern to generate a breast calcification vector; augmenting the breast calcification vector with the genetic data to generate a feature vector; determining, using the machine learning models, a first output comprising a first risk for a breast cancer; determining, using the machine learning models, a second output comprising a second risk to one or more organs of the patient, wherein the organs comprises one or more of a heart, a kidney, lungs, a pancreas, and a brain of the patient; predicting, using the machine learning models, a third output comprising a third risk based on one or more of a healing response, a tumor flow and growth, inflammation and degeneration, a disease relapse, an adverse event, and a clinical response of the patient; and determining, using a statistical model, a fourth output comprising an overall risk to the patient based on the first risk, the second risk, and the third risk; wherein the machine learning models are pre-trained, wherein pre-training comprises training the machine learning models using training data from plurality of patients, wherein the training data corresponding to each patient from the plurality of patients comprises one or more of breast images, chest images, organ images, genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

According to an embodiment of the method, the image comprises one or more of mammogram image, ultrasound image, computed tomography image, and magnetic resonance image.

According to an embodiment of the method, the calcification pattern comprises one or more modules comprising deep learning models to determine one or more of a location, a spread, a nature, a size, a shape, a density, an anatomy, a distribution, an involvement, a continuity, an etiologic, and a characterization of breast arterial calcifications.

According to an embodiment of the method, the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A, BRCA 1, BRCA 2, PTEN, PALB 2, TP53, ATM, RB, CDH1, CHDI2, CHEK2, NF1, NBN, STK11, MSI, BARD, BRIPRAD, POLE, TNF, IL6&1beta, MMP3, COL2A1, APOE, PSEN1, SNAK, PARKIN, HLA, NOD2.

According to an embodiment of the method, the second risk comprises one or more of cardiovascular risk, cardiac contractile risk, cardiac rhythm risk, renovascular and renal perfusion risk, retinopathy risk, pancreatic risk, cerebrovascular and CNS health risk, pulmonary risk, chronic disease risk, vascular perfusion risk.

According to an embodiment, disclosed is a non-transitory computer-readable medium having stored thereon instructions executable by a computer system to perform operations comprising, receiving a first input comprising an image of a breast of a patient; receiving a second input comprising a patient data, wherein the patient data comprises genetic data of the patient; extracting features from the image and the patient data, using machine learning models, wherein the features comprise a presence of a calcification and a calcification pattern to generate a breast calcification vector; augmenting the breast calcification vector with the genetic data to generate a feature vector; determining, using the machine learning models, a first output comprising a first risk for a breast cancer; determining, using the machine learning models, a second output comprising a second risk to one or more organs of the patient, wherein the organs comprises one or more of a heart, a kidney, lungs, a pancreas, and a brain of the patient; predicting, using the machine learning models, a third output comprising a third risk based on one or more of a healing response, a tumor flow and growth, inflammation and degeneration, a disease relapse, an adverse event, and a clinical response of the patient; and determining, using a statistical model, a fourth output comprising an overall risk to the patient based on the first risk, the second risk, and the third risk; wherein the machine learning models are pre-trained, wherein pre-training comprises training the machine learning models using training data from plurality of patients, wherein the training data corresponding to each patient from the plurality of patients comprises one or more of breast images, chest images, organ images, genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

According to the non-transitory computer-readable medium, the image comprises one or more of mammogram image, ultrasound image, computed tomography image, and magnetic resonance image.

According to the non-transitory computer-readable medium, the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A, BRCA 1, BRCA 2, PTEN, PALB 2, TP53, ATM, RB, CDH1, CHDI2, CHEK2, NF1, NBN, STK11, MSI, BARD, BRIPRAD, POLE, TNF, IL6, IL1beta, MMP3, COL2A1, APOE, PSEN1, SNAK, PARKIN, HLA, NOD2.

BRIEF DESCRIPTION OF THE FIGURES

These and other aspects of the present invention will now be described in more detail, with reference to the appended drawings showing exemplary embodiments of the present invention, in which:

FIG. 2 shows the detailed input vectors and the output risk predictions for multiple organs according to an embodiment.

FIG. 21A shows genetic markers input for BIC-V group according to an embodiment.

FIG. 21B shows individual level score for BIC-B group according to an embodiment.

FIG. 22A shows clinical data input for BIC-V group according to an embodiment.

FIG. 22B shows clinical data input for BIC-V group according to an embodiment.

DETAILED DESCRIPTION

Definitions and General Techniques

Figure 1:
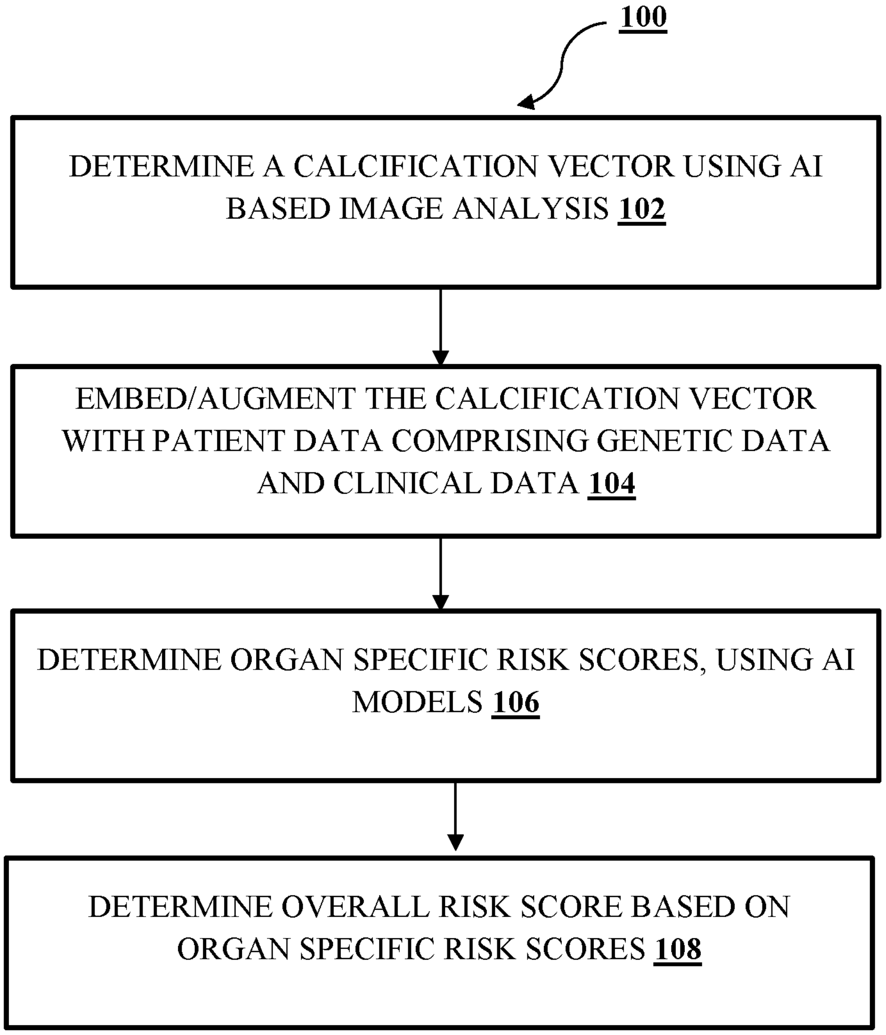
FIG. 1 shows a process executed by the system to detect the risk of cancer according to an embodiment.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, two or more elements are "integral" if they are comprised of the same piece of material. As defined herein, two or more elements are "non-integral" if each is comprised of a different piece of material.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present disclosure may be embodied in other specific forms without departing from its spirit or characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

Digital electronic circuitry, or computer software, firmware, or hardware, including the structures disclosed in this specification and their structural equivalents, or in combinations of one or more of them may realize the implementations and all of the functional operations described in this specification. Implementations may be as one or more computer program products i.e., one or more modules of computer program instructions encoded on a computer-readable medium for execution by, or to control the operation of, data processing apparatus. The computer-readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that encodes information for transmission to a suitable receiver apparatus.

The actual specialized control hardware or software code used to implement these systems and/or methods is not limiting to the implementations. Thus, any software and any hardware can implement the systems and/or methods based on the description herein without reference to specific software code.

A computer program (also known as a program, software, software application, script, or code) is written in any appropriate form of programming language, including compiled or interpreted languages. Any appropriate form, including a standalone program or a module, component, subroutine, or other unit suitable for use in a computing environment may deploy it.

A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may execute on one computer or on multiple computers that are located at one site or distributed across multiple sites and interconnected by a communication network.

One or more programmable processors, executing one or more computer programs to perform functions by operating on input data and generating output, perform the processes and logic flows described in this specification. The processes and logic flows may also be performed by, and apparatus may also be implemented as, special purpose logic circuitry, for example, without limitation, a Field Programmable Gate Array (FPGA), an Application Specific Integrated Circuit (ASIC), Application Specific Standard Products (ASSPs), System-On-a-Chip (SOC) systems, Complex Programmable Logic Devices (CPLDs), etc.

Processors suitable for the execution of a computer program include, by way of example, both general and special purpose microprocessors, and any one or more processors of any appropriate kind of digital computer. A processor will receive instructions and data from a read-only memory or a random-access memory or both. Elements of a computer can include a processor for performing instructions and one or more memory devices for storing instructions and data. A computer will also include, or is operatively coupled to receive data, transfer data or both, to/from one or more mass storage devices for storing data e.g., magnetic disks, magneto optical disks, optical disks, or solid-state disks. However, a computer need not have such devices. Moreover, another device, e.g., a mobile telephone, a personal digital assistant (PDA), a mobile audio player, a Global Positioning System (GPS) receiver, etc. may embed a computer. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD ROM) disks, Digital Versatile Disk-Read-Only Memory (DVD-ROM) disks) and solid-state disks. Special purpose logic circuitry may supplement or incorporate the processor and the memory.

To provide for interaction with a user, a computer may have a display device, e.g., a Cathode Ray Tube (CRT) or Liquid Crystal Display (LCD) monitor, for displaying information to the user, and a keyboard and a pointing device, e.g., a mouse or a trackball, by which the user may provide input to the computer. Other kinds of devices provide for interaction with a user as well. For example, feedback to the user may be any appropriate form of sensory feedback, e.g., visual feedback, auditory feedback, or tactile feedback; and a computer may receive input from the user in any appropriate form, including acoustic, speech, or tactile input.

A computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components, may realize implementations described herein. Any appropriate form or medium of digital data communication, e.g., a communication network may interconnect the components of the system. Examples of communication networks include a Local Area Network (LAN) and a Wide Area Network (WAN), e.g., Intranet and Internet.

The computing system may include clients and servers. A client and server are remote from each other and typically interact through a communication network. The relationship of the client and server arises by virtue of computer programs running on the respective computers and having a client-server relationship with each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media can be any media accessible by a general purpose or special purpose computer system. Computer-readable media that store computer-executable instructions are physical storage media. Computer-readable media that carry computer-executable instructions are transmission media. Thus, by way of example and not limitation, embodiments of the invention can comprise at least two distinct kinds of computer-readable media: physical computer-readable storage media and transmission computer-readable media.

Although the present embodiments described herein are with reference to specific example embodiments it will be evident that various modifications and changes may be made to these embodiments without departing from the broader spirit and scope of the various embodiments. For example, hardware circuitry (e.g., Complementary Metal Oxide Semiconductor (CMOS) based logic circuitry), firmware, software (e.g., embodied in a non-transitory machine-readable medium), or any combination of hardware, firmware, and software may enable and operate the various devices, units, and modules described herein. For example, transistors, logic gates, and electrical circuits (e.g., Application Specific Integrated Circuit (ASIC) and/or Digital Signal Processor (DSP) circuit) may embody the various electrical structures and methods.

In addition, a non-transitory machine-readable medium and/or a system may embody the various operations, processes, and methods disclosed herein. Accordingly, the specification and drawings are illustrative rather than restrictive.

Physical computer-readable storage media includes RAM, ROM, EEPROM, CD-ROM or other optical disk storage (such as CDs, DVDs, etc.), magnetic disk storage or other magnetic storage devices, solid-state disks or any other medium. They store desired program code in the form of computer-executable instructions or data structures which can be accessed by a general purpose or special purpose computer.

As used herein, the term "network" refers to one or more data links that enable the transport of electronic data between computer systems and/or modules and/or other electronic devices. When a network or another communications connection (either hardwired, wireless, or a combination of hardwired or wireless) transfers or provides information to a computer, the computer properly views the connection as a transmission medium. A general purpose or special purpose computer access transmission media that can include a network and/or data links which carry desired program code in the form of computer-executable instructions or data structures. The scope of computer-readable media includes combinations of the above, that enable the transport of electronic data between computer systems and/or modules and/or other electronic devices. The term network may include the Internet, a local area network, a wide area network, or combinations thereof. The network may include one or more networks or communication systems, such as the Internet, the telephone system, satellite networks, cable television networks, and various other private and public networks. In addition, the connections may include wired connections (such as wires, cables, fiber optic lines, etc.), wireless connections, or combinations thereof.

Furthermore, although not shown, other computers, systems, devices, and networks may also be connected to the network. Network refers to any set of devices or subsystems connected by links joining (directly or indirectly) a set of terminal nodes sharing resources located on or provided by network nodes. The computers use common communication protocols over digital interconnections to communicate with each other. For example, subsystems may comprise the cloud. Cloud refers to servers that are accessed over the Internet, and the software and databases that run on those servers.

Further, upon reaching various computer system components, program code in the form of computer-executable instructions or data structures can be transferred automatically from transmission computer-readable media to physical computer-readable storage media (or vice versa). For example, computer-executable instructions or data structures received over a network or data link can be buffered in RAM within a Network Interface Module (NIC), and then eventually transferred to computer system RAM and/or to less volatile computer-readable physical storage media at a computer system. Thus, computer system components that also (or even primarily) utilize transmission media may include computer-readable physical storage media.

Computer-executable instructions comprise, for example, instructions and data which cause a general purpose computer, special purpose computer, or special purpose processing device to perform a certain function or group of functions. The computer-executable instructions may be, for example, binary, intermediate format instructions such as assembly language, or even source code. Although the subject matter herein described is in a language specific to structural features and/or methodological acts, the described features or acts described do not limit the subject matter defined in the claims. Rather, the herein described features and acts are example forms of implementing the claims.

While this specification contains many specifics, these do not construe as limitations on the scope of the disclosure or of the claims, but as descriptions of features specific to particular implementations. A single implementation may implement certain features described in this specification in the context of separate implementations. Conversely, multiple implementations separately or in any suitable subcombination may implement various features described herein in the context of a single implementation. Moreover, although features described herein as acting in certain combinations and even initially claimed as such, one or more features from a claimed combination may in some cases be excised from the combination, and the claimed combination may be directed to a sub-combination or variation of a sub-combination.

Similarly, while operations depicted herein in the drawings in a particular order to achieve desired results, this should not be understood as requiring that such operations be performed in the particular order shown or in sequential order or that all illustrated operations be performed, to achieve desirable results. In certain circumstances, multitasking and parallel processing may be advantageous. Moreover, the separation of various system components in the implementations should not be understood as requiring such separation in all implementations, and it should be understood that the described program components and systems may be integrated together in a single software product or packaged into multiple software products.

Even though particular combinations of features are recited in the claims and/or disclosed in the specification, these combinations are not intended to limit the disclosure of possible implementations. Other implementations are within the scope of the claims. For example, the actions recited in the claims may be performed in a different order and still achieve desirable results. In fact, many of these features may be combined in ways not specifically recited in the claims and/or disclosed in the specification. Although each dependent claim may directly depend on only one claim, the disclosure of possible implementations includes each dependent claim in combination with every other claim in the claim set.

Further, a computer system including one or more processors and computer-readable media such as computer memory may practice the methods. In particular, one or more processors execute computer-executable instructions, stored in the computer memory, to perform various functions such as the acts recited in the embodiments.

Those skilled in the art will appreciate that the invention may be practiced in network computing environments with many types of computer system configurations including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, etc. Distributed system environments where local and remote computer systems, which are linked (either by hardwired data links, wireless data links, or by a combination of hardwired and wireless data links) through a network, both perform tasks may also practice the invention. In a distributed system environment, program modules may be located in both local and remote memory storage devices.

As used herein "Machine learning" refers to algorithms that give a computer the ability to learn without explicit programming, including algorithms that learn from and make predictions about data. Machine learning techniques include, but are not limited to, support vector machine, artificial neural network (ANN) (also referred to herein as a "neural net"), deep learning neural network, logistic regression, discriminant analysis, random forest, linear regression, rules-based machine learning, Naive Bayes, nearest neighbor, decision tree, decision tree learning, and hidden Markov, etc. For the purposes of clarity, part of a machine learning process can use algorithms such as linear regression or logistic regression. However, using linear regression or another algorithm as part of a machine learning process is distinct from performing a statistical analysis such as regression with a spreadsheet program. The machine learning process can continually learn and adjust the classifier as new data becomes available and does not rely on explicit or rules-based programming. The ANN may be featured with a feedback loop to adjust the system output dynamically as it learns from the new data as it becomes available. In machine learning, backpropagation and feedback loops are used to train the Artificial Intelligence/Machine Learning (AI/ML) model improving the model's accuracy and performance over time. Statistical modeling relies on finding relationships between variables (e.g., mathematical equations) to predict an outcome.

As used herein, the term "Data mining" is a process used to turn raw data into useful information. It is the process of analyzing large datasets to uncover hidden patterns, relationships, and insights that can be useful for decision-making and prediction.

As used herein, the term "Data acquisition" is the process of sampling signals that measure real world physical conditions and converting the resulting samples into digital numeric values that a computer manipulates. Data acquisition systems typically convert analog waveforms into digital values for processing. The components of data acquisition systems include sensors to convert physical parameters to electrical signals, signal conditioning circuitry to convert sensor signals into a form that can be converted to digital values, and analog-to-digital converters to convert conditioned sensor signals to digital values. Stand-alone data acquisition systems are often called data loggers.

As used herein, the term "Dashboard" is a type of interface that visualizes particular Key Performance Indicators (KPIs) for a specific goal or process. It is based on data visualization and infographics.

As used herein, a "Database" is a collection of organized information so that it can be easily accessed, managed, and updated. Computer databases typically contain aggregations of data records or files.

As used herein, the term "Data set" (or "Dataset") is a collection of data. In the case of tabular data, a data set corresponds to one or more database tables, where every column of a table represents a particular variable, and each row corresponds to a given record of the data set in question. The data set lists values for each of the variables, such as height and weight of an object, for each member of the data set. Each value is known as a datum. Data sets can also consist of a collection of documents or files.

The terms "non-transitory computer-readable medium" and "computer-readable medium" include a single medium or multiple media such as a centralized or distributed database, and/or associated caches and servers that store one or more sets of instructions. Further, the terms "non-transitory computer-readable medium" and "computer-readable medium" include any tangible medium that is capable of storing, encoding, or carrying a set of instructions for execution by a processor that, for example, when executed, cause a system to perform any one or more of the methods or operations disclosed herein. As used herein, the term "computer-readable medium" is expressly defined to include any type of computer-readable storage device and/or storage disk and to exclude propagating signals.

The term "application server" refers to a server that hosts applications or software that delivers a business application through a communication protocol. An application server framework is a service layer model. It includes software components available to a software developer through an application programming interface. It is system software that resides between the operating system (OS) on one side, the external resources such as a database management system (DBMS), communications and Internet services on another side, and the users' applications on the third side.

The term "cyber security" as used herein refers to application of technologies, processes, and controls to protect systems, networks, programs, devices, and data from cyber-attacks.

The term "cyber security module" as used herein refers to a module comprising application of technologies, processes, and controls to protect systems, networks, programs, devices and data from cyber-attacks and threats. It aims to reduce the risk of cyber-attacks and protect against the unauthorized exploitation of systems, networks, and technologies. It includes, but is not limited to, critical infrastructure security, application security, network security, cloud security, Internet of Things (IoT) security.

The term "encrypt" used herein refers to securing digital data using one or more mathematical techniques, along with a password or "key" used to decrypt the information. It refers to converting information or data into a code, especially to prevent unauthorized access. It may also refer to concealing information or data by converting it into a code. It may also be referred to as cipher, code, encipher, encode. A simple example is representing alphabets with numbers—say, 'A' is '01', 'B' is '02', and so on. For example, a message like "HELLO" will be encrypted as "0805121215," and this value will be transmitted over the network to the recipient(s).

The term "decrypt" used herein refers to the process of converting an encrypted message back to its original format. It is generally a reverse process of encryption. It decodes the encrypted information so that only an authorized user can decrypt the data because decryption requires a secret key or password. This term could be used to describe a method of unencrypting the data manually or unencrypting the data using the proper codes or keys.

The term "cyber security threat" used herein refers to any possible malicious attack that seeks to unlawfully access data, disrupt digital operations, or damage information. A malicious act includes but is not limited to damaging data, stealing data, or disrupting digital life in general. Cyber threats include, but are not limited to, malware, spyware, phishing attacks, ransomware, zero-day exploits, trojans, advanced persistent threats, wiper attacks, data manipulation, data destruction, rogue software, malvertising, unpatched software, computer viruses, man-in-the-middle attacks, data breaches, Denial of Service (DoS) attacks, and other attack vectors.

The term "hash value" used herein can be thought of as fingerprints for files. The contents of a file are processed through a cryptographic algorithm, and a unique numerical value, the hash value, is produced that identifies the contents of the file. If the contents are modified in any way, the value of the hash will also change significantly. Example algorithms used to produce hash values: the Message Digest-5 (MD5) algorithm and Secure Hash Algorithm-1 (SHA1).

The term "integrity check" as used herein refers to the checking for accuracy and consistency of system related files, data, etc. It may be performed using checking tools that can detect whether any critical system files have been changed, thus enabling the system administrator to look for unauthorized alteration of the system. For example, data integrity corresponds to the quality of data in the databases and to the level by which users examine data quality, integrity, and reliability. Data integrity checks verify that the data in the database is accurate, and functions as expected within a given application.

The term "alarm" as used herein refers to a trigger when a component in a system or the system fails or does not perform as expected. The system may enter an alarm state when a certain event occurs. An alarm indication signal is a visual signal to indicate the alarm state. For example, when a cyber security threat is detected, a system administrator may be alerted via sound alarm, a message, a glowing LED, a pop-up window, etc. Alarm indication signal may be reported downstream from a detecting device, to prevent adverse situations or cascading effects.

As used herein, the term "cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it can be used to implement multiple, interoperable versions of a program. Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation. Hashing algorithms may be used to verify the integrity of data. Secure Socket Layer (SSL) and Transport Layer Security (TLS), the successor to SSL, are cryptographic protocols that may be used by networking switches to secure data communications over a network.

The embodiments described herein can be directed to one or more of a system, a method, an apparatus, and/or a computer program product at any possible technical detail level of integration. The computer program product can include a computer-readable storage medium (or media) having computer-readable program instructions thereon for causing a processor to carry out aspects of the one or more embodiments described herein.

The flowcharts and block diagrams in the figures illustrate the architecture, functionality and/or operation of possible implementations of systems, computer-implementable methods and/or computer program products according to one or more embodiments described herein. In this regard, each block in the flowchart or block diagrams can represent a module, segment and/or portion of instructions, which comprises one or more executable instructions for implementing the specified logical function(s). In one or more alternative implementations, the functions noted in the blocks can occur out of the order noted in the Figures. For example, two blocks shown in succession can be executed substantially concurrently, and/or the blocks can sometimes be executed in the reverse order, depending upon the functionality involved. It will also be noted that each block of the block diagrams and/or flowchart illustration, and/or combinations of blocks in the block diagrams and/or flowchart illustration, can be implemented by special purpose hardware-based systems that can perform the specified functions and/or acts and/or carry out one or more combinations of special purpose hardware and/or computer instructions.

As used in this application, the terms “component,” “system,” “platform,” “interface,” and/or the like, can refer to and/or can include a computer-related entity or an entity related to an operational machine with one or more specific functionalities. The entities described herein can be either hardware, a combination of hardware and software, software, or software in execution. For example, a component can be, but is not limited to being, a process running on a processor, a processor, an object, an executable, a thread of execution, a program and/or a computer. By way of illustration, both an application running on a server and the server can be a component. One or more components can reside within a process and/or thread of execution and a component can be localized on one computer and/or distributed between two or more computers. In another example, respective components can execute from various computer-readable media having various data structures stored thereon. The components can communicate via local and/or remote processes such as in accordance with a signal having one or more data packets (e.g., data from one component interacting with another component in a local system, distributed system and/or across a network such as the Internet with other systems via the signal). As another example, a component can be an apparatus with specific functionality provided by mechanical parts operated by electric or electronic circuitry, which is operated by a software and/or firmware application executed by a processor. In such a case, the processor can be internal and/or external to the apparatus and can execute at least a part of the software and/or firmware application. As yet another example, a component can be an apparatus that provides specific functionality through electronic components without mechanical parts, where the electronic components can include a processor and/or other means to execute software and/or firmware that confers at least in part the functionality of the electronic components. In an aspect, a component can emulate an electronic component via a virtual machine, e.g., within a cloud computing system.

The embodiments described herein include mere examples of systems and computer-implemented methods. It is, of course, not possible to describe every conceivable combination of components and/or computer-implemented methods for purposes of describing the one or more embodiments, but one of ordinary skill in the art can recognize that many further combinations and/or permutations of the one or more embodiments are possible. Furthermore, to the extent that the terms “includes,” “has,” “possesses,” and the like are used in the detailed description, claims, appendices and/or drawings such terms are intended to be inclusive in a manner similar to the term “comprising” as “comprising” is interpreted when employed as a transitional word in a claim.

The methods and techniques of the present disclosure are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

The following terms and phrases, unless otherwise indicated, shall be understood to have the following meanings.

As used herein the term “organ” refers to a differentiated structure within an organism, consisting of cells and tissues that perform specific functions. Examples include the brain, heart, lungs, kidneys, liver, breast, and other bodily parts.

As used herein the term “diagnostic radiology” refers to the field of medical imaging that encompasses various techniques, image modalities, for visualizing internal structures and diagnosing medical conditions. These techniques include X-rays, mammography, MRI (Magnetic Resonance Imaging), CT (Computed Tomography), and ultrasound. Diagnostic radiology plays a crucial role in healthcare by aiding in the detection, assessment, and monitoring of diseases and injuries.

As used herein the term “mammogram” refers to an X-ray imaging system specifically focused on breast tissue. It is commonly used for breast cancer screening and diagnostic purposes. The procedure involves compressing the breast between two plates to obtain detailed images that aid in early detection and assessment of abnormalities.

As used herein the term “ultrasound image” refers to a visual representation obtained through ultrasound imaging. An ultrasound uses high-frequency sound waves to create real-time images of internal structures, such as organs, blood vessels, and tissues. These images are valuable for medical diagnosis, monitoring pregnancies, and assessing various health conditions.

As used herein the term “Computed Tomography (CT) Image”, also known as a CAT scan image, is generated using computed tomography. It involves taking X-ray images from multiple angles around the body and then reconstructing cross-sectional slices. CT images provide detailed information about internal structures, such as bones, soft tissues, and blood vessels.

As used herein the term "Magnetic Resonance Image (MRI) image" is created using magnetic resonance imaging. It uses strong magnetic fields and radio waves to produce detailed images of various body parts, including the brain, joints, and organs. An MRI provides excellent soft tissue contrast and is commonly used for diagnostic purposes.

As used herein the term "calcification" refers to the accumulation of calcium salts in body tissues. It can occur in various places throughout the body, including arteries, heart valves, brain, joints, tendons, soft tissues, and organs. While some calcifications are harmless, others can disrupt organ function and affect blood vessels. Calcification characteristics involve describing and quantifying the properties of the calcified regions.

Calcification characteristics, includes the factors listed below:

Location indicates where the calcified area is situated within a tissue or organ.

Spread indicates how widely the calcified regions are distributed within a particular tissue or system.

Nature encompasses factors like the chemical composition of the calcified deposits and their interaction with surrounding tissues.

Shape refers to the geometric configuration of the calcified areas, which can vary from nodules to linear patterns.

Size quantifies the extent of the calcified regions, whether they are small focal spots or larger areas.

Density characterizes how densely the calcium deposits are distributed within the affected tissue.

Anatomy involves understanding the anatomical context of the affected area, such as the specific tissue layers or organs involved.

Distribution refers to the spatial arrangement of the calcified regions within the tissue or organ.

Involvement relates to how extensively the surrounding structures are affected by the calcified deposits.

Continuity indicates whether the calcified areas form a continuous pattern or are localized with discrete foci.

Etiologic factors contribute to the formation of calcium deposits, such as metabolic disorders or inflammation.

As used herein the term "arterial calcification" refers to the deposition of calcium in the walls of arteries. It can occur in various arteries throughout the body, including coronary arteries (associated with heart disease), carotid arteries (linked to stroke risk), and peripheral arteries. Arterial calcification can lead to reduced blood flow, increased stiffness of the arteries, and potential complications.

As used herein the term "vascular calcification" encompasses calcification in any blood vessel, including both arteries and veins. These calcifications can affect blood flow, vessel elasticity, and overall cardiovascular health. They are often associated with conditions like atherosclerosis and chronic kidney disease.

As used herein the term "breast cancer" refers to a malignant tumor that originates in the breast tissue. It can occur in both men and women but is more common in women. Early detection through methods like mammography is crucial for successful treatment and improved outcomes.

As used herein the term "coronary artery disease (CAD)" refers to conditions affecting the coronary arteries, which supply blood to the heart muscle. CAD includes atherosclerosis (narrowing of arteries due to plaque buildup), angina (chest pain), and heart attacks (myocardial infarctions).

As used herein the term "cardiovascular" refers to the heart and blood vessels collectively. It encompasses the circulatory system, including the heart, arteries, veins, and capillaries.

As used herein the term "chronic disease" refers to conditions that last for one year or more and require ongoing medical attention or limit daily activities. Examples include heart disease, cancer, diabetes, and chronic respiratory diseases.

As used herein the term "cardiac contractility" refers to the strength of heart muscle cells (cardiomyocytes) to contract. It plays a crucial role in pumping blood throughout the body. Depolarization of cardiomyocytes triggers contractions, allowing the heart to function effectively.

As used herein the term "cardiac rhythm" refers to the regular pattern of heartbeats. Abnormalities in heart rhythm (arrhythmias) can cause the heart to beat too fast (tachycardia) or too slow (bradycardia).

As used herein the term "renal problems" refers to conditions affecting the kidneys, vital organs responsible for filtering waste products from the blood, regulating electrolytes, and maintaining fluid balance. Examples include kidney infections, kidney stones, and renal failure.

As used herein the term "retina health" specifically refers to the well-being and optimal functioning of the retina, which is the light-sensitive layer at the back of the eyeball. The retina captures light and converts it into electrical signals that are transmitted to the brain via the optic nerve, allowing us to perceive visual images. Maintaining good retina health is essential for preserving vision and preventing conditions like retinopathy or age-related macular degeneration As used herein the term "retinopathy" refers to damage to the retina, often caused by conditions like diabetes or high blood pressure. It can lead to vision loss if left untreated.

As used herein the term "pancreatic diseases" encompasses various conditions affecting the pancreas, including inflammation (pancreatitis), cysts, tumors, and cancer.

As used herein the term "neurological health" relates to the well-being of the nervous system, including the brain and spinal cord. Cerebrovascular health pertains to blood flow and function within the brain, crucial for preventing strokes and maintaining cognitive function.

As used herein the term "Central Nervous System (CNS)" includes the brain and spinal cord. CNS health involves maintaining optimal function, preventing disorders, and addressing any neurological issues.

As used herein the term "lung function" refers to the capacity of the lungs to exchange oxygen and remove carbon dioxide.

As used herein the term "Chronic Obstructive Pulmonary Disease (COPD)" refers to a progressive lung disease characterized by airflow limitation, including conditions like chronic bronchitis and emphysema.

As used herein the term "pulmonary conditions" encompasses various lung-related disorders, such as asthma, pneumonia, and pulmonary fibrosis. These conditions affect breathing and lung function.

As used herein the term "critical vascular perfusion" refers to the optimal blood flow necessary for maintaining tissue viability and preventing ischemia (insufficient blood supply). Critical vascular perfusion is crucial for overall health and healing.

As used herein the term "lesions" refers to regions in an organ or tissue that have suffered damage due to injury or disease. Examples include wounds, ulcers, abscesses, or tumors. Lesions can be circumscribed and well-defined.

The term "biology of lesion" refers to the study of structural or biochemical changes in tissues caused by disease processes or injuries. These alterations can occur in various organs or tissues and may be associated with specific symptoms.

As used herein the term "genetic data" refers to personal data related to the inherited or acquired genetic characteristics of an individual. Genetic data provides unique information about an individual's physiology or health based on an analysis of biological samples, such as DNA or RNA.

As used herein, the term "clinical data" refers to information related to the health status of patients and the care they receive within healthcare settings. This data encompasses a wide range of information collected during routine clinical care and is used for diagnosing, treating, and monitoring patients. Clinical data may include patient demographics, detailed medical history records, family medical history, known allergies. Clinical data may further include clinical observations made by healthcare, diagnostic test results, and treatment information, health monitoring data, behavioral and lifestyle information, and patient-reported outcomes. Clinical data may further include administrative data, including appointment schedules, billing information, insurance details, and patient referrals, and supports the efficient delivery of healthcare services. It may refer to information gathered for medical research and healthcare data analytics. Clinical data includes data obtained through ongoing patient care or formal clinical trials. Clinical analytics uses both historical data and real-time data to generate insights, inform decision-making, and reduce costs.

As used herein, the term "medical data", may refer to data that include all that is included in clinical data and further include administrative data comprising insurance information, billing and insurance claims data, appointment and scheduling information, patient surveys, patient-reported outcomes and satisfaction. It refers to information about an individual's state of health and the medical treatment they have received. It includes a wide range of data related to health conditions, diagnoses, treatments, clinical records, imaging, and genetic information.

As used herein the term "lab test" is a medical procedure conducted under controlled scientific conditions in a laboratory or similar setting. It involves testing samples of blood, urine, or other body fluids or tissues to diagnose diseases, screen for health conditions, or monitor treatment outcomes.

As used herein the term "genetic biomarkers", also known as "genetic markers", refers to specific DNA sequences with known physical locations on chromosomes. They help link inherited diseases to responsible genes. DNA segments, close to each other on a chromosome, tend to be inherited together, these markers aid in tracking nearby genes whose precise locations are known.

As used herein the term "biomarker", also known as "biological marker", is a measurable indicator of some biological state or condition. These markers are often evaluated using blood, urine, or soft tissues to examine normal biological processes, pathogenic processes, or pharmacologic responses to therapeutic interventions. They can be proteins, metabolites, or genetic signatures. Biomarkers provide valuable insights for diagnosis, prognosis, and personalized treatment strategies.

Given below is a partial list of biomarkers.

Alpha-Fetoprotein (AFP): Associated with liver cancer.

Carcinoembryonic Antigen (CEA): Associated with colorectal cancer.

Cancer Antigen (CA125): Associated with ovarian cancer.

Cancer Antigen 19-9 (CA19-9): Associated with pancreatic cancer.

Cancer Antigen 15-3 (CA 15-3): Associated with breast cancer.

Cytokeratin 19 fragment antigen 21-1 (CYFRA21-1): Associated with lung cancer, particularly non-small cell lung cancer (NSCLC).

Prostate-Specific Antigen (PSA): Associated with prostate cancer.

Squamous Cell Carcinoma Antigen (SCC): Associated with squamous cell carcinomas, including those in the cervix, head, and neck.

Human Epididymis Protein 4 (HE-4): Associated with ovarian cancer.

Neuron-Specific Enolase (NSE): Associated with neuroendocrine tumors and small cell lung cancer.

Pro-GRP: Associated with neuroendocrine tumors, particularly small cell lung cancer anti-Cyclin E2: Antibodies targeting Cyclin E2, a protein involved in cell cycle regulation. Its expression levels can be informative in cancer diagnosis and prognosis.

anti-MAPKAPK3: Antibodies against Mitogen-Activated Protein Kinase-Activated Protein Kinase 3 (MAPKAPK3), which plays a role in cellular stress responses. Its dysregulation is linked to cancer progression.

anti-New York Esophageal Squamous Cell Carcinoma 1 (anti-NY-ESO-1): Antibodies targeting NY-ESO-1, an antigen expressed in various cancers, including melanoma and ovarian cancer. It's used in immunotherapy approaches.

anti-p53: Antibodies against the p53 protein, a tumor suppressor. Mutations in p53 are common in cancer and impact treatment response.

Calcitonin: Hormone produced by the thyroid gland. Elevated levels may indicate medullary thyroid cancer.

Prostatic Acid Phosphatase (PAP): A marker for prostate cancer. Elevated PAP levels can indicate disease progression.

Human Epidermal Growth Factor Receptor 2 (Her-2): Breast cancer marker. Her-2 overexpression influences treatment decisions and targeted therapies.

Tumor Necrosis Factor (TNF): A cytokine involved in inflammation, immune responses, and cell death. It plays roles in fever induction, acute phase response, and tissue remodeling.

Interleukin 6 (IL6): Both a pro-inflammatory cytokine and an anti-inflammatory myokine. It regulates immune responses, cell proliferation, and differentiation.

Interleukin 1 Beta (IL1B or IL-10): A pro-inflammatory cytokine produced by macrophages. It contributes to fever, acute phase response, and tissue remodeling.

Matrix Metalloproteinase 3 (MMP3): Degrades collagen and other extracellular matrix proteins. It plays a role in tissue remodeling, wound repair, and tumor initiation.

Collagen Type II Alpha 1 (COL2A1): Encodes the pro-alpha1 (II) chain of type II collagen. Type II collagen provides structure to cartilage, bones, and other connective tissues.

Apolipoprotein E (APOE): Involved in lipid metabolism and transport. It plays a role in Alzheimer's disease risk and cholesterol regulation.

Presenilin 1 (PSEN1): Associated with early-onset Alzheimer's disease.

SNAK: Small Nuclear Ribonucleoprotein-Associated Polypeptide N.

Parkin or PARKIN: Associated with Parkinson's disease. Mutations impair protein degradation and mitochondrial function.

Human Leukocyte Antigen (HLA): Encode major histocompatibility complex (MHC) proteins. They play a crucial role in immune responses and tissue compatibility.

Nucleotide-Binding Oligomerization Domain 2 (NOD2): Involved in innate immunity and bacterial recognition. Mutations are linked to Crohn's disease and other inflammatory conditions.

BRCA1 and BRCA2: Breast cancer susceptibility genes.

As used herein the term "demographic data" refers to information about specific population groups or segments. It includes characteristics such as age, gender, ethnicity, income, education level, geographic location, and other relevant factors.

As used herein the term "lifestyle data" refers to details about an individual's habits, preferences, and daily routines. It includes information related to activities, interests, hobbies, and social behaviors.

As used herein the term "food habits data" refers to details about an individual's dietary choices, eating patterns, and nutritional preferences. It includes information on specific foods consumed, meal timings, dietary restrictions, and culinary preferences.

As used herein the term "Social Determinants of Health (SDOH)" refers to the conditions in which people are born, grow, learn, work, play, live, and age. These encompass a wide range of factors, including personal, social, and environmental elements that significantly shape an individual's health and well-being. Examples of SDOH include income, education level, job benefits (such as health insurance and paid time off), neighborhood resources (like nutritious foods and public transportation), safety, access to medical care, air and water quality, and social connections. These determinants influence health outcomes, risk for medical conditions, and overall quality of life. When considering patent applications, understanding SDOH can be crucial for innovations that impact community-wide health and well-being.

As used herein the term "ethnicity" refers to a person's cultural identity, often based on shared ancestry, language, religion, customs, and traditions. Ethnicity plays a significant role in determining health outcomes.

As used herein the term "overall health assessment" is a set of questions answered by patients. It covers personal behaviors, risks, life-changing events, health goals, priorities, and overall health. These assessments help the healthcare team and patients develop care plans. Questions may address tobacco use, stress, healthy eating, physical activity, emotional well-being, and safety issues.

As used herein the term "clinician" refers to healthcare professionals who directly provide medical care to patients. It includes doctors, nurses, physician assistants, and other licensed practitioners.

As used herein the term "treatment plan" refers to an outline of the recommended course of action for managing a patient's health condition. It includes details on medications, therapies, lifestyle modifications, and follow-up visits.

As used herein the term "care management" refers to a patient-centered approach designed to assist patients in managing medical conditions effectively. It involves coordinating care, addressing chronic illnesses, and ensuring patient needs are met.

As used herein the term "healing" refers to the process by which the body repairs damaged tissues or restores normal function after injury, illness, or surgery.

As used herein the term "recovery" refers to the overall improvement in health and well-being following medical treatment or intervention.

As used herein the term "tumor flow" refers to the circulation of blood or other fluids within a tumor.

The term "tumor growth" refers to the increase in size or mass of a tumor over time.

As used herein the term "inflammatory" refers to the body's response to injury or infection, characterized by redness, swelling, pain, and heat.

As used herein the term "degeneration" refers to the gradual deterioration or breakdown of tissues, organs, and in general health conditions.

As used herein the term "relapse" refers to a recurrence or return of symptoms or a condition after a period of improvement or remission.

As used herein the term "adverse events", also called adverse experiences, are unfavorable and unintended signs, symptoms, or diseases associated with drug use.

As used herein the term "clinical response" refers to the patient's reaction to a medical intervention (e.g., drug therapy, surgery, or treatment).

As used herein the term "BRICC-G" refers to BReast Imaging Computed Comprehensive-Genomics.

As used herein the term "Breast Cancer Information Core (BIC)" refers to a database maintained by the National Cancer Institute (NCI).

As used herein the term "BIC-V" and "BIC-B" refers to a sub score formed from a group of individual risk scores.

As used herein, "image modalities" refer to various types of images captured using different imaging techniques, each providing unique information based on the principles of their respective technologies. These modalities are widely used in fields such as medical imaging and comprise X-ray, Computed Tomography (CT), Magnetic Resonance Imaging (MRI), Ultrasound, Positron Emission Tomography (PET). Single Photon Emission Computed Tomography (SPECT), Optical Coherence Tomography (OCT) etc.

As used herein, "calcification vector" refers to a numerical representation derived from medical imaging data that quantifies the presence and extent of calcifications within tissues, such as breast tissue in mammograms. This vector is generated through image processing techniques and machine learning algorithms, which analyze the imaging data to identify, and measure calcified areas. These calcifications can be indicative of various health conditions, including cardiovascular diseases and cancers. By converting the visual information of calcifications into a vector format, AI models can effectively process and analyze this data to support diagnostic and prognostic assessments, enabling more accurate and comprehensive health evaluations. This vectorization process typically involves several steps, including image pre-processing to enhance the visibility of calcifications, feature extraction to identify relevant characteristics, and the application of algorithms to generate the final calcification vector. The calcification vector can then be used as input for various AI models, facilitating the detection and analysis of calcifications across different patient populations and imaging modalities.

As used herein, "deeper calcifications" refer to the presence of calcium deposits located within the deeper layers of tissues or organs, as opposed to superficial calcifications that occur near the surface. Deeper calcifications, for example, that are found in arteries, including coronary arteries, can be indicative of more advanced and potentially severe conditions. These deeper deposits can impede blood flow and are associated with a higher risk of complications such as heart attacks, strokes, and other cardiovascular diseases. The assessment of deeper calcifications typically requires advanced imaging techniques to accurately identify and evaluate the extent of these deposits.

As used herein, the term "T2-weighted lesions" refer to areas of tissue or anomalies that appear differently on T2-weighted magnetic resonance imaging (MRI) scans compared to surrounding tissues. In MRI imaging, different types of tissues respond differently to the T2-weighted sequences, which can highlight specific characteristics such as fluid content, inflammation, or structural abnormalities. Lesions appearing on T2-weighted images often indicate areas of interest for medical diagnosis, helping to distinguish various pathological conditions within the body. In the context of MRI (Magnetic Resonance Imaging), T2 refers to a specific type of imaging sequence used to generate images. T2-weighted MRI sequences are sensitive to the relaxation times of tissues, particularly to differences in the amount of water present. This makes T2-weighted imaging useful for detecting pathology such as edema, inflammation, and certain types of lesions that alter tissue water content. T2-weighted images appear differently from T1-weighted images, which use a different relaxation time contrast mechanism, and are thus valuable in clinical diagnostics for distinguishing between normal and abnormal tissues based on their water content characteristics.

As used herein, "temporal sequence" refers to an ordered series of events or data points that are arranged chronologically. In various contexts, this term can describe anything from the sequence of events in a process, the timing of actions, or the chronological order of data collection and analysis. In the context of cancer risk prediction and its impact on other organs or cancers, a temporal sequence refers to the chronological order in which various health events or conditions occur and are recorded over time. This can include the progression of precancerous conditions, the development of calcifications, the onset of cancer, and subsequent metastasis or impact on other organs. By analyzing these temporal sequences, researchers and clinicians can identify patterns and correlations that help predict the risk of cancer development, understand its progression, and evaluate its effects on other parts of the body. This information is helpful for early detection, targeted interventions, and effective treatment planning.

As used herein, "biochemistry", often referred to as clinical biochemistry involves analyzing bodily fluids, such as blood and urine, to diagnose and monitor diseases. These tests measure various chemical substances in the body, including electrolytes, enzymes, hormones, lipids, glucose, and proteins, to assess organ function and detect abnormalities. It may also be referred to as labs.

As used herein, "Holter test", also known as Holter monitoring, is a diagnostic procedure that involves continuously recording a patient's heart rhythm over a 24 to 48-hour period using a portable device called a Holter monitor. This test is performed to detect irregularities in the heart's electrical activity that might not be captured during a standard electrocardiogram (ECG) conducted in a clinical setting. By monitoring the heart's activity over an extended period, the Holter test helps identify arrhythmias, palpitations, unexplained fainting, and other cardiac abnormalities. It provides valuable data for diagnosing and managing heart conditions, enabling healthcare providers to tailor appropriate treatments based on the detailed, real-time cardiac information gathered during daily activities and sleep.

As used herein "continuity data" refers to the information that is generated by evaluating the presence and extent of calcifications in tissues to determine whether these calcifications are isolated or continuous with other tissue structures. This data is used for identifying the spatial relationship and progression of calcifications within the tissue, aiding in comprehensive diagnostic assessments and treatment planning.

As used herein, "involvement" refers to the extent to which surrounding structures are affected by calcified deposits. This term encompasses the degree and spread of calcifications within tissues and their impact on nearby anatomical features. Involvement includes the assessment of how far the calcifications extend, the areas they influence, and the potential implications for the functionality and health of adjacent organs and tissues. Understanding the level of involvement helps in evaluating the severity of the condition and impact on the other organs.

As used herein, "abnormalities" refer to any deviations from the typical or expected appearance, structure, or function of tissues and organs. These abnormalities can include unusual patterns or densities of calcifications in breast tissue, irregularities in blood vessel structure or function, and signs of compromised organ health, such as impaired kidney or brain circulation. Normalities, on the other hand, refer to the expected and typical characteristics of healthy tissues and organs, including consistent and uniform tissue structure, proper blood flow, and the absence of unusual calcifications or other pathological changes. Identifying abnormalities and distinguishing them from normalities is crucial for accurate diagnosis, risk assessment, and the development of effective treatment plans.

Breast cancer is a critical health issue affecting millions worldwide, and early detection and comprehensive health assessment are vital for effective treatment and management. However, current methodologies primarily focus on cancer detection without integrating broader health risk assessments.

Many breast cancer patients may have pre-existing conditions or co morbid conditions such as cardiovascular disease, diabetes, or chronic respiratory conditions. The stress of cancer and its treatment may exacerbate these conditions, leading to an increased risk of death from non-cancer causes. Physicians treating breast cancer often focus primarily on the cancer itself, potentially overlooking other health issues. This narrow focus can lead to missed opportunities for early intervention and management of other diseases that may pose significant risks to the patient. The time-limited nature of medical consultations may prevent thorough evaluations of all potential health risks and comorbid conditions.

Further, traditional cancer care does not include a comprehensive assessment of the patient's overall health. Important risk factors for other diseases, such as lifestyle factors, genetic predispositions, and concurrent health conditions, might not be fully evaluated or monitored.

Prior studies on Vascular Calcifications and Coronary Artery Diseases, with focus on vascular calcifications observed in mammograms explore the correlation between these calcifications and the risk of coronary artery diseases. Such studies typically involve retrospective analysis of mammogram images to identify calcifications and their association with cardiovascular health, suggesting that women with breast arterial calcifications might be at higher risk for coronary artery disease.

Prior studies on Breast Cancer and Other Health Risks discuss the broader health impacts on breast cancer patients, including risks of cardiovascular diseases due to treatment side effects or shared risk factors like obesity and lifestyle habits.

Prior studies on Cardiovascular and Pancreatic Disease Correlations, highlight the indirect associations between breast cancer and other diseases such as cardiovascular and pancreatic diseases, emphasizing the need for holistic health assessments in cancer patients to improve overall outcomes.

Therefore, Breast cancer patients are at an increased risk of developing other diseases, including cardiovascular and pancreatic diseases. This correlation can be attributed to various factors, including the cancer itself and the treatments administered. Breast cancer treatments, particularly radiation therapy and certain chemotherapeutic agents, have been linked to cardiovascular toxicity. For instance, radiation therapy can damage heart tissue, leading to conditions such as ischemic heart disease and cardiomyopathy. Additionally, cancer and cardiovascular disease share common risk factors such as smoking, obesity, and age, which further increases the likelihood of heart disease in breast cancer patients. Furthermore, the stress and systemic inflammation associated with cancer can exacerbate pre-existing conditions or lead to new ones, including pancreatic diseases. The intricate relationship between breast cancer and other health conditions underscores the need for comprehensive health assessments in cancer patients to ensure holistic care and improve overall outcomes. The missed detection of these comorbidities by physicians can often be attributed to the focus on treating the primary cancer, lack of awareness of the systemic effects of cancer and its treatments, and inadequate integration of multi-disciplinary care approaches.

Business Problem:

The business problem addressed herein pertains to the inadequate integration of comprehensive health risk assessments with breast cancer detection methodologies. Current clinical practices primarily focus on identifying the presence of breast cancer without considering a holistic evaluation of the patient's overall health risks. This limitation leads to suboptimal treatment strategies, overlooking other potential health issues that could impact patient outcomes and overall healthcare costs.

Technical Problem:

Breast cancer remains a foremost health challenge, and its intersection with cardio/vascular health is becoming increasingly recognized. The need for early detection and precise diagnosis of breast cancer is not only imperative for cancer management but also provides an opportunity to assess vascular health, as both conditions share common risk factors. Screening Mammograms are routinely practiced across the globe for the early detection of breast cancer, its utility is predominantly confined to identifying potential malignancies, leaving a critical gap in comprehensive patient health assessment. Given the shared risk factors and the considerable overlap in the demographic most at risk for both breast cancer and cardiovascular diseases, there is a need for a novel approach to assess both cancer and cardiovascular risks simultaneously.

This approach can leverage patient-specific data, including genetic markers and lifestyle factors, to provide a comprehensive health assessment.

Gaps in Breast Cancer Analysis

Diagnostic Precision in Breasts (density) and Cardiac Risk: imaging analysis that can elucidate features from breast tissue images, indicative of both breast pathology and cardio/vascular risk are needed.

Calcification Characterization: Microcalcifications in breast tissue, which are often considered as breast cancer markers, also indicate vascular risk when observed in breast vessels, however the pattern, the calcification can sometimes correlate with vascular calcifications.

Integrated Temporal Analysis: There is a need for comprehensive temporal imaging analysis capable of monitoring progression of breast images pointing towards any diseases including cardiac risk factors.

Multi modal data for risk assessment: There is a need for a multifactorial approach, that converges findings from image analysis with clinical/genetic/pathology data, to assess cancer and cardiovascular risks in tandem to gain more insights.

Need for Personalized Treatment for Comprehensive Health.

The technical problem addressed involves the challenge of integrating disparate health data sources and ensuring accurate, real-time analysis to provide a comprehensive health assessment alongside cancer detection. For example, breast cancer detection. It further involves the challenge of developing advanced machine learning (ML) and deep learning (DL) models to analyze multiple data sources, including images, for example, breast images, from various imaging modalities and extensive patient records encompassing demographic, genetic, and clinical information. Ensuring accurate, real-time analysis and seamless integration of these disparate data sources into a unified framework is essential for a comprehensive health assessment. Existing systems lack the models and capability to seamlessly combine various health metrics and cancer detection data as a unified framework that can support informed clinical decision-making.

Business Solution:

The business solution involves the development of an advanced diagnostic system that not only detects breast cancer at an early stage but also integrates a comprehensive health assessment to evaluate broader health risks. This system aims to provide a more complete picture of a patient's health, enabling healthcare providers to devise more effective and personalized treatment plans. By incorporating a wider range of health indicators, the proposed solution enhances patient care and optimizes resource allocation within healthcare facilities. It involves the development of an AI powered system designed to analyze breast images alongside comprehensive patient data to perform a holistic health assessment. This system aims to provide healthcare professionals with a holistic view of a patient's health, enabling them to assess a wide range of health risks and conditions beyond breast cancer that may have shared risk elements. This approach allows for more effective and personalized treatment plans, improving patient care and optimizing resource allocation within healthcare facilities.

Technical Solution:

The technical solution disclosed herein comprises an AI-powered system that leverages advanced Machine Learning (ML) and Deep Learning (DL) models to analyze breast images and comprehensive patient data. This system integrates data from electronic health records (EHRs), genomic databases, and imaging modalities to perform holistic health assessments. The AI algorithms are designed to assess various health risks and conditions, such as breast cancer risk, along with cardiovascular health, kidney functions, retinal health, pancreatic diseases and cancer, neurological and cerebrovascular health, lung function and chronic obstructive pulmonary disease (COPD), chronic diseases, critical vascular perfusion, and further predict healing processes, tumor flow and growth, inflammatory and degenerative conditions, disease relapse, and adverse events during treatment cycles.

In an embodiment, disclosed is an AI-powered system designed to analyze breast images alongside patient data to perform a comprehensive health assessment. At the core of this system comprises the integration of advanced machine learning (ML) and deep learning (DL) models, which work seamlessly to analyze a multitude of data sources, including breast images from various imaging modalities and extensive patient records encompassing demographic, genetic, and clinical information. This comprehensive approach empowers healthcare professionals to go beyond the traditional focus on breast cancer, enabling them to assess a wide range of health risks and conditions that may impact an individual's well-being.

In an embodiment, the system is designed to assess various health risks and conditions beyond breast cancer, such as Cardiovascular, Kidney and Blood Vessel Health, Retina Health, Pancreatic Disease and Cancer, Neurological and Cerebrovascular Health, Lung Function and COPD, Chronic Diseases, Critical Vascular Perfusion; and to mediate Healing Processes, track Tumor Flow and Growth, inflammatory and degenerative conditions, aid in the management of diseases like arthritis and multiple sclerosis, disease relapses, monitors and assess risks of adverse events during treatment cycles, evaluate patient response to treatments, and providing scores to tailor ongoing or future treatment plans.

The system is designed for expansive scope, which extends far beyond the traditional focus on breast cancer detection. The need for such a system arises from the recognition that current breast cancer detection methodologies are limited in scope, focusing primarily on the identification of cancer without providing a comprehensive assessment of the patient's overall health. Unlike conventional systems that are limited to a single health concern, this innovative solution assesses a broad spectrum of health risks, including cardiovascular health, kidney function, neurological well-being, pulmonary function, and more, effectively transforming the diagnostic landscape and providing a more holistic understanding of a patient's overall health status.

In an embodiment, the underlying robust health assessment capability comprises the strategic integration of both i) machine learning methods handling structured data and ii) deep learning models analyzing images within the system. This unique synergy between the two complementary approaches allows for a comprehensive and highly accurate assessment to deliver a truly transformative diagnostic experience.

In an embodiment, the system uses breast image data, typically associated with breast cancer detection, to train models that predict risks for a diverse range of health conditions. The presence and characteristics of calcifications within the breast tissue, for instance, can serve as valuable indicators of cardiovascular health, enabling the system to repurpose this information and extend the diagnostic value of mammograms and other breast imaging modalities.

The proposed AI-powered health assessment system offers a comprehensive and innovative approach to early detection, diagnosis, and personalized management of various medical conditions. Its primary application is the early detection and diagnosis of breast cancer, where the system leverages advanced deep learning models trained on extensive breast image datasets to identify subtle abnormalities and calcifications that could indicate the presence of breast cancer at an early stage. However, the system's capabilities extend beyond breast cancer, as it can also detect signs of other diseases, such as cardiovascular issues, pulmonary conditions, renal problems, and neurological or cerebrovascular health concerns.

The system's ability to integrate multi-dimensional health data, including genetic, clinical, and breast image information, allows for the creation of personalized patient management plans. By considering a wide range of patient data, healthcare providers can tailor treatment strategies to individual patients, enabling more effective chronic disease management. The comprehensive health assessments provided by the system can evaluate various aspects of a patient's health, including cardiovascular, renal, neurological, and pulmonary function, to provide a holistic view of the individual's overall well-being. This integrated approach to health assessment and personalized care has the potential to significantly improve early detection, disease prevention, and the management of chronic conditions, ultimately leading to better patient outcomes and more efficient healthcare delivery.

FIG. 1 shows a process executed by the system to detect the risk of cancer according to an embodiment.

The process 100 comprises the steps of determining the calcification vector using AI based image analysis at step 102, embedding or augmenting the calcification vector with patient data comprising genetic data and clinical data at step 104, determining organ specific risk scores using one or more AI models at step 106, and determining overall risk scores based on organ specific risk scores at step 108.

Framework for image analysis and classifying calcifications and determining calcification vector:

In an embodiment, the system determines calcifications and calcification patterns from medical images using artificial intelligence (AI) involving image acquisition from any imaging modality, preprocessing, AI model training, pattern recognition, and result interpretation.

In an embodiment, multiple images from multiple imaging modalities, for example, medical images typically mammograms, CT scans, and MRI scans, can be considered as inputs. In an embodiment, multiple images from similar imaging technology may be considered as an input. These images are then digitized, if not already, in digital form.

In an embodiment, Image preprocessing may involve various steps.

In an embodiment, preprocessing may involve Normalization: Adjusting the brightness and contrast of the image to standardize the input data.

In an embodiment, preprocessing may involve Noise Reduction: Applying filters such as Gaussian blur to reduce noise and enhance image quality.

In an embodiment, preprocessing may involve Segmentation: Identifying and isolating regions of interest (ROIs) where calcifications are likely to be present. Techniques such as thresholding, edge detection, or advanced methods like U-Net for semantic segmentation are used.

In an embodiment, AI Model training involves various steps as explained herein:

Dataset Collection: A large and diverse dataset of annotated images with known calcifications is collected. This dataset should include various types of calcifications and patterns from various patients with their specific clinical, genetic, medical, and demographic data.

Feature Extraction: Features that characterize calcifications, such as shape, size, density, and texture, are extracted from the images. This can be achieved using methods like histogram of oriented gradients (HOG), scale-invariant feature transform (SIFT), or convolutional layers in deep learning models.

Model Selection: Choosing an appropriate AI model, typically a convolutional neural network (CNN), due to its efficacy in image analysis. Advanced models like ResNet, VGG, or Inception may be employed.

Training: The model is trained using the annotated dataset. During training, the model learns to differentiate between calcifications and non-calcified regions based on the extracted features. Techniques like data augmentation are used to improve the model's robustness.

iv) Pattern Recognition: Pattern Detection May Involve Various Steps as Below:

Detection: The trained AI model is deployed to detect calcifications in new images. The shape detection module scans the images, identifying areas that match the learned features of calcifications.

Classification: Detected calcifications are classified into different types or patterns. This may include microcalcifications, macrocalcifications, and specific pathological patterns like clustered or linear formations. The AI model can use fully connected layers or additional classifiers like support vector machines (SVM) for this task. In an embodiment, any of the AI models such as Convolutional Neural Networks (CNNs), Support Vector Machines (SVM), Random Forests, Decision Trees, k-Nearest Neighbors (k-NN), Naive Bayes, Gradient Boosting Machines (GBM), Principal Component Analysis (PCA) for dimensionality reduction followed by classification, Recurrent Neural Networks (RNNs) for sequential pattern detection, Hidden Markov Models (HMMs) can be selected and trained. In an embodiment, the AI model comprises Convolutional Neural Networks (CNNs), as CNNs are found to be better suitable due to their ability to automatically and effectively capture spatial hierarchies and features within images. They have shown high performance in image classification, segmentation, and pattern recognition tasks, making them well-suited for detecting and analyzing calcification patterns in medical imaging.

v) Result Interpretation:

Visualization: The detected calcifications and their patterns are highlighted on the original images. Bounding boxes or heat maps are used to indicate the location and severity of calcifications.

Quantification: The AI model provides quantitative data, such as the number of calcifications, their sizes, and their distribution patterns. This data is crucial for assessing the risk associated with the detected calcifications.

Reporting: A comprehensive report is generated, summarizing the findings. This includes detailed descriptions of the calcification types, their patterns, and any relevant metrics that inform clinical decisions.

AI powered calcification detection and pattern determination from medical images involve a multi-step process. It begins with image acquisition and preprocessing, followed by training AI models on annotated datasets. The models detect and classify calcifications, providing detailed visual and quantitative insights that aid in accurate diagnosis and risk assessment. This process enhances the precision and efficiency of calcification analysis and contributes to better patient outcomes.

In an embodiment, the image is a breast image of a patient. In an embodiment, the image is a chest image of a patient. In an embodiment, the image can be of any organ in the body of the patient for which a calcification and a calcification pattern needs to be quantified.

Calcification refers to the accumulation of calcium salts in body tissues, which can be detected in medical imaging. Calcifications can appear in various patterns and can be classified based on their morphology, distribution, and underlying pathology. Some examples of calcification types and their patterns as found in medical images:

Example Types of Calcifications on which the AI Models are Trained Comprises:

Microcalcifications are tiny deposits of calcium in the breast tissue. They have an appearance in general as small, often less than 0.5 mm in size or a predefined size, appearing as fine, granular spots on mammograms. Such patterns are often associated with breast cancer or ductal carcinoma in situ (DCIS).

Macrocalcifications are larger calcium deposits typically found in the breast, whose appearance is in general coarse, round, and larger than 0.5 mm or a predefined size on mammograms. These are generally benign and associated with aging, injuries, or inflammation.

Vascular Calcifications are calcium deposits within the blood vessels. These calcifications have an appearance of linear or track-like patterns following the course of blood vessels on imaging. These may be indicative of atherosclerosis and can increase the risk of cardiovascular events.

Dystrophic Calcifications are calcifications that occur in damaged or necrotic tissue. Their appearance is irregular and dense, often found in areas of prior injury, surgery, or radiation. These types of calcifications are typically benign but require correlation with clinical history.

Metastatic Calcifications are calcium deposits in normal tissues, as opposed to abnormal tissues, due to abnormal calcium metabolism. Their appearance is diffuse and widespread calcifications in soft tissues, lungs, or kidneys. These are often associated with conditions like hyperparathyroidism, renal failure, or malignancies.

The above types of calcifications are given as examples, however, a huge database of such pre quantified correlations with cancer of organ disease are used to train the models to come up with patterns and vectors that represent a risk (a probability of risk) to a specific organ, the confidence score on the probability with which the risk is detected/predicted.

Further, along with calcification presence and the size, location etc., the image analysis and the AI models are trained to quantify the patterns of calcifications.

Example Patterns Comprise:

Clustered Microcalcifications, which are grouped together in small clusters, having appearance of several microcalcifications clustered in a small area on a mammogram. Such a pattern is associated with higher suspicion for malignancy, especially when irregular in shape and density.

Linear and Segmental Calcifications are calcifications arranged in a line or following the ductal structures with the appearance of linear or branching patterns that may follow the milk ducts in the breast. These are often associated with Ductal carcinoma in situ (DCIS) or invasive ductal carcinoma.

Diffuse Calcifications are scattered throughout a large area. Their appearance is widespread, a uniform distribution across the tissue on imaging. These are generally benign, often seen in conditions like fibrocystic changes or metabolic disorders.

Eggshell Calcifications are thin, curvilinear calcifications outlining a mass or cyst. Their appearance is a thin, eggshell-like rim on imaging. These are typically benign and can be seen in cysts, lymph nodes, or granulomas.

Popcorn Calcifications are large, coarse calcifications resembling popcorn. Their appearance is irregular, dense, and large calcifications on imaging. These are commonly benign, often associated with fibroadenomas in the breast.

Punctate Calcifications are tiny, dot-like calcifications scattered throughout the tissue. Their appearance is small, punctate spots on imaging. These can be benign or malignant, requiring further evaluation based on context and associated findings which may include patient's predisposition of genes, i.e., genetic marker information, clinical data, demographics, medical data, etc.

In an embodiment, a radiographic image of an organ is transformed quantitatively to a tissue composition map indicating a total amount of organ tissue; a calcification map is generated indicating position in the tissue composition map of calcified tissue; calcification free tissue composition map is generated from the tissue composition map using the position of calcified tissue in the calcification map; a vessel map of the position of vessels in the tissue composition map is generated; and the vessel map is combined with the calcification map to generate a map of vessel calcification indicating the position of calcified vessels in the tissue composition map.

In an embodiment, quantitative analysis of calcified vessels in a map of vessel calcification in a breast comprises i) counting the number of vessels with calcifications; ii) measuring the length of segments of calcifications of the vessels; iii) measuring the area of the segments of calcifications; iv) measuring of the volume of the segments of calcifications; v) measuring the density or mass of the segments of calcifications.

In an embodiment, quantitative analysis further comprises a tissue composition map which is used for classification for calcification patterns, wherein tissue composition map comprises i) measuring breast volume; ii) measuring fibroglandular tissue volume; iii) measuring calcification-free breast tissue composition; iv) measuring chest-wall-to-nipple distance; v) measuring the total length of blood vessels including calcified and uncalcified vessels; vi) counting the blood vessels including calcified and uncalcified blood vessels.

In an embodiment, measuring the breast volume includes requiring measurement of the projected breast area in a radiographic image, the breast thickness, a model for breast peripheral thickness, and a model for deformation of a breast positioning device.

In an embodiment, a density or mass of the segments of calcifications is measured using composition of the tissue in the breast determined from a breast density map.

In an embodiment, various imaging modalities are used for obtaining the medical images of the organs, for example chest or breast image in women. Examples in Medical Imaging include: Mammograms are used to detect microcalcifications which are detected in clusters, especially in the context of suspicious breast lesions. Macrocalcifications are large, scattered calcifications commonly seen in older women.

CT scans are used to detect Vascular Calcifications which are linear calcifications along the arteries, indicative of atherosclerosis. CT scans are also used to detect Dystrophic Calcifications which are irregular calcifications in areas of prior trauma or surgery.

MRI Scans are used for T2-weighted Lesions in which calcifications may appear as hypointense (dark) areas due to the lack of water content.

By classifying calcifications and their patterns accurately, clinicians can better diagnose and manage various conditions, particularly distinguishing benign from malignant diagnosis.

The medical classifications employed by physicians and radiologists are based on their experience and judgment, introducing an element of subjectivity. Typically, radiologists examine images solely on the basis of imaging patterns, without additional patient data information. They rely on these fundamental patterns to evaluate the nature and significance of calcifications, which in turn influences treatment decisions and patient care. However, in the absence of advanced imaging technology and comprehensive patient data, such conclusions can be premature and susceptible to error and subjectivity.

The AI based classification of calcification and calcification patterns in images provide the quantified images as a calcification vector. An example of a calcification vector in medical imaging can be understood as a representation of various features that describe calcifications in a quantitative and structured manner. This vector can further be used as an input to machine learning models/AI Models along with other inputs such as clinical, medical, demographics, genetic, SODH, for classification, prediction of diseases or other analytical purposes.

An example of a calcification vector that includes multiple attributes relevant to characterizing calcifications: Consider a calcification vector C that encapsulates various features of calcifications detected in a mammogram: C=[S, D,T,L,V,G,C]

Where each component represents a specific attribute:

S (Size): The size of the calcification. Value: Measured in millimeters (e.g., 2.5 mm).

D (Density): The density of the calcification. Value: Measured in Hounsfield units (HU) or a normalized scale (e.g., 0.8 on a scale of 0 to 1).

T (Type): The type of calcification (e.g., microcalcification, macrocalcification). Value: Encoded as categorical variables (e.g., 0 for microcalcification, 1 for macrocalcification).

L (Location): The anatomical location of the calcification. Value: Encoded as coordinates or regions (e.g., [x, y] coordinates in the image or specific quadrant in the breast).

V (Volume): The volume of the calcified area. Value: Measured in cubic millimeters (e.g., 1.2 $mm^3$).

G (Growth Rate): The rate of growth of the calcification if prior imaging data is available. Value: Measured as a percentage change over time (e.g., 15% increase over 6 months).

C (Cluster Pattern): The pattern of calcification clustering. Value: Encoded as categorical variables (e.g., 0 for diffuse, 1 for clustered, 2 for linear).

A calcification vector with specific values: C=[2.5, 0.8, 0, [120, 85],1.2,15,1]

S (Size): 2.5 mm; D (Density): 0.8 (on a normalized scale); T (Type): 0 (microcalcification); L (Location): Coordinates [120, 85] in the image; V (Volume): 1.2 $mm^3$; G (Growth Rate): 15% increase over 6 months; C (Cluster Pattern): 1 (clustered)

Usage in Machine Learning

This calcification vector can be further used as an input to a machine learning model for various tasks, such as:

Classification: Determining whether the calcification is benign or malignant.

Risk Prediction: Assessing the risk of developing breast cancer.

Pattern Recognition: Identifying specific calcification patterns associated with different pathologies.

In an embodiment, the calcification vector can be further used as an input to a machine learning model along with other inputs such as clinical data, medical data, genetic data, SDOH data, demographics data etc.

Clinical Application: In a clinical setting, a radiologist might use software that extracts these features automatically from images of organs, for example, mammogram images. The calcification vectors can then be analyzed to support diagnostic decisions, monitor changes over time, and personalize patient treatment plans based on the identified patterns and risk factors.

This structured approach to representing calcifications allows for more precise and consistent analysis, leveraging the power of AI and machine learning to enhance diagnostic accuracy and patient outcomes.

Augmenting or Embedding Other Patient Data:

To enhance the calcification vector with genetic and clinical data, additional attributes can be included. This augmented vector provides a more comprehensive representation of the patient's condition, enabling more accurate analysis and personalized care.

Augmented Calcification Vector: An augmented calcification vector A may be defined for example as A=[S,D,T, L,V,G,C,Gene,CRP,CA15-3,Cpk,Age,BMI,FamilyHistory].

Where: S (Size): Size of the calcification (mm); D (Density): Density of the calcification; T (Type): Type of calcification (e.g., microcalcification, macrocalcification); L (Location): Anatomical location of the calcification; V (Volume): Volume of the calcified area ($mm^3$); G (Growth Rate): Growth rate of the calcification (% change over time); C (Cluster Pattern): Pattern of calcification clustering; Gene: Genetic markers or mutations (e.g., BRCA1/BRCA2 status); CRP: C-reactive protein level (mg/L); CA15-3: Cancer antigen 15-3 level (U/mL); Cpk: Creatine phosphokinase level (U/L); Age: Age of the patient (years); BMI: Body mass index ($kg/m^2$); FamilyHistory: Presence of family history of related conditions (e.g., breast cancer);

Example Vectors

Example 1

$$A1 = [2.5, 0.8, 0, [120, 85], 1.2, 15, 1, BRCA1+, 3.5, 25.4, 120, 45, 23.5, \text{Yes}]$$

S (Size): 2.5 mm; D (Density): 0.8 (normalized scale); T (Type): 0 (microcalcification); L (Location): Coordinates [120, 85]; V (Volume): 1.2 $mm^3$; G (Growth Rate): 15% increase over 6 months; C (Cluster Pattern): 1 (clustered); Gene: BRCA1 positive; CRP: 3.5 mg/L; CA15-3: 25.4 U/mL; Cpk: 120 U/L; Age: 45 years; BMI: 23.5 $kg/m^2$; FamilyHistory: Yes (family history of breast cancer)

Example 2

$$A2 = [3.0, 0.9, 1, [150, 95], 2.0, 20, 2, BRCA2-, 2.0, 18.6, 110, 52, 27.8, \text{No}]$$

S (Size): 3.0 mm; D (Density): 0.9 (normalized scale); T (Type): 1 (macrocalcification); L (Location): Coordinates [150, 95]; V (Volume): 2.0 $mm^3$; G (Growth Rate): 20% increase over 6 months; C (Cluster Pattern): 2 (linear); Gene: BRCA2 negative; CRP: 2.0 mg/L; CA15-3: 18.6 U/mL; Cpk: 110 U/L; Age: 52 years; BMI: 27.8 $kg/m^2$; FamilyHistory: No Clinical Relevance These augmented vectors provide a multi-faceted view of the patient's condition, integrating calcification characteristics with genetic and clinical data. This holistic approach enhances the precision of diagnostic and prognostic assessments, enabling more tailored and effective treatment plans. For example: Vector A1 might indicate a higher risk of breast cancer due to the presence of BRCA1 mutation and elevated CA15-3 levels, necessitating more aggressive monitoring and intervention. Vector A2 with BRCA2 negative status and lower CA15-3 levels, might suggest a lower immediate risk but still requires regular surveillance due to the presence of macrocalcifications and moderate CRP levels. By embedding genetic and clinical data into calcification vectors, AI models can derive deeper insights, leading to improved patient outcomes.

In an embodiment, the vector comprises a calcification vector derived from the image analysis and patient data comprising genetic data, clinical data, medical data, treatment phase, medication, treatment schedule, etc.

Technical Result:

Technical results demonstrate that the integrated diagnostic platform significantly enhances the accuracy of breast cancer detection and also provides a comprehensive health risk profile for related risks for each patient. Clinical trials indicate an increased accuracy in early cancer detection rates and an improvement in identifying patients at high risk for other health conditions. These advancements facilitate more personalized treatment plans and proactive health management strategies.

Technical Details Specific to the Technical Solution:

The technical details of the specific solution involve the implementation of convolutional neural networks (CNNs) for image analysis, natural language processing (NLP) for EHR data extraction, and federated learning techniques to ensure data privacy and security. The system architecture includes a central AI engine that integrates and processes multi-modal data inputs, generating a unified health report that highlights both cancer indicators and other significant health risks. The AI algorithms are trained on extensive datasets, ensuring robustness and reliability in diverse clinical settings.

FIG. 2 shows detailed input vectors and the output risk predictions for multiple organs according to an embodiment. The BRICC-G (Breast Risk Indicator for Calcification and Cancer—General) scoring system is designed to provide a comprehensive evaluation of calcification patterns and associated clinical risks using a combination of image analysis, genetic, clinical, and medical data. This system leverages multiple machine learning models to generate detailed assessments, which are then stratified into actionable outcomes.

Information L1 to L5 provides foundational information categorized into five levels, each representing different data layers or specific insights derived from the analysis.

Sub score range 0 to 1 or any other predefined scoring range and associated risk level, and the stratification is based on a sub score range, allowing for a refined assessment of various parameters.

Assessment and Management comprises assessing the risk for various organs and conditions as shown and further comprises evaluation and management plans derived from the analysis data. It further comprises personalized patient management plans.

Score represents the quantified output based on the assessment, the first level indicates grouping based on risk to various organs (BIC-V) and grouping based on organ biology for response of the disease/treatment (BIC-B).

Ground Truth (clinical fact validation) ensures the scores and outcomes are validated against clinical facts, ensuring reliability and accuracy.

Details on Machine Learning Models and their Outcomes:
Model 1: Image Analysis Deep Learning Models Consortium of Image Analysis DL Models: Utilized for identification and quantification of mammograms, focusing on parameters like location, spread, nature, shape, size, density, anatomy, distribution, involvement, continuity, etiology, and characterization. The outcome of this phase is a quantified calcification vector with elements (scores) for each parameter mentioned above.

Augmented Calcification Vector comprises embedding or augmenting calcification vector information with genetic, clinical, and medical lab data to estimate the score BIC-V and BIC-B.

Consortium of Assessment ML Models take the input of augmented calcification vectors and generate 16 outcomes, each from an individual model or a group of outputs from a single model. In an embodiment, the augmented calcification vector can be further augmented with a calcification vector from a specific organ for which the risk prediction is being made. In an embodiment, the first calcification vector may be specific to the organ for which the risk is being predicted. In another embodiment, the calcification vector may be an augmented calcification vector from various images formed from various organs.

Statistical Models compute BIC-V & BIC-B, which feed into the comprehensive BRICC-G score. BIC-V and BIC-B are sub scores for a group of computed individual risks. The BRICC-G scoring system employs a variety of statistical models to consolidate individual risk scores from multiple domains, such as breast cancer, cardiovascular health, and other organ-specific risks, into a single comprehensive risk score. The individual models involved in determining risk for each organ comprise one or more of logistic regression, survival analysis, Bayesian networks, and ensemble learning models. An example explanation of these models and their roles in the BRICC-G framework is as follows:

Logistic Regression: In an embodiment, to predict the probability of a patient developing a specific condition, such as breast cancer or cardiovascular disease, based on the input variables.

Breast Cancer Risk: Logistic regression models use variables like calcification characteristics, genetic markers, and clinical data to estimate the probability of breast cancer occurrence.

Example $$\text{Probability (Breast Cancer)} = x = \frac{1}{1 + e^{-(\beta 0 + \beta 1 \times Size + \beta 2 \times Density + \cdots + \beta n \times Genetic\ Marker)}}$$

Cardiovascular Risk: Separate logistic regression models predict the likelihood of cardiovascular events using cardiac-specific imaging results, lab markers, and clinical history.

Survival Analysis estimates the time until an event of interest (e.g., cancer relapse or survival) occurs.

Relapse Prediction: Kaplan-Meier curves and Cox proportional hazards models are used to estimate the time to cancer relapse based on patient-specific factors.

Overall Survival: These models also predict overall survival times, incorporating data such as treatment history, tumor characteristics, and patient demographics.

Example $$h(t) = h_0(t) \times e^{(\beta 1 \times \text{Treatment History} + \beta 2 \times \text{Tumor Grade} + \cdots + \beta n \times \text{Age})}$$

where h(t) is the hazard function, and $h_0(t)$ is the baseline hazard.

Bayesian Networks may be used to model the probabilistic relationships between multiple variables and predict outcomes based on these interdependencies.

Multi-organ Risk Assessment: Bayesian networks integrate various risk factors across different organs (e.g., breast, cardiovascular, renal) to provide a holistic risk profile.

Conditional Probabilities: These models compute the conditional probabilities of developing secondary conditions based on the presence of primary conditions.

Example $$P(\text{Cardiovascular Risk}|\text{Breast Cancer Risk, Calcification, Genetics, Clinical Data}) = \frac{P(\text{Breast Cancer Risk, Calcification, Genetics, Clinical Data})}{P(\text{Cardiovascular Risk, Breast Cancer Risk, Calcification, Genetics, Clinical Data}}$$

Ensemble Learning Models combine predictions from multiple models to improve accuracy and robustness. These are used in Risk Score Consolidation. For example, ensemble methods like random forests, gradient boosting machines, and stacking are used to aggregate individual risk scores, and aggregate them into sub scores BIC-V, BIC- and finally into a single BRICC-G score.

Weighted Averaging: These models assign weights to different risk scores based on their predictive power and reliability.

Example $$BRICC{-}G\ \text{Score} = w_1 \times BIC{-}V + w_2 \times BIC{-}B + w_3 \times CardiovascularRisk + \cdots + w_n \times \text{Chronic Disease Risk}$$

where $w_i$ are the weights assigned to each component risk score.

Consolidation Process for BRICC-G Score:
Individual Risk Calculation:

Breast Cancer Risk: May be calculated using logistic regression and survival analysis or any other ML/deep learning model.

Healing and Biological Risk: Derived from survival analysis and logistic regression focusing on healing time and tumor characteristics.

Cardiovascular Risk: Estimated using logistic regression and Bayesian networks.

Other Organ Risks: Assessed using Bayesian networks and ensemble models or each organ may have an independent ML model that is best suitable for predicting the risk.

Weight Assignment: Weights are assigned to each risk score based on the model's performance metrics (e.g., Area Under the Receiver Operating Characteristic Curve AUC-ROC for logistic regression, concordance index for survival analysis).

Risk Score Aggregation: An ensemble learning model (e.g., stacking) integrates these weighted risk scores into a single BRICC-G score, reflecting the overall risk to the patient.

Final Score Interpretation: The consolidated BRICC-G score provides a comprehensive risk assessment, guiding clinical decisions and personalized treatment plans.

One or more ML models are configured for specific clinical assessments as follows:

BIC-V Cardiovascular: Evaluation of cardiovascular health using cardiac-specific imaging like ECHO, MRI, CT angiograms, and Holter test results.

Cardiac Contractile and Rhythm: Assesses cardiac contractile function and rhythm disturbances.

Renovascular & Renal Perfusion: Evaluates kidneys and associated blood vessels using renal function tests, renal Doppler, and angiography.

Retinopathy: Assesses retinal health using retinal evaluations and neuroimaging (MRI of the brain).

Pancreatic: Evaluates pancreatic diseases or cancer using imaging techniques like Endoscopic retrograde cholangiopancreatography (ERCP), Magnetic resonance cholangiopancreatography (MRCP), Magnetic resonance imaging/computed tomography (MRI/CT) scans.

Cerebrovascular and CNS: Assesses neurological and cerebrovascular health using brain imaging (MRI, EEG, MMS).

Pulmonary/COPD: Evaluates lung function and COPD using pulmonary imaging (CT chest) and functional tests (DLCO).

Chronic Disease: Clinical evaluation for subsequent development of chronic disease conditions.

Critical Vascular Perfusion: Assesses the vascular system's ability to deliver adequate blood flow to various organs and tissues using specific serum markers and imaging.

Healing: Evaluates organ biology and healing time.

Tumor Flow and Growth: Assesses tumor flow and growth using Ki-67 index/grade, vascularity, LVI (Lymphovascular invasion), PNI (Perineural invasion), and morphology.

Inflammation/Degeneration: Evaluates the development or association with chronic inflammatory conditions like arthritis, IBD, RA, SLE, autoimmune disorders, etc.

Relapse: Monitors overall survival, progression-free survival, and tumor-free period.

Adverse Events: Evaluates quality of life (QOL) scores, TWISTT scores, and the incidence and prevalence of CTC adverse events.

Clinical Response: Assesses clinical response using PET CT, RECIST criteria, serum markers, clinical improvement, and pathological response.

BRICC-G Score/Comprehensive Score: Combines the outcomes of the above assessments to provide a BRICC-G score, guiding clinical decisions and patient management. The BRICC-G scoring system provides a holistic approach to evaluating calcification and associated risks by integrating detailed image analysis with genetic, clinical, and medical data. This comprehensive approach enhances the accuracy of predictions related to breast cancer, pancreatic health, cardiovascular health, tumor growth, inflammation, relapse, and clinical response, thereby improving patient care and treatment outcomes.

Figure 3:
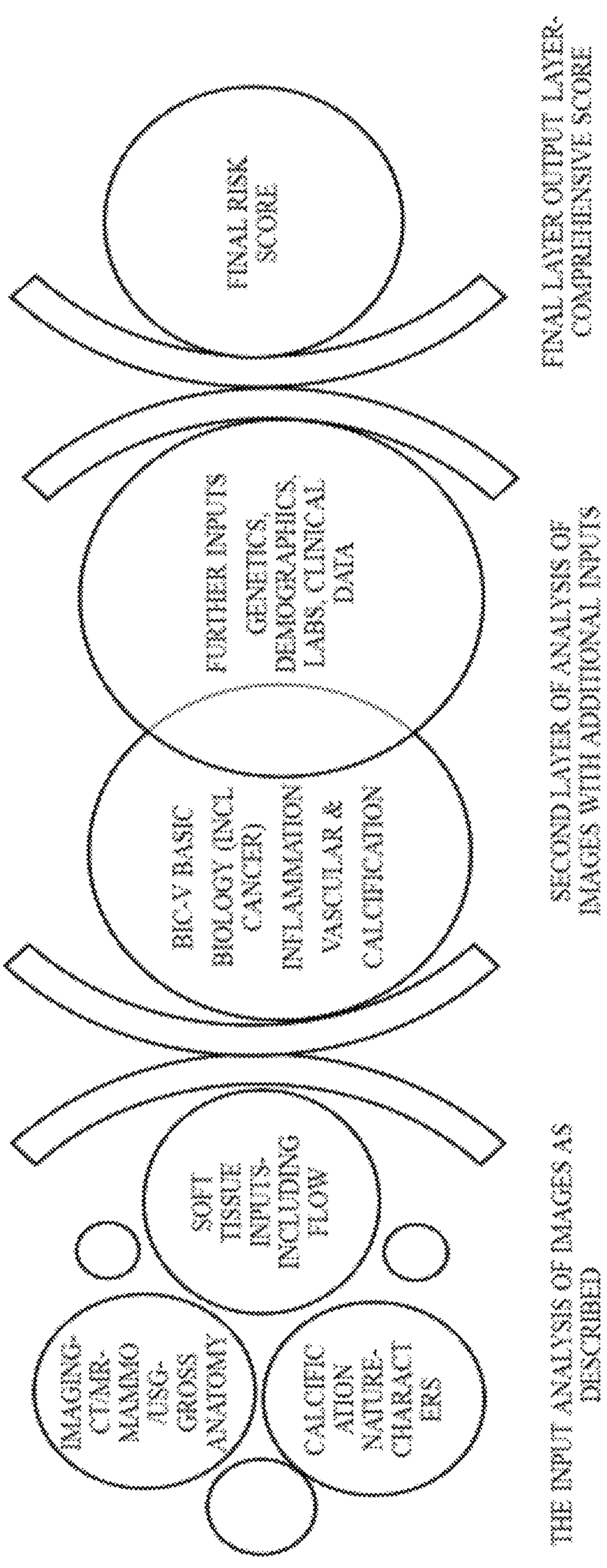
FIG. 3 shows the multi-level or multi-layer approach involved in predicting the risk scores according to an embodiment.

FIG. 3 shows the multi-level or multi-layer approach involved in predicting the risk scores according to an embodiment. The figure illustrates a multi-layered process for consolidating various medical and biological inputs to generate a final risk score, particularly in the context of breast cancer and associated risks.

First Layer comprises a first bubble indicating basic imaging inputs from CT/MRI/MAMMO/USG capturing GROSS ANATOMY. This bubble represents the imaging techniques used to gather anatomical data. These modalities provide the foundational visual inputs needed for further analysis; a second bubble indicates the input related to soft tissue characteristics and blood flow patterns, which are evaluated for understanding the vascular and soft tissue environment; and a third bubble focuses on the specific nature and characteristics of calcifications observed in the images, including aspects such as location, spread, shape, size, and density.

Second layer is concentrated on BIC-V Basic Biology. BIC-V basic biology (including cancer) inflammation vascular and calcification consolidates the biological factors, including cancer biology, inflammation status, vascular health, and detailed calcification characteristics. This layer builds on the basic imaging inputs to form a more detailed biological and pathological profile.

Second layer comprises a second bubble with further input integration. Further inputs comprise genetics, demographics, labs, clinical data. This bubble represents the integration of additional comprehensive data, including genetic information, demographic details, laboratory results, and broader clinical data. This layer enhances the understanding derived from basic biology by incorporating patient-specific and holistic health data.

Third Layer for determining final risk score. The bubble signifies the culmination of all the integrated data, evaluation of various risks and finally consolidating into a final risk score. This final risk score represents the overall risk assessment, from the inputs synthesized from imaging, biology, genetics, demographics, labs, and clinical data. The figure depicts a structured, hierarchical approach to risk assessment, starting from raw imaging data and progressively integrating more detailed biological, genetic, and clinical information. Each layer builds upon the previous one, leading to a comprehensive final risk score that can guide clinical decision-making and patient management.

The multi-layered approach to risk assessment is for evaluating not just cancer risk but also risks to other organs and overall patient health and demonstrates an application of AI technology in healthcare to improve the patient outcome. The system is enabled to integrate various types of data and generate comprehensive health scores (e.g., BRICC-G score) using AI in the domain of medical diagnostics. The method by which the system combines image data, genetic information, and clinical data to provide a holistic health assessment adds uniqueness. Further, the system outputs, i.e., specific risk scores for one or more organs and conditions along with the BRICC-G score. These scores are specific and quantifiable results that are directly used on informed clinical decisions. The generation of outputs through a unique combination of data inputs and AI processing introduces an inventive concept. The specificity and utility of these outputs or quantified risks in a clinical setting further supports the physicians in treatment planning. The AI model based on a neural network and training data is used for diagnosing a risk of one or more organ diseases from a trained list of organs related risks (one or more organs, and one or more risks related to each organ. A neural network model is trained using a plurality of training datasets, each comprising parameters and at least one indicator of the disease for an organ associated with a respective patient, and wherein each training dataset is associated with a respective organ disease selected from a group of organs and organ diseases (risks). The model contributes towards improved and specific diagnostic process for plurality of risks for patients.

Figure 4:
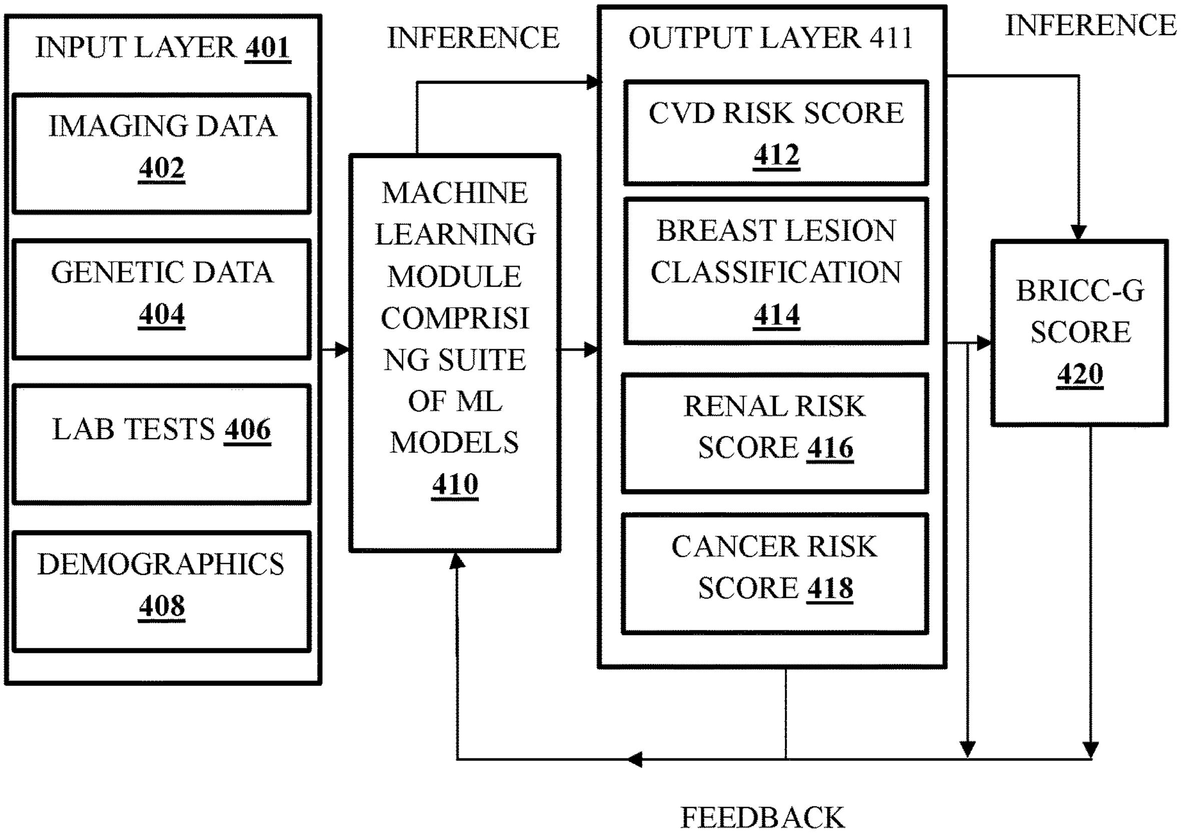
FIG. 4 shows the system with inputs and outputs according to an embodiment.

FIG. 4 shows the system with inputs and outputs according to an embodiment. FIG. 4 illustrates a structured methodology for determining the BRICC-G score, which is a comprehensive risk assessment metric derived from various medical and clinical inputs. The figure comprises the input parameters, the ML models used at arriving at the risk scores, the output layer comprising individual risk scores, and the final consolidated score. The process may comprise intermediate scores at individual organ levels, and a consolidated group level score.

Input Parameters: The input layer 401 comprises Input parameters. The input parameters comprise imaging data 402, genetic data 404, laboratory tests 406, demographics 408, clinical history, and may include any other relevant medical data.

The system further comprises a preprocessing module configured to prepare the raw data for analysis by performing necessary preprocessing tasks. It comprises of two parallel systems:

Data Preprocessing System: This system cleans and organizes the clinical and medical data, ensuring consistency and accuracy. It handles tasks such as data normalization, standardization, and dealing with missing values.

Image Processing System: This system processes the images of the organ, for example breast, extracting important features and ensuring the images are in a suitable format for analysis.

It might involve image enhancement, segmentation, and feature extraction.

Machine Learning Models: The system comprises a Machine learning module comprising a suite of ML models 410 computational, statistical, and/or analytical models that are used to integrate the various input parameters/features and provide output parameters. The models apply statistical models, or machine learning techniques to form correlations and patterns for the input data and the output data and to provide a comprehensive assessment. The integration process combines information from different sources to produce a unified evaluation of the patient's risk profile or features of the patient record data.

In an embodiment, the system is configured to build AI Model(s) and train them with the patient data. The feature vectors are used to train AI models. Various machine learning techniques and algorithms are applied to build models that can analyze the data and identify patterns, make predictions, or classify information. It involves selecting the appropriate algorithms, training the models on the data, and validating their performance to ensure they provide accurate and reliable results.

AI powered System for assessment and monitoring of cancer and cardio and vascular risk or A1 system for organ risk prediction identifies the patients at risk in an early stage. Machine learning based AI models were developed to identify and capture patterns in patient data and the image data. The AI system for organ risk prediction utilizes a comprehensive set of inputs, including patients' image data of the organ, medical, socioeconomic characteristics. The outputs of these models include scores for the likelihood of cancer or organ related risks. The machine learning techniques employed to identify these patterns include logistic regression, support vector machines (SVM), K-nearest neighbor, decision trees, and ensemble methods.

To achieve these outputs, various machine learning techniques are employed:

Logistic Regression: This model is ideal for binary classification problems, making it suitable for predicting the likelihood of risk to one or more organs. By analyzing the relationship between multiple independent variables (e.g., medical image data, clinical data, lifestyle factors, etc.) and the binary outcome (having organ risk/cancer or not), logistic regression can estimate the probability of cancer given the set of inputs.

Support Vector Machines (SVM): SVMs are effective in high-dimensional spaces and are used for both classification and regression tasks. For cancer or organ risk prediction, SVMs help classify patients into different risk categories based on their input data comprising images, medical, clinical, and lifestyle data. By finding the optimal hyperplane that separates the data into different classes, SVMs can accurately predict the likelihood of cancer and related risks to the organ or other organs.

K-Nearest Neighbor (KNN): This algorithm classifies data points based on the closest training examples in the feature space. For example, for breast cancer, cardio and vascular risk, and other organ risk prediction, KNN classifies patients by comparing their data to the most similar historical cases. This method is particularly useful for identifying patterns in patients with similar characteristics and predicting the risk of cancer to one or more organs given the set of inputs.

Decision Trees: Decision trees model decisions and their possible consequences, creating a tree-like structure of decisions. For predicting the risk to one or more organs given a patient record, decision trees map out potential outcomes based on various patient characteristics. Each node in the tree represents a feature (e.g., calcification, calcification pattern, genetic marker features, clinical data features etc.), each branch represents a decision rule, and each leaf represents an outcome (e.g., likelihood of breast cancer, likelihood of cardio risk, likelihood of pancreatic risk etc.).

Ensemble Methods: Ensemble methods combine the predictions of multiple models to improve accuracy and robustness. Examples include Random Forests and Gradient Boosting Machines (GBM). By aggregating the predictions of several decision trees (as in Random Forests) or sequentially improving the model (as in GBM), ensemble methods enhance predictive performance and reduce the risk of overfitting. For one or more organ risk prediction, ensemble methods provide a more comprehensive assessment by leveraging the strengths of different models. In an embodiment, each method can provide various outputs and each method, and each output of the method, can be weighted before the results are ensembled into one single prediction result for each risk predicted/detected.

In an embodiment, various ensemble methods used include bagging, boosting, stacking, voting, and blending. Bagging, exemplified by Random Forest, involves training multiple instances of the same model on different subsets of the training data and combining their predictions. Boosting, used in algorithms like AdaBoost and XGBoost, sequentially builds models that correct the errors of their predecessors, with final predictions being a weighted combination of all models. Stacking performs training multiple base models, using their predictions as inputs to a higher-level meta-model for the final prediction. Voting combines predictions from multiple models by majority vote or averaging. Blending, similar to stacking but simpler, uses a holdout validation set for training the meta-model. These ensemble methods are powerful tools for reducing overfitting and variance, leading to better generalization on unseen data and improving predictive performance in real-world applications. These models are integrated, and the AI system can provide assessments, enabling physicians to implement targeted and personalized intervention strategies for cancer or health management.

In an embodiment, AI models are constructed by training the models with the data and are configured to take the data from a patient record and predict the likelihood of risk to one or more organs, and stratify them into predefined categories, for example high, medium, and low.

In an embodiment, an outcome of the AI model provides insights on contributing risk factors for better management of condition across different cohorts along with risk level.

In an embodiment, more than one AI model for each risk may be considered with appropriate weights on each model's output as well as individual outputs and a result arrived from a weighted average of these models.

In an embodiment, Genetic Algorithms may be utilized to determine the best performing model given various performance criteria for the model, for example prediction accuracy, precision, recall, F1 score, etc. Genetic algorithms (GAs) are a class of optimization techniques inspired by the principles of natural selection and genetics, and they can be effectively used in the selection and optimization of AI models for comprehensive risk prediction for one or more organs. The process begins with the initialization of a population of candidate models, each represented by a set of parameters and hyperparameters encoded as chromosomes. These initial models can be various types of algorithms, such as Logistic Regression, Support Vector Machines (SVM), K-Nearest Neighbors (KNN), Decision Trees, and ensemble methods like Random Forest and Gradient Boosting. The genetic algorithm then iteratively evolves this population to improve model performance. Each iteration, or generation, involves several steps. First, models are evaluated based on a fitness function, which typically measures performance metrics such as accuracy, precision, recall, or Area Under the Curve-Receiver Operating Characteristic (AUC-ROC) on a validation dataset. The best-performing models are selected to contribute to the next generation. Next, pairs of selected models are combined to create offspring models by exchanging segments of their chromosomes in a process known as crossover. This simulates the biological crossover process and allows new models to inherit features from multiple parent models, potentially leading to better performance. Then, random changes are introduced to the offspring models' chromosomes through mutation, maintaining genetic diversity within the population and exploring new regions of the solution space to prevent premature convergence to suboptimal solutions. Finally, the new generation of models replaces the old ones, and the process repeats until a predefined stopping criterion is met, such as a maximum number of generations or a satisfactory level of performance.

Training AI/ML models: In an embodiment, a first machine learning model is trained using the breast image data and supplementary data to predict the likelihood of breast cancer; a second machine learning model is trained using the breast image data and supplementary data to predict the cardiovascular risk and cardiac contractile risk; a third machine learning model is trained using the breast image data and supplementary data to predict the renal and blood vessel risk; a fourth machine learning model is trained using the breast image data and supplementary data to predict the retina risk; a fifth machine learning model is trained using the breast image data and supplementary data to predict the pancreatic risk; a sixth machine learning model is trained using the breast image data and supplementary data to predict the neurological and cerebrovascular risk; a seventh machine learning model is trained using the breast image data and supplementary data to predict the pulmonary and COPD risk; an eight machine learning model is trained using the breast image data and supplementary data to predict the chronic disease risk; a ninth machine learning model is trained using the breast image data and supplementary data to predict the critical vascular perfusion risk. The machine learning models in each of the cases can be different or the same for a group of cases or can be an ensemble method for each of the cases or group of cases. Supplementary data comprises clinical data, medical data, genetic data, lifestyle data, SDOH, and additional image scans of the organ whose risk is being determined.

In an embodiment, the system further provides comprehensive insights of a patient's key health indicators with respect to a diagnosis/treatment, wherein comprehensive insights comprise a mapping of outputs of the model to the input factors or features which explain the factors contributing to the risks and their percentage contribution.

Intermediate Outputs: The system evaluates and determines intermediate outputs, or sub-scores generated during the calculation process in the output layer 411. These sub-scores comprise specific risk assessments for different health conditions or aspects, such as cardiovascular risk score 412, breast lesion classification 414, renal risk score 416, cancer risk score 418, inflammation levels, or other organ-specific risks. Each sub-score provides detailed insights into various components of the patient's health, contributing to the final risk score. Though only certain elements are shown in the output layer, a comprehensive list of organ and risk scores/risks is provided in FIG. 2.

Final Output: BRICC-G Score:

The system computes final output and is provided as BRICC-G Score 420 This score represents a comprehensive risk assessment that guides clinical decision-making and patient management. The BRICC-G score 420 consolidates all the intermediate sub-scores and input parameters into a single, quantifiable metric that reflects the overall health risk of the patient.

According to an embodiment, it is a system for calculating the BRICC-G score, a composite risk assessment metric. It starts with various input parameters, which are processed through ML models to produce sub-scores for one or more organs. These sub-scores are then integrated to yield the final BRICC-G score.

Inference and Feedback Loop: The figure further comprises an inference pathway where predictions and insights are generated and fed back into the system for further refinement and improvement of the AI models. This feedback loop helps in continuously improving the accuracy and reliability of the predictions by learning from new data and outcomes.

Representation Learning: Performance of the prediction model depends upon the quality of data pooled for training the model. Deep neural network models are trained to learn data representation for the data considered as the input. To improve the performance of the prediction model, vector representation can be adopted to denote the content in the medical records. Furthermore, information extracted from clinical notes and image scans are also combined with the other characteristics of the data and are represented as vectors.

Figure 5:
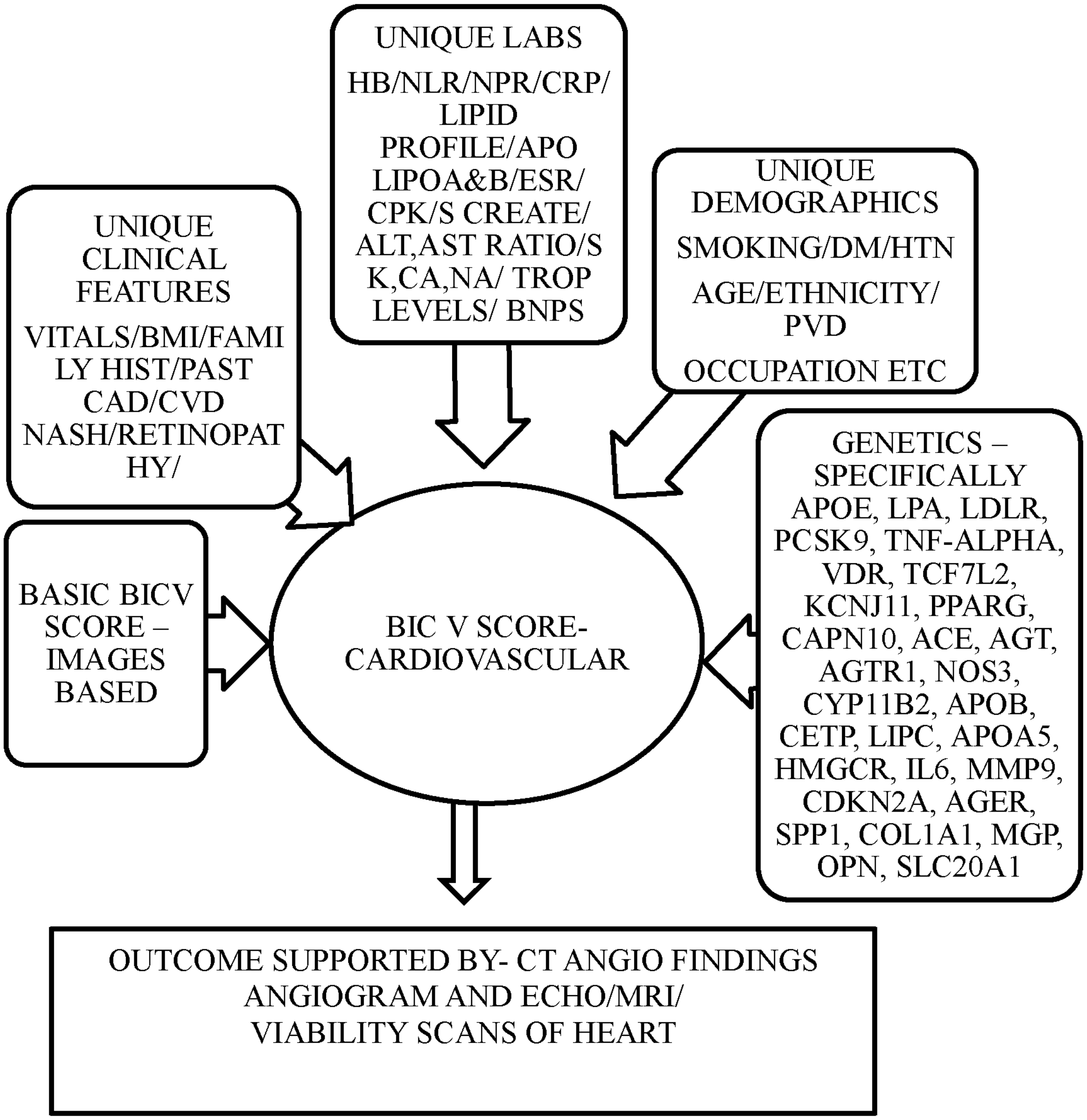
FIG. 5 shows individual level score for cardiovascular in BIC-V sub score according to an embodiment.

FIG. 5 shows individual level score for cardiovascular in BIC-V sub score according to an embodiment. According to an embodiment of the system, the system determines the cardiovascular risk by augmenting the calcification and the calcification pattern with the genetic data and the clinical data, wherein the genetic data comprises APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and the clinical data comprises vitals, BMI, family history, past CAD, CVD NASH, retinopathy, Hb, NLR, NPR, CRP, Lipid profile, APO Lipo A&B, ESR, CPK/S Create, ALT, AST ratio, S K, CA, Na, Trop levels, BNPs; and outputs a BIC-V cardiovascular risk score and a BIC-V cardiovascular risk assessment from the BIC-V cardiovascular risk score.

According to an embodiment, it is a BIC-V cardiovascular assessment method for assessing cardiovascular health using an augmented calcification vector, comprising receiving a vectorized calcification score from mammographic image data; augmenting the vector with patient specific data relevant to cardiovascular conditions which includes but not limited to genetic markers inputs comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and clinical data comprising one or more of vitals, BMI, family history, past CAD, CVD, NASH, retinopathy, Hb, NLR, NPR, CRP, Lipid profile, APO, Lipo A&B, ESR, CPK, S Create, ALT, AST ratio, S K, CA, Na, Trop levels, BNPs; employing a machine learning model to calculate a BIC-V Cardiovascular score from the augmented vector; outputting the cardiovascular health assessment for clinical use in the form of a score.

Figure 6:
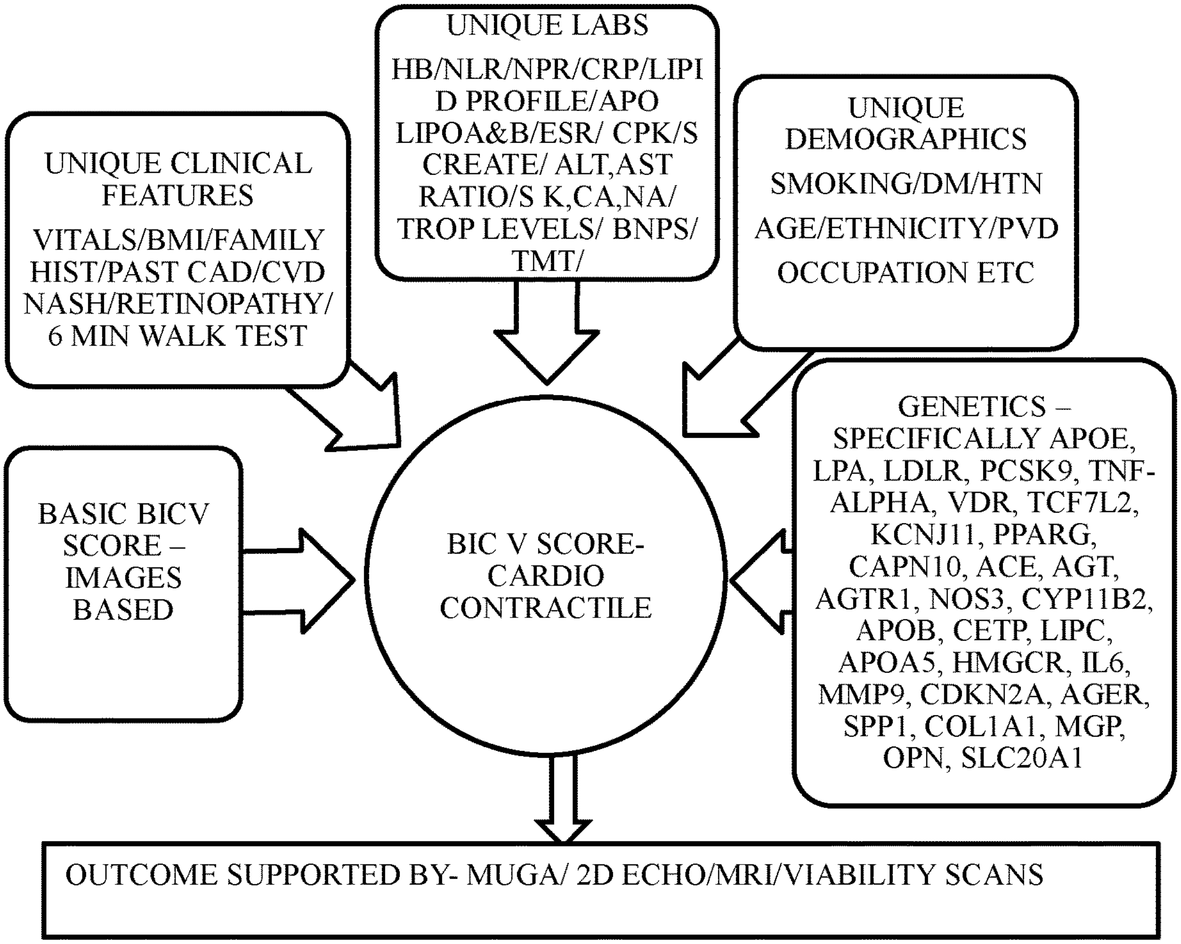
FIG. 6 shows individual level score for cardiac contractile in BIC-V sub score according to an embodiment.

FIG. 6 shows an individual level score for cardiac contractile in BIC-V sub score according to an embodiment. According to an embodiment of the system, the system determines the cardiac contractile risk by augmenting the calcification and the calcification pattern with the genetic data, the clinical data, and patient specific data relevant to myocardial health, wherein the genetic data comprises APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises vitals, BMI, family history, past CAD, CVD NASH, retinopathy, 6 minute walk test, Hb, NLR, NPR, CRP, Lipid profile, APO, Lipo A&B, ESR, CPK, S Create, ALT, AST ratio, S K, CA, Na, Trop levels, BNPs, TMT, and outputs a cardiac contractile score; and a cardiac contractile risk assessment from the cardiac contractile risk score.

According to an embodiment, it is a cardiac contractile function assessment method for evaluating cardiac contractile function, comprising obtaining a calcification vector from image analysis of cardiac structures, enhancing the vector with patient specific data relevant to myocardial health comprising genetic markers inputs comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and clinical data comprising one or more of Vitals, BMI, family history, past CAD, CVD NASH, retinopathy, 6 Min walk test; Hb, NLR, NPR, CRP, Lipid profile, APO, Lipo A&B, ESR, CPK, S Create, ALT, AST ratio, S K, CA, Na, Trop levels, BNPs, TMT; processing the enhanced vector to generate a cardiac contractile score; providing the score for managing cardiac care.

Figure 7:
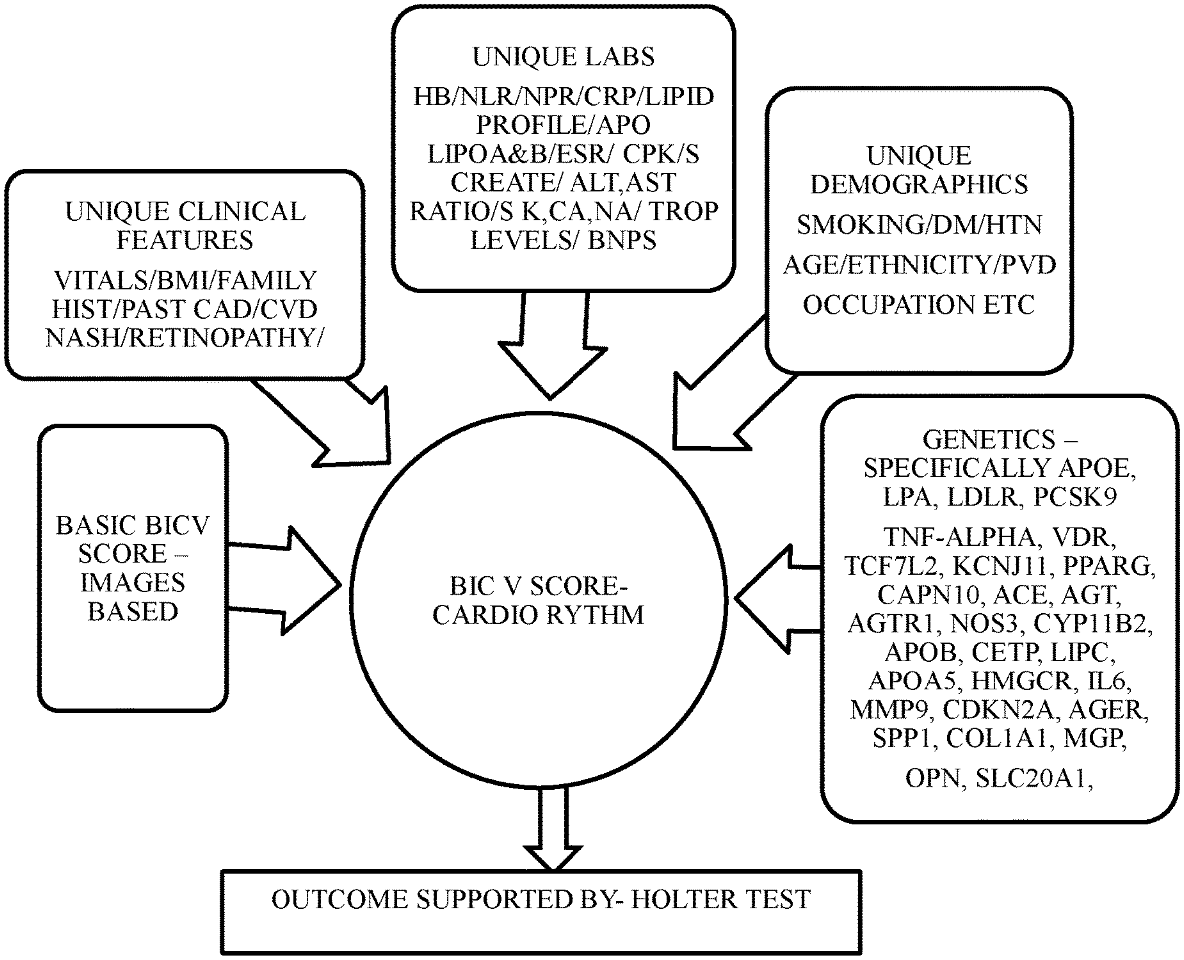
FIG. 7 shows individual level score for Cardiac rhythm in BIC-V sub score according to an embodiment.

FIG. 7 shows an individual level score for Cardiac rhythm in BIC-V sub score according to an embodiment. According to an embodiment of the system, the system determines the cardiac rhythm risk by augmenting the calcification and the calcification pattern with the genetic data, the clinical data, a classification vector indicative of electrical pathways; patient specific data with arrhythmias, wherein the genetic data APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A; and wherein the clinical data comprises vitals, BMI, family history, past CAD, CVD NASH, retinopathy, Hb, NLR, NPR, CRP, Lipid profile, APO, Lipo A&B, ESR, CPK, S Create, ALT, AST ratio, S K, CA, Na, Trop levels, BNPs, and outputs a cardiac rhythm risk score; and a cardiac rhythm risk assessment from the cardiac rhythm risk score.

According to an embodiment, it is a cardiac rhythm assessment method for cardiac rhythm diagnosis, comprising analyzing mammographic images to produce a calcification vector indicative of electrical pathways; integrating patient specific data with arrhythmias into the vector comprising genetic markers input comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; clinical data comprising one or more of Vitals, BMI, family history, past CAD, CVD NASH, retinopathy; Hb, NLR, NPR, CRP, Lipid profile, APO, Lipo A&B, ESR, CPK, S Create, ALT, AST ratio, S K, CA, Na, Trop levels, BNPs, and computing a cardiac rhythm score using a dedicated AI model.

Figure 8:
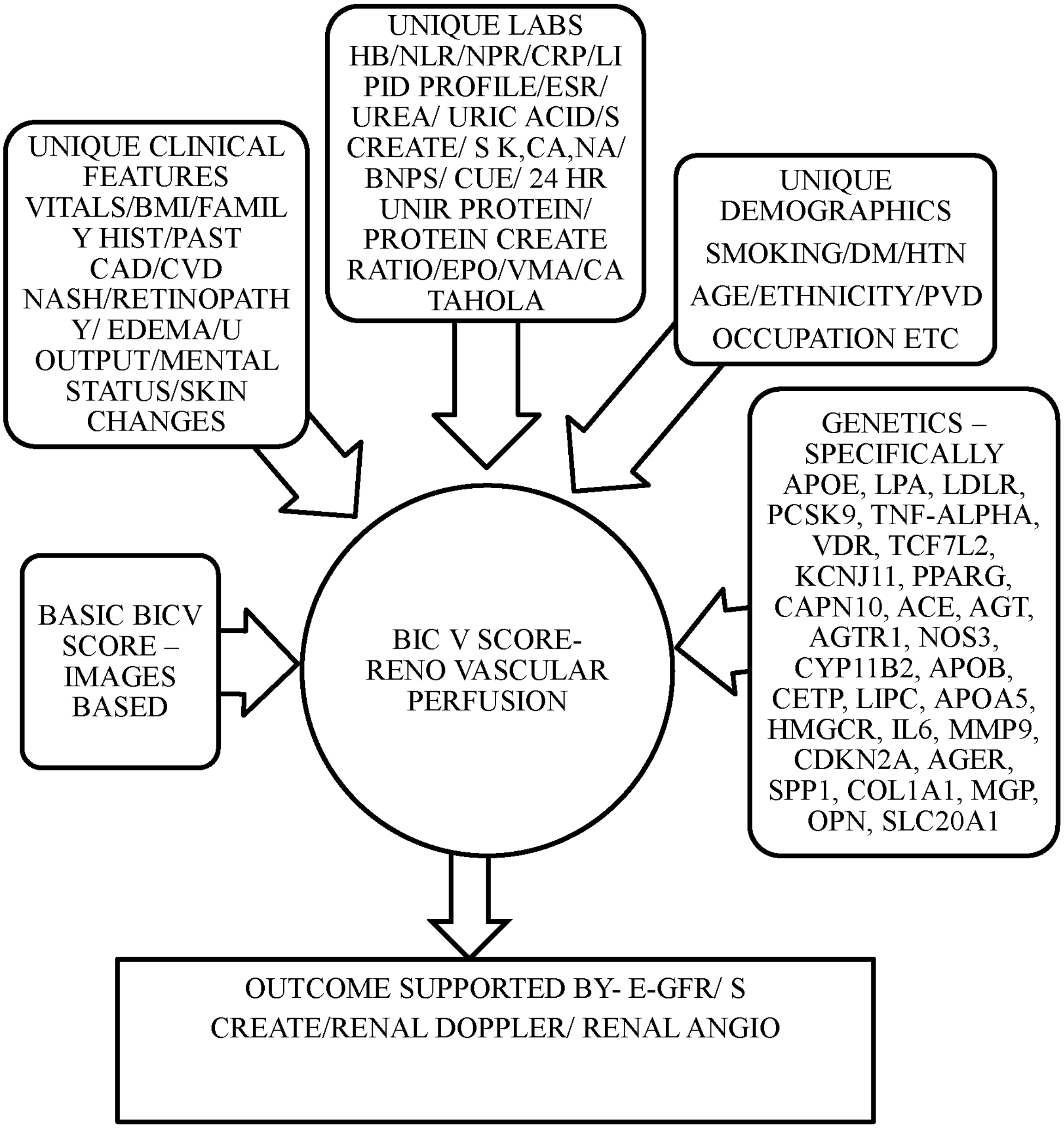
FIG. 8 shows individual level score for renovascular and renal perfusion in BIC-V sub score according to an embodiment.

FIG. 8 shows an individual level score for renovascular and renal perfusion in BIC-V sub score according to an embodiment. According to an embodiment of the system, the system determines the renovascular and renal perfusion risk by augmenting the calcification and the calcification pattern with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises vitals, BMI, family history, past CAD, CVD NASH, retinopathy, edema, U output, mental status, skin changes, Hb, NLR, NPR, CRP, Lipid profile, ESR, Urea, Uric acid, S Create, S K, CA, Na, BNPs, CUE, 24 hour urine protein, protein creatinine ratio, EPO, VMA, CAtahola; and wherein the system further determines a calcification vector from a renal image and augments the data; and outputs a renovascular and renal perfusion score and a renovascular and renal perfusion risk assessment from the renovascular and renal perfusion risk score.

According to an embodiment, it is a renovascular and renal perfusion assessment method for assessing renal perfusion, comprising deriving a calcification vector from renal imaging data; augmenting this vector with patient specific data on vascular health from clinical assessments comprising genetic markers input comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; Clinical data comprising one or more of vitals, BMI, family history, past CAD, CVD NASH, retinopathy, edema, U output, mental status, skin changes; Hb, NLR, NPR, CRP, Lipid profile, ESR, Urea, Uric acid, S Create, S K, CA, Na, BNPs, CUE, 24 hour urine protein, Protein Creatinine ratio, EPO, VMA, CAtahola; and calculating a renovascular health score through an AI-driven analysis; and employing the score to optimize renal treatment strategies.

Figure 9:
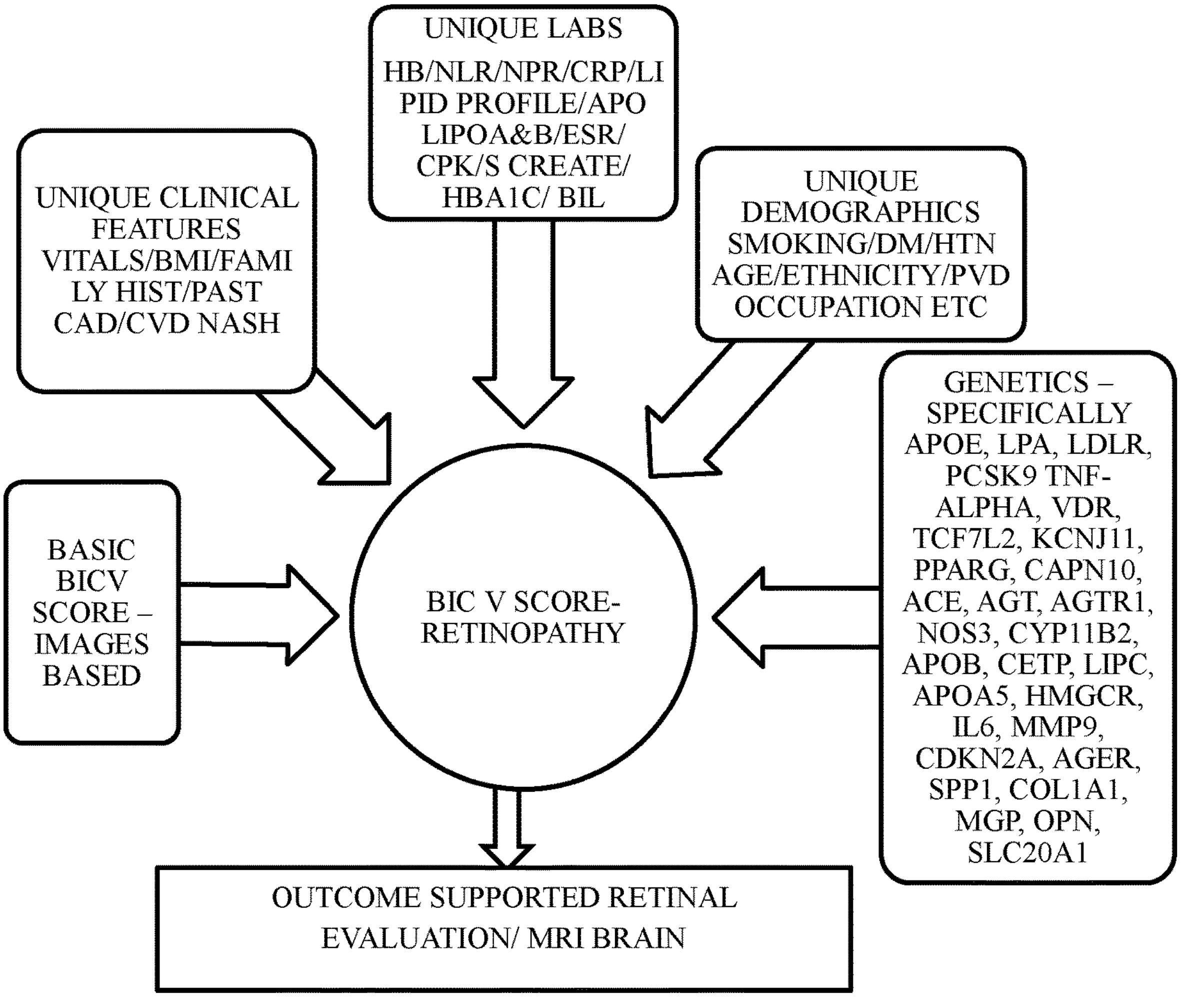
FIG. 9 shows individual level score for retinopathy in BIC-V sub score according to an embodiment.

FIG. 9 shows individual level score for retinopathy in BIC-V sub score according to an embodiment. According to an embodiment of the system, the system determines the retinopathy risk by augmenting the calcification and the calcification pattern with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises vitals, BMI, family history, past CAD, CVD NASH, Hb, NLR, NPR, CRP, Lipid profile, APO, Lipo A&B, ESR, CPK, S Create, HbA1C, Bilirubin; and wherein the system further determines a calcification vector from a retinal image and augments the data; and outputs a retinopathy risk score and a retinopathy risk assessment from the retinopathy risk score.

According to an embodiment, it is a retinopathy detection method for diagnosing retinopathy, comprising forming a calcification vector from retinal imaging; combining the vector with patient-specific data comprising genetic markers input comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; clinical data comprising one or more of Vitals, BMI, family history, past CAD, CVD NASH; Hb, NLR, NPR, CRP, Lipid profile, APO, Lipo A&B, ESR, CPK, S Create, HbA1C, Bilirubin; analyzing the composite data to compute a retinopathy score; outputting the score for ophthalmological use.

Figure 10:
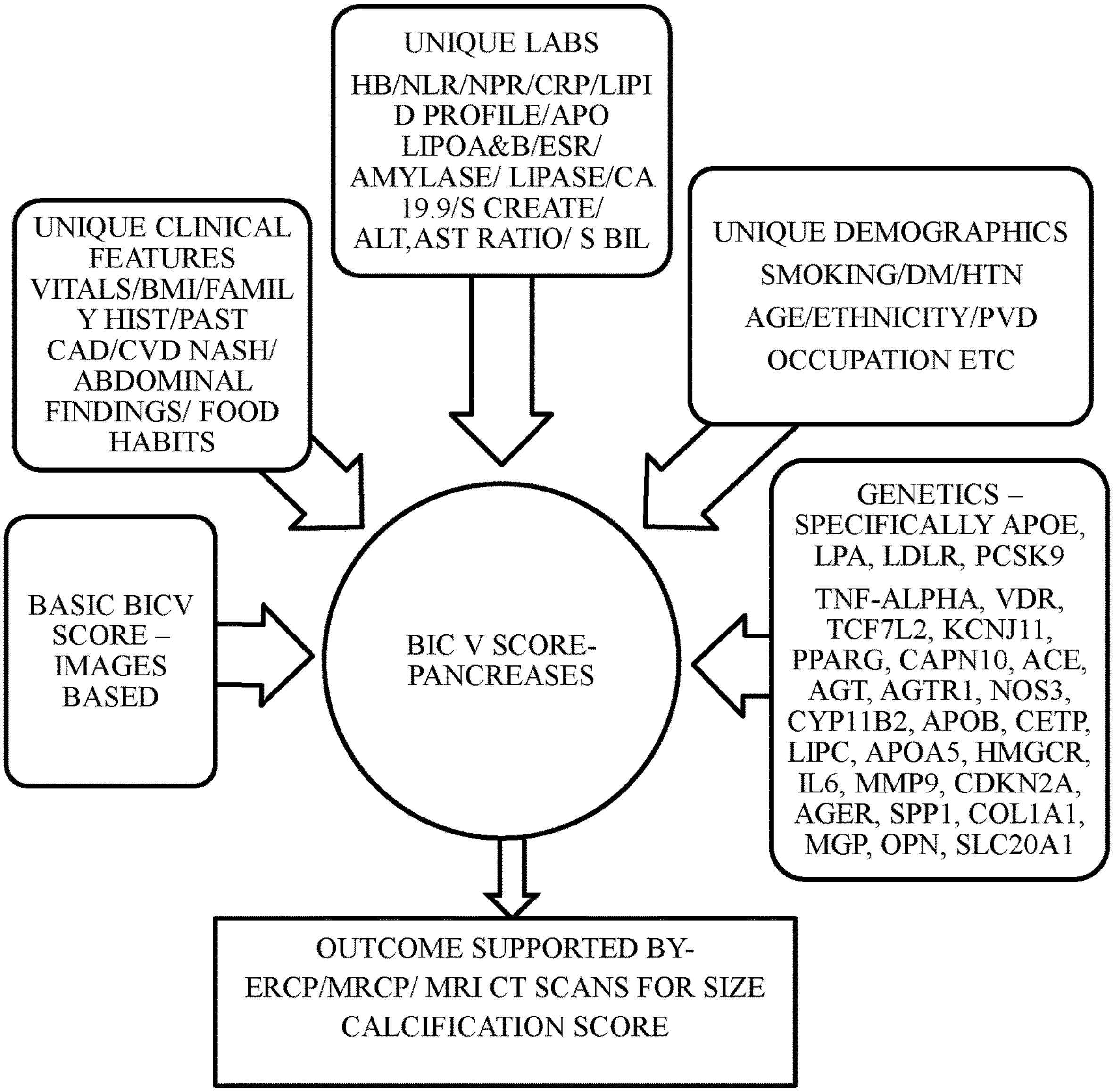
FIG. 10 shows individual level score for Pancreases in BIC-V sub score according to an embodiment.

FIG. 10 shows individual level score for Pancreases in BIC-V sub score according to an embodiment. According to an embodiment of the system, the system determines the pancreatic risk by augmenting the calcification and the calcification pattern with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises vitals, BMI, family history, past CAD, CVD NASH, abdominal findings, food habits, Hb, NLR, NPR, CRP, Lipid profile, APO, Lipo A&B, ESR, Amylase, Lipase, CA 19.9, S Create, ALT, AST ratio, S Bilirubin; and wherein the system further determines a calcification vector from a pancreatic image and augments the data; and outputs a pancreatic risk score and a pancreatic risk assessment from the pancreatic risk score.

According to an embodiment, it is a pancreatic health assessment method for evaluating pancreatic health, comprising: generating a calcification vector from pancreatic imaging studies; augmenting the vector with patient specific data linked to pancreatic diseases comprising genetic markers input comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; clinical data comprising one or more of Vitals, BMI, family history, past CAD, CVD NASH, Abdominal findings, food habits; Hb, NLR, NPR, CRP, Lipid profile, APO, Lipo A&B, ESR, Amylase, Lipase, CA 19. 9, S Create, ALT, AST ratio, S Bilirubin; and computing a pancreatic health score via machine learning algorithms; using the score for diagnostic and therapeutic purposes.

Figure 11:
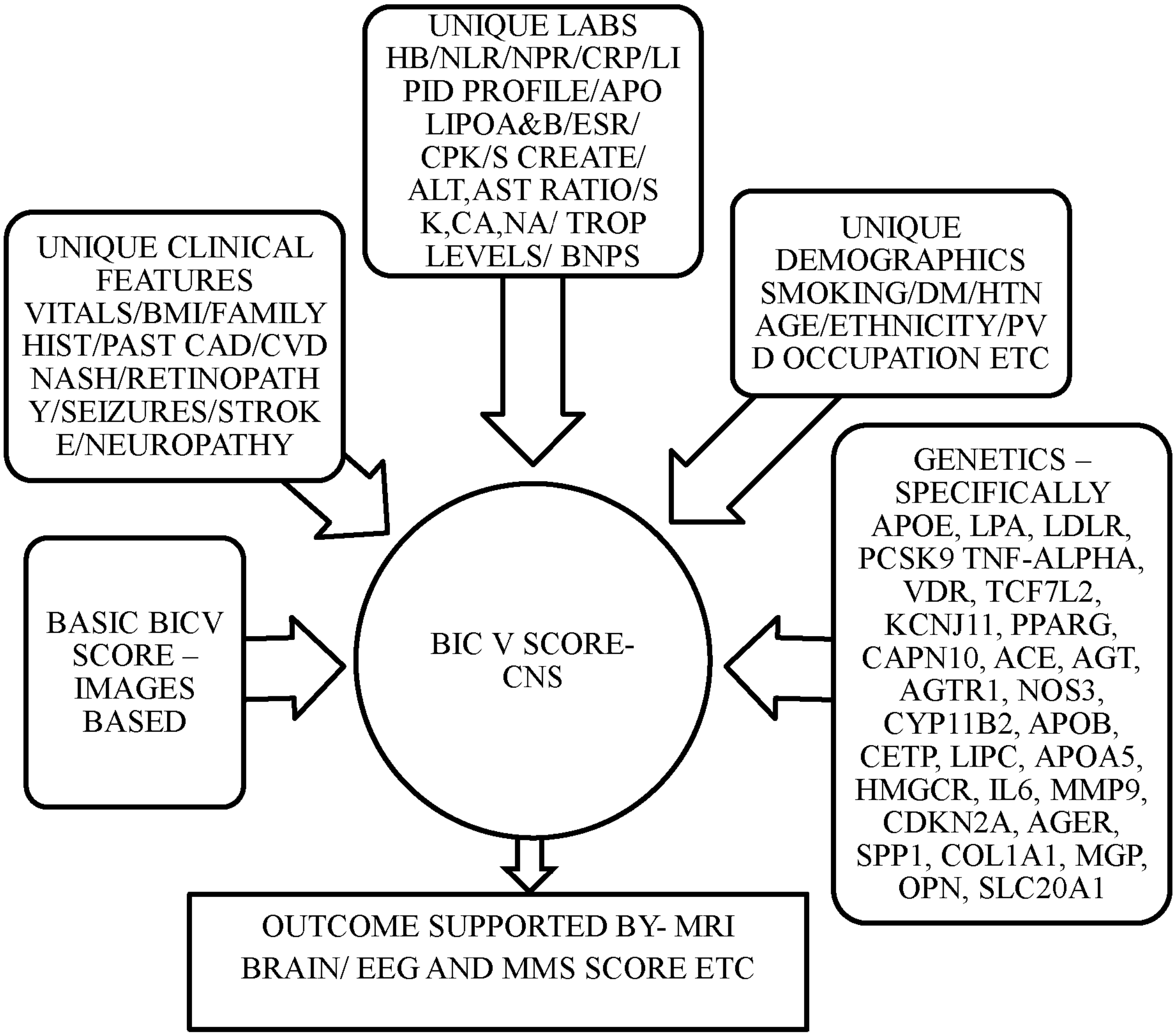
FIG. 11 shows individual level score for cerebrovascular and CNS in BIC-V sub score according to an embodiment.

FIG. 11 shows individual level score for cerebrovascular and CNS in BIC-V sub score according to an embodiment. According to an embodiment of the system, the system determines the cerebrovascular and CNS health risk by augmenting the calcification and the calcification pattern with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises vitals, BMI, family history, past CAD, CVD NASH, retinopathy, seizures, stroke, neuropathy, Hb, NLR, NPR, CRP, Lipid profile, APO, Lipo A&B, ESR, CPK, S Create, ALT, AST ratio, S K, CA, Na, Trop levels, BNPs; and wherein the system further determines a calcification vector from a neuro image and augments the data; and outputs a cerebrovascular and CNS health risk score and a cerebrovascular and CNS health risk assessment from the cerebrovascular and CNS health risk score.

According to an embodiment, it is a cerebrovascular and CNS health assessment method for cerebrovascular and central nervous system assessment, comprising extracting a calcification vector from neuroimaging data; enriching the vector with neurological biomarkers and clinical data comprising genetic markers input comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; clinical data comprising one or more of Vitals, BMI, family history, past CAD, CVD NASH, retinopathy, seizures, Stroke, neuropathy; Hb, NLR, NPR, CRP, Lipid profile, APO, Lipo A&B, ESR, CPK, S Create, ALT, AST ratio, S K, CA, Na, Trop levels, BNPs; and deriving a CNS health score using advanced analytics; applying the score to guide neurology treatments.

Figure 12:
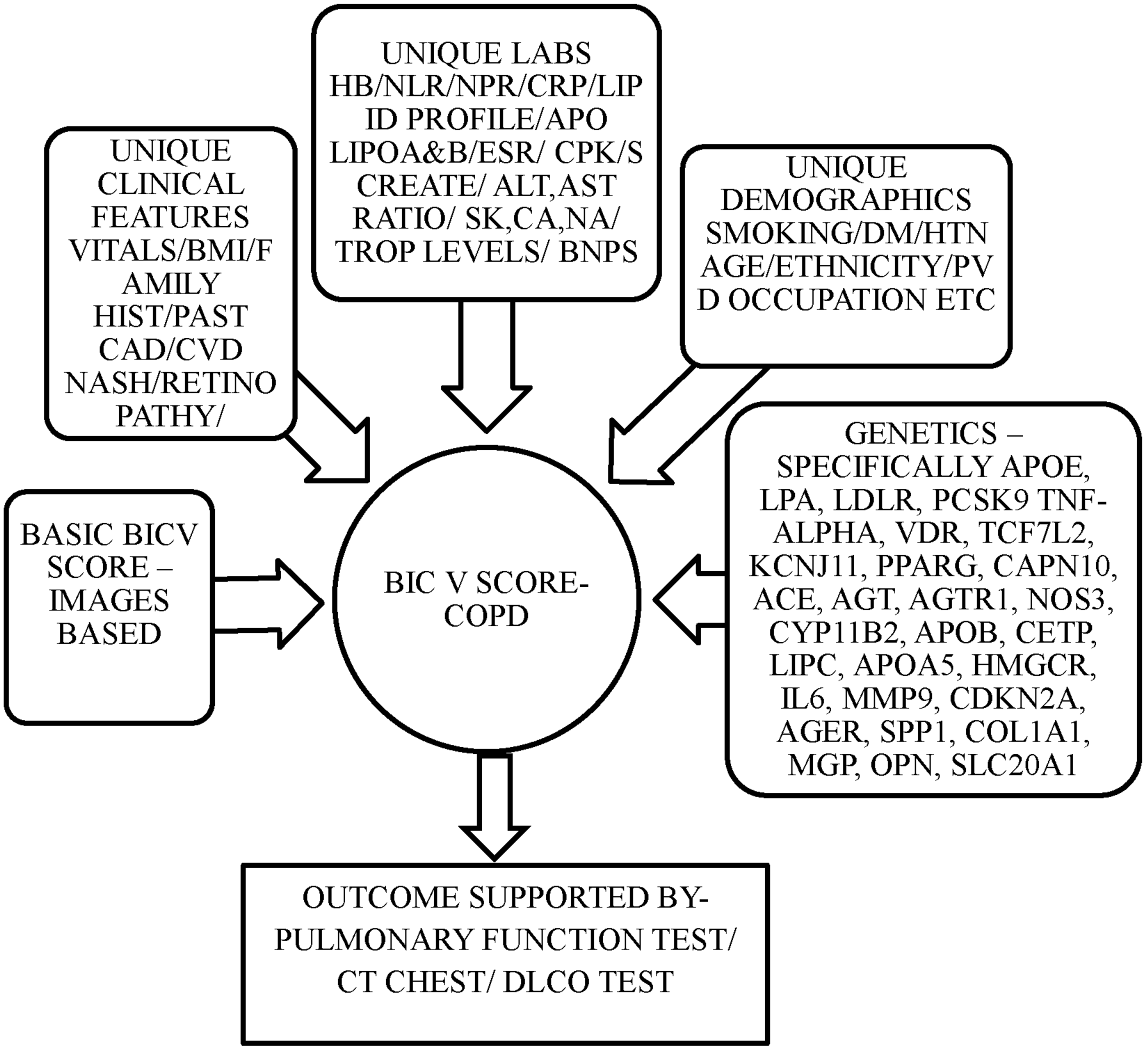
FIG. 12 shows individual level score for Pulmonary/chronic obstructive pulmonary disease (COPD) in BIC-V sub score according to an embodiment.

FIG. 12 shows individual level score for Pulmonary/COPD in BIC-V sub score according to an embodiment. According to an embodiment of the system, the system determines the pulmonary risk by augmenting the calcification and the calcification pattern with the genetic data, the clinical data, a classification vector indicative of electrical pathways; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises vitals, BMI, family history, past CAD, CVD NASH, retinopathy, Hb, NLR, NPR, CRP, Lipid profile, APO, Lipo A&B, ESR, CPK, S Create, ALT, AST ratio, S K, CA, Na, Trop levels, BNPs; and outputs a pulmonary risk score and a pulmonary risk assessment from the pulmonary risk score.

According to an embodiment, it is a pulmonary and COPD assessment method for pulmonary function evaluation, particularly for COPD, comprising: obtaining a calcification vector from breast imaging; enhancing the vector with patient specific data indicative of respiratory function comprising; genetic markers input comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; clinical data comprising one or more of Vitals, BMI, family history, past CAD, CVD NASH, retinopathy; Hb, NLR, NPR, CRP, Lipid profile, APO, Lipo A&B, ESR, CPK, S Create, ALT, AST ratio, S K, CA, Na, Trop levels, BNPs; and computing a pulmonary health score; utilizing the score in respiratory disease management.

Figure 13:
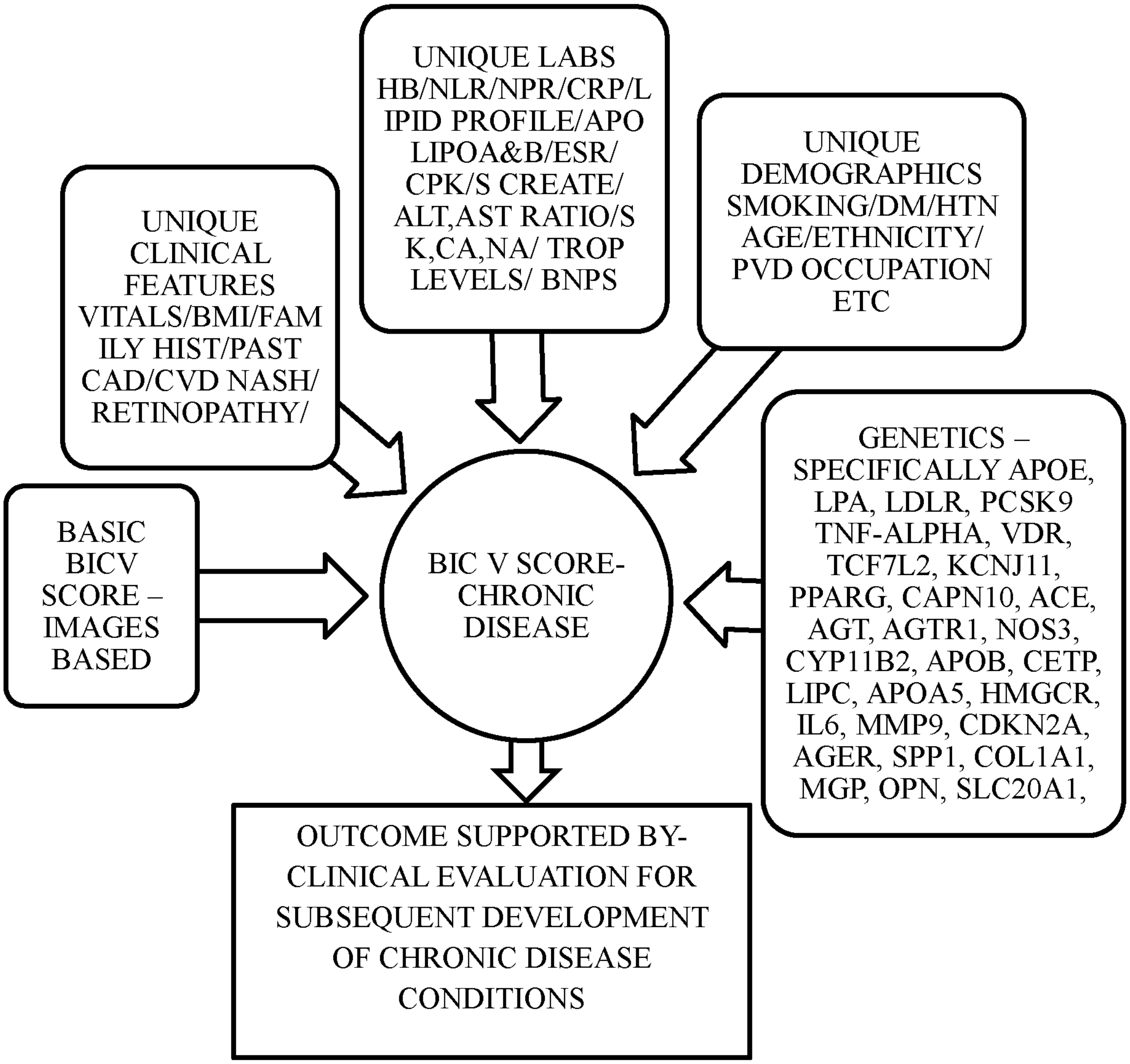
FIG. 13 shows individual level score for Chronic disease in BIC-V sub score according to an embodiment.

FIG. 13 shows individual level score for Chronic disease in BIC-V sub score according to an embodiment. According to an embodiment of the system, the system determines the chronic disease risk by augmenting the calcification and the calcification pattern with the genetic data, the clinical data, a classification vector indicative of chronic diseases; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises vitals, BMI, family history, past CAD, CVD NASH, retinopathy, Hb, NLR, NPR, CRP, Lipid profile, APO, Lipo A&B, ESR, CPK, S Create, ALT, AST ratio, S K, CA, Na, Trop levels, BNPs; and wherein the system further determines a calcification vector from a systemic image and augments the data; and outputs a chronic disease risk score and a chronic disease risk assessment from the chronic disease risk score.

According to an embodiment, it is a chronic disease risk assessment method for chronic disease management, comprising: collecting a calcification vector based on systemic imaging data; integrating continuous health monitoring data into the vector comprising genetic markers input comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; clinical data comprising one or more of Vitals, BMI, family history, past CAD, CVD NASH, retinopathy; Hb, NLR, NPR, CRP, Lipid profile, APO, Lipo A&B, ESR, CPK, S Create, ALT, AST ratio, S K, CA, Na, Trop levels, BNPs; and generating a chronic disease risk score; providing the score for long-term disease management planning.

Figure 14:
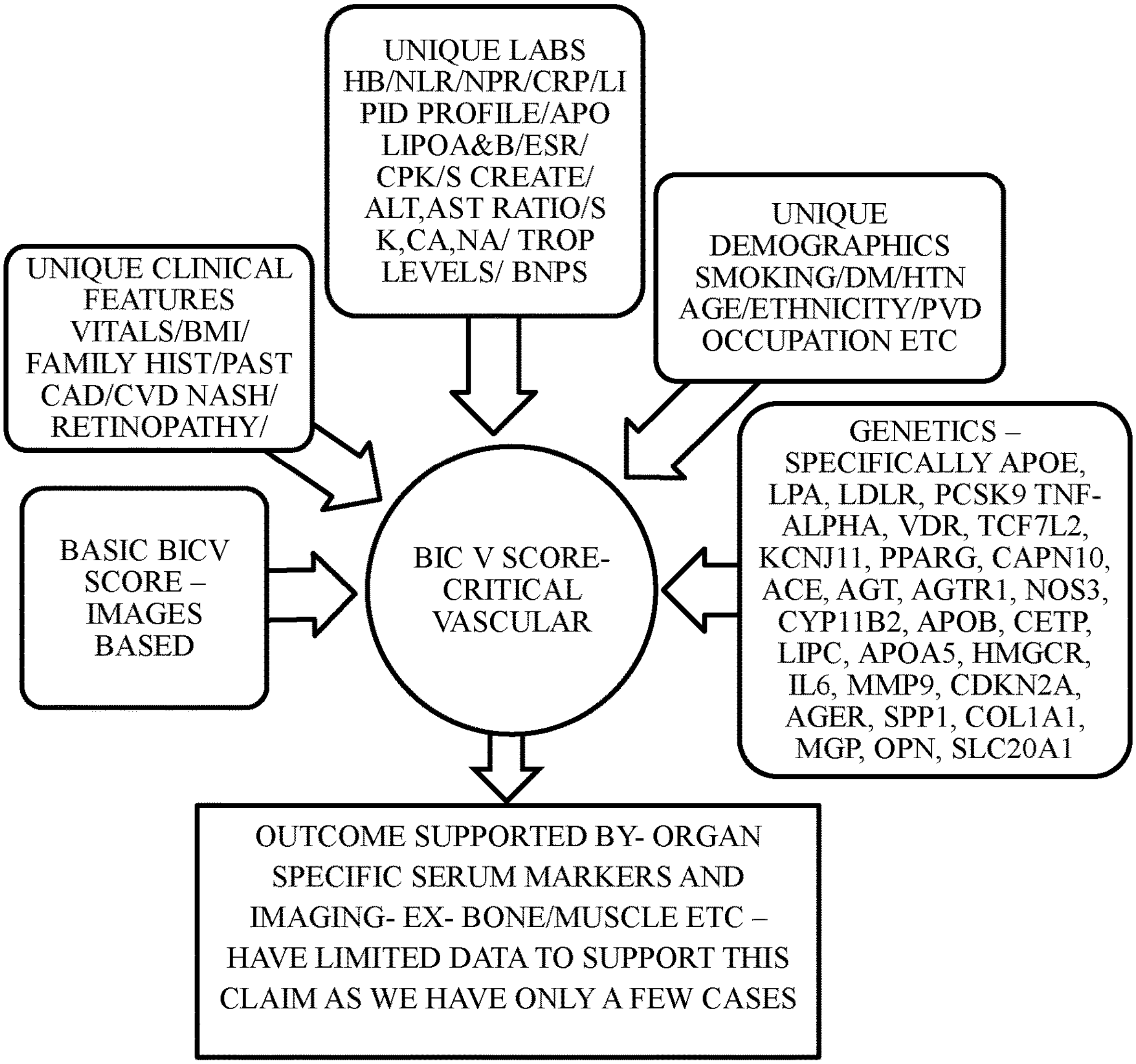
FIG. 14 shows individual level score for critical vascular perfusion in BIC-V sub score according to an embodiment.

FIG. 14 shows individual level score for critical vascular perfusion in BIC-V sub score according to an embodiment. According to an embodiment of the system, the system determines the vascular perfusion risk by augmenting the calcification and the calcification pattern with the genetic data, the clinical data, a classification vector indicative of electrical pathways and critical vascular perfusion; patient specific data with arrhythmias, wherein the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; and wherein the clinical data comprises vitals, BMI, family history, past CAD, CVD NASH, retinopathy, Hb, NLR, NPR, CRP, Lipid profile, APO, Lipo A&B, ESR, CPK, S Create, ALT, AST ratio, S K, CA, Na, Trop levels, BNPs; and wherein the system further determines a calcification vector from a vascular image and augments the data; and outputs a vascular perfusion risk score and a vascular perfusion risk assessment from the vascular perfusion risk score.

According to an embodiment, it is a critical vascular perfusion assessment method for assessing critical vascular perfusion, comprising deriving a calcification vector from vascular imaging data; augmenting the vector with patient specific data under varying conditions comprising genetic markers input comprising one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A1; clinical data comprising one or more of Vitals, BMI, family history, past CAD, CVD NASH, retinopathy; Hb, NLR, NPR, CRP, Lipid profile, APO, Lipo A&B, ESR, CPK, S Create, ALT, AST ratio, S K, CA, Na, Trop levels, BNPs; and categorizing the vascular perfusion into low, medium, or high based on AI analysis; and outputting the categorized scores for emergency and critical care use.

Figure 15:
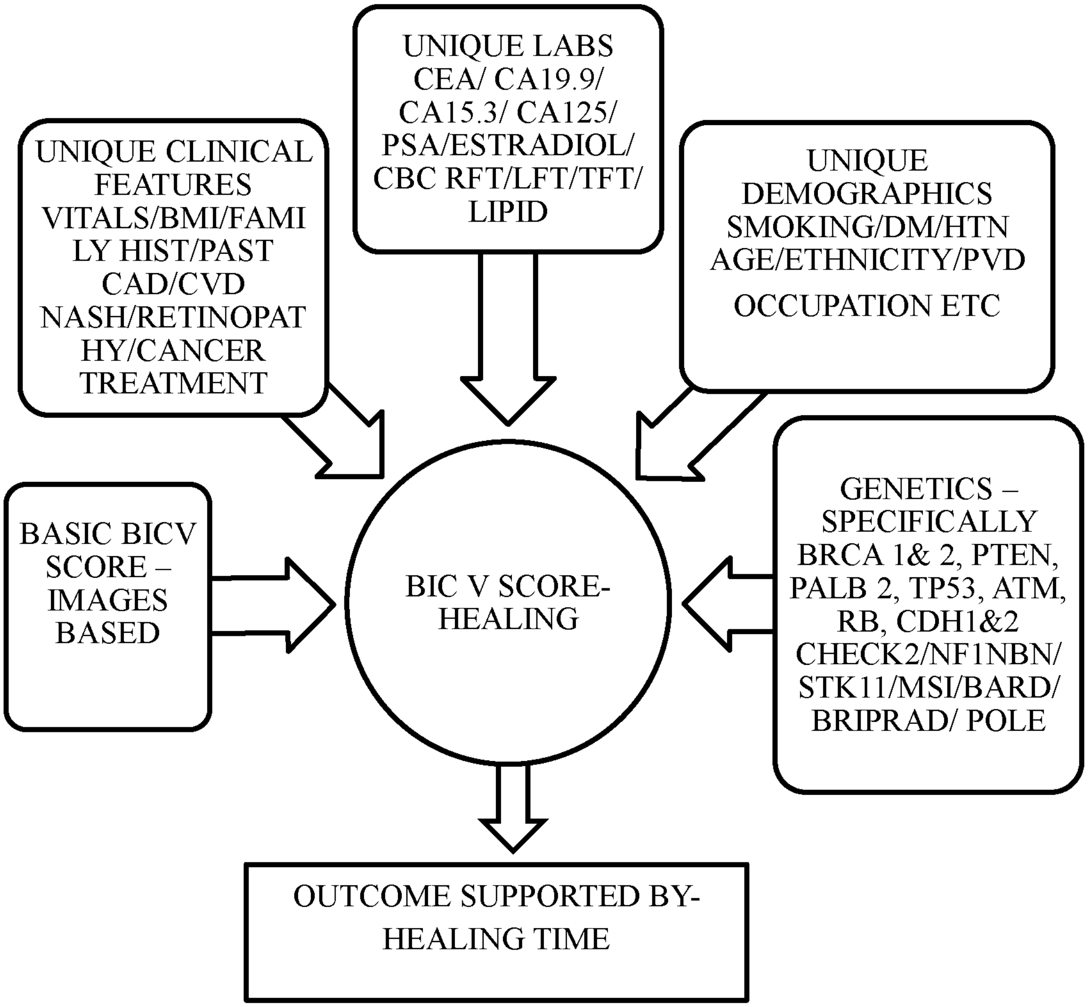
FIG. 15 shows individual level score for Healing in BIC-B sub score according to an embodiment.

FIG. 15 shows individual level score for Healing in BIC-B sub score according to an embodiment. According to an embodiment of the system, the system determines the healing response by augmenting the calcification and the calcification pattern with the genetic data, the clinical data, a classification vector indicative of recovery progress; patient specific data with arrhythmias, wherein the genetic data comprises one or more of BRCA 1, BRCA 2, PTEN, PALB 2, TP53, ATM, RB, CDH1, CDH2, CHEK2, NF1, NBN, STK11, MSI, BARD, BRIPRAD, POLE; and wherein the clinical data comprises vitals, BMI, family history, past CAD, CVD NASH, retinopathy, cancer treatment; CEA, CA19.9, CA15.3, CA125, PSA, Estradiol, CBC RFT, LFT, TFT, Lipid; and wherein the system further determines a calcification vector from a healing or regeneration site image and augments the data; and outputs a healing response score and a healing or recovery assessment from the healing response score.

According to an embodiment, it is a healing assessment method for assessing healing processes using an augmented calcification vector, comprising obtaining a calcification vector from imaging data associated with known healing or regeneration sites; augmenting this vector with patient specific data known to influence healing rates and clinical recovery markers comprising genetic markers input comprising one or more of BRCA 1, BRCA 2, PTEN, PALB 2, TP53, ATM, RB, CDH1, CDH2, CHEK2, NF1, NBN, STK11, MSI, BARD, BRIPRAD, POLE; clinical data comprising one or more of Vitals, BMI, family history, past CAD, CVD NASH, retinopathy, cancer treatment; CEA, CA19.9, CA15.3, CA125, PSA, Estradiol, CBC RFT, LFT, TFT, Lipid processing the augmented vector using a machine learning model to generate a healing score indicative of recovery progress; and outputting the healing score to assist medical professionals in optimizing treatment and rehabilitation plans.

Figure 16:
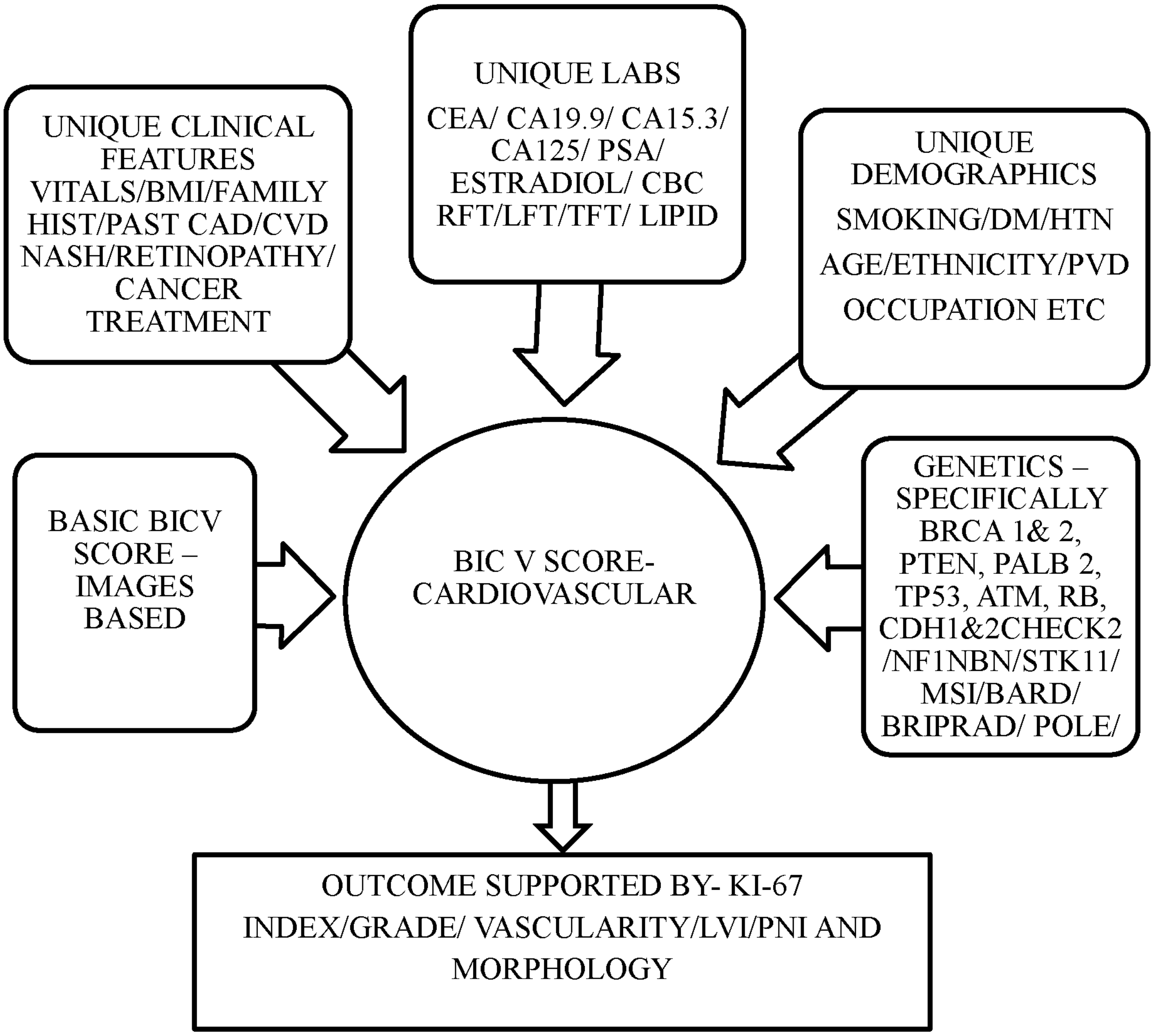
FIG. 16 shows individual level score for Tumor Flow and Growth in BIC-B sub score according to an embodiment.

FIG. 16 shows individual level score for Tumor Flow and Growth in BIC-B sub score according to an embodiment. According to an embodiment of the system, the system determines the tumor flow and growth by augmenting the calcification and the calcification pattern with the genetic data, the clinical data, a classification vector indicative of tumor growth; patient specific data with arrhythmias, wherein the genetic data BRCA 1, BRCA 2, PTEN, PALB 2, TP53, ATM, RB, CDH1, CDH2, CHEK2, NF1, NBN, STK11, MSI/BARD, BRIPRAD, POLE; and wherein the clinical data comprises vitals, BMI, family history, past CAD, CVD NASH, retinopathy, cancer treatment; CEA, CA19.9, CA15.3, CA125, PSA, Estradiol, CBC RFT, LFT, TFT, Lipid; and wherein the system further determines a calcification vector from a tumor morphology and associated vascular structures image and augments the data; and outputs a tumor flow and growth score and a tumor flow and growth assessment from the tumor flow and growth score.

According to an embodiment, it is a tumor flow and growth assessment method for monitoring tumor growth and vascular activity using an augmented calcification vector, comprising extracting a calcification vector from imaging data capturing tumor morphology and associated vascular structures; enhancing the vector with patient-specific genetic markers related to oncogenesis and tumor growth factors comprising genetic markers input comprising one or more of BRCA 1, BRCA 2, PTEN, PALB 2, TP53, ATM, RB, CDH1, CDH2, CHEK2, NF1, NBN, STK11, MSI, BARD, BRIPRAD, POLE; clinical data comprising one or more of Vitals, BMI, family history, past CAD, CVD NASH, retinopathy, cancer treatment; CEA, CA19.9, CA15.3, CA125, PSA, Estradiol, CBC RFT, LFT, TFT, Lipid; and applying a machine learning algorithm to derive a tumor flow and growth score from the enhanced vector; using the score to guide oncological treatment decisions, including chemotherapy, radiation, and surgical interventions.

Figure 17:
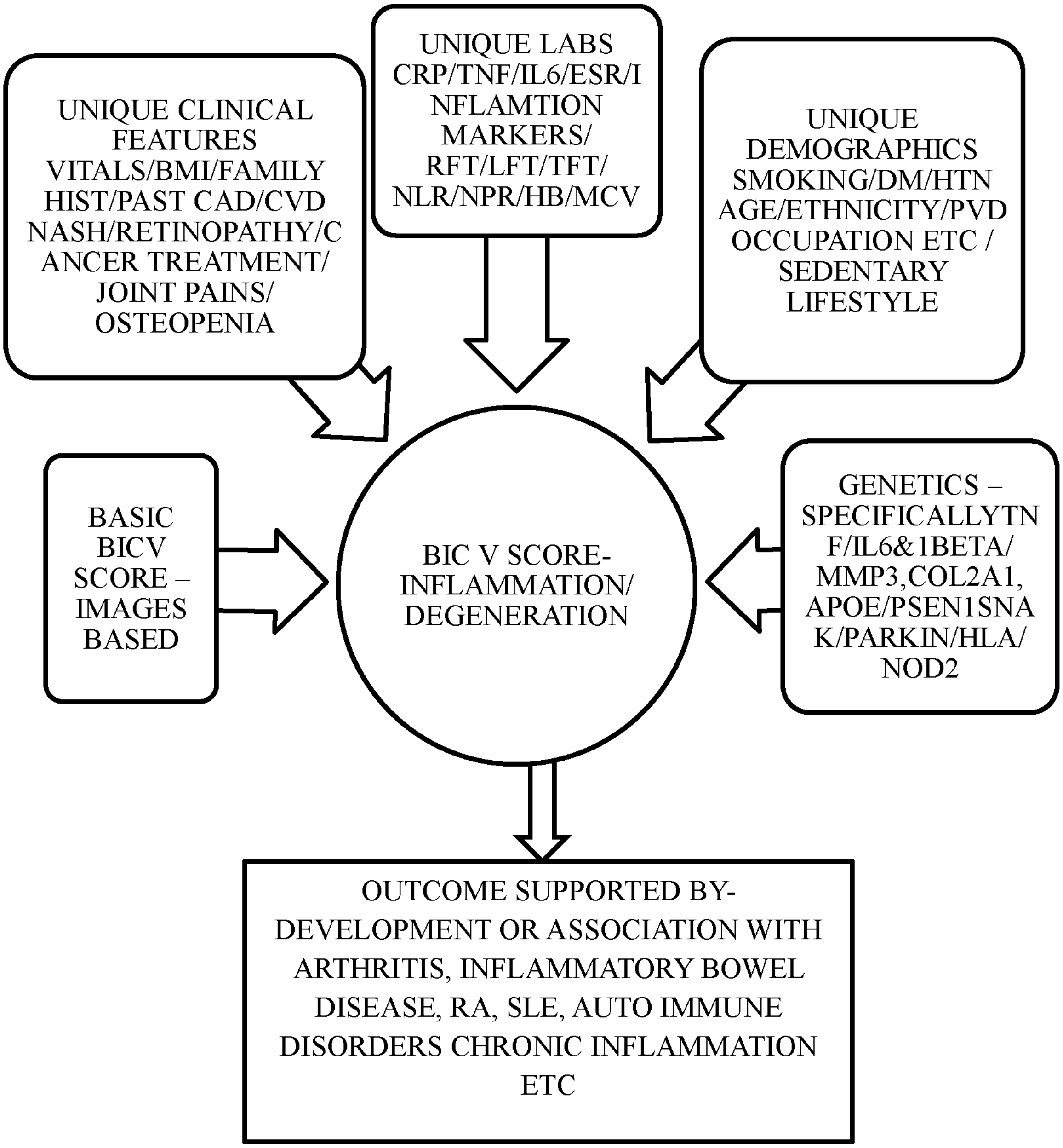
FIG. 17 shows individual level score for inflammation in BIC-B sub score according to an embodiment.

FIG. 17 shows individual level score for inflammation in BIC-B sub score according to an embodiment. According to an embodiment of the system, the system determines the inflammation and degeneration by augmenting the calcification and the calcification pattern with the genetic data, the clinical data, a classification vector indicative of electrical pathways and inflammation and degeneration; patient specific data with arrhythmias, wherein the genetic data TNF, IL6, IL1B, MMP3, COL2A1, APOE, PSEN1, SNAK, PARKIN, HLA, NOD2; and wherein the clinical data comprises vitals, BMI, family history, past CAD, CVD NASH, retinopathy, cancer treatment, joint pains, osteopenia, CRP, TNF, IL6, ESR, inflammation markers, RFT, LFT, TFT, NLR, NPR, Hb, MCV; and wherein the system further determines a calcification vector from an area image affected by inflammatory or degenerative changes and augments the data; and outputs an inflammation and degeneration score and an inflammation and degeneration assessment from the inflammation and degeneration score.

According to an embodiment, it is an Inflammation and Degeneration Assessment method for evaluating inflammation and degenerative conditions, comprising: generating a calcification vector from imaging studies focused on areas typically affected by inflammatory or degenerative changes; integrating clinical data such as biomarkers of inflammation and genetic predispositions into the vector comprising genetic markers input comprising one or more of TNF, IL6, IL1B, MMP3, COL2A1, APOE, PSEN1, SNAK, PARKIN, HLA, NOD2; clinical data comprising one or more of Vitals, BMI, family history, past CAD, CVD NASH, retinopathy, cancer treatment, Joint pains, Osteopenia; CRP, TNF, IL6, ESR, Inflammation markers, RFT, LFT, TFT, NLR, NPR, Hb, MCV; and employing a machine learning model to compute an inflammation and degeneration score reflecting the severity and extent of the condition; and providing the score for managing treatments in conditions such as arthritis, multiple sclerosis, and Alzheimer's disease.

Figure 18:
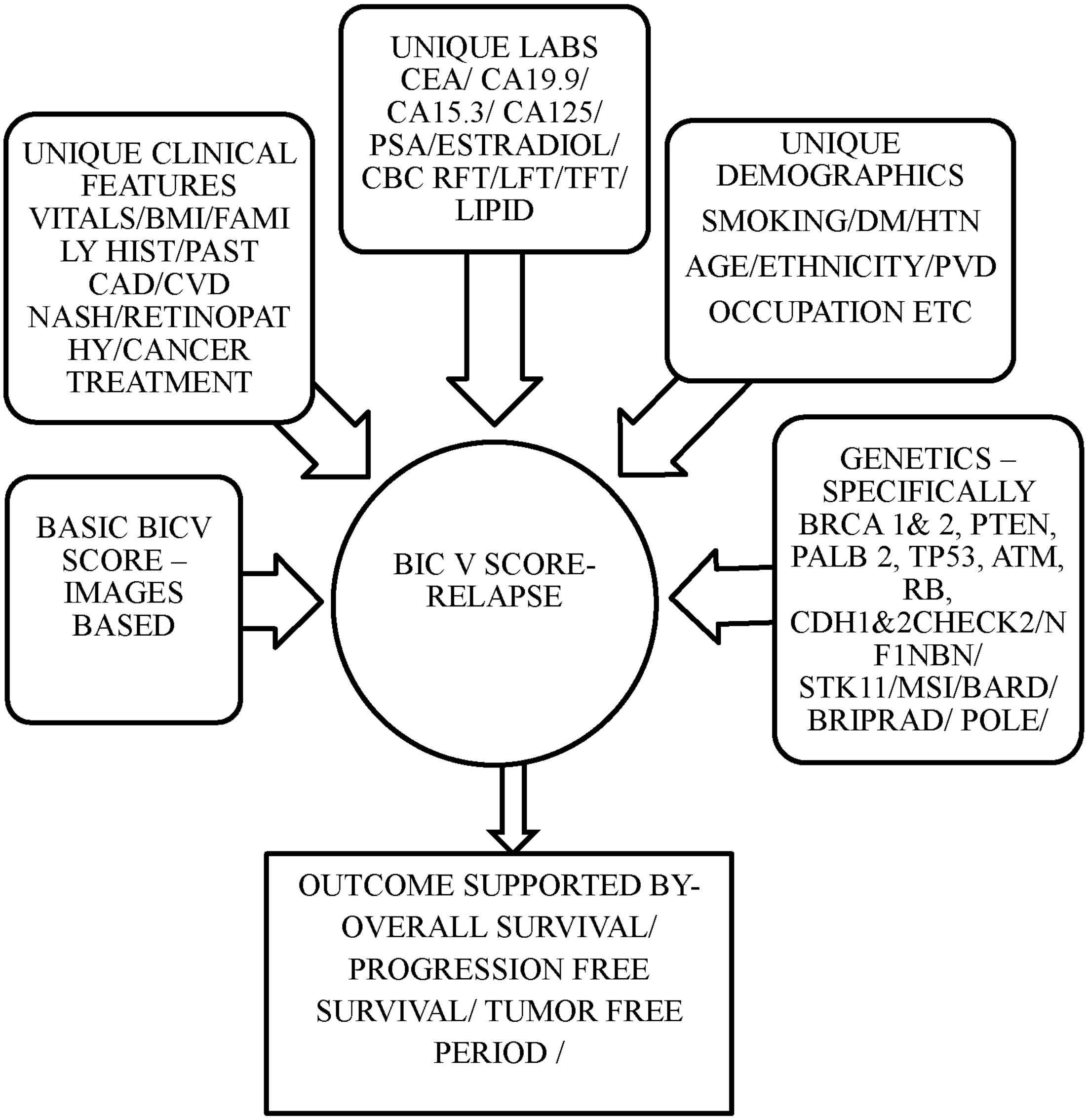
FIG. 18 shows individual level score for relapse in BIC-B sub score according to an embodiment.

FIG. 18 shows individual level score for relapse in BIC-B sub score according to an embodiment. According to an embodiment of the system, the system determines the disease relapse by augmenting the calcification and the calcification pattern with the genetic data, the clinical data, a classification vector indicative of disease relapse; patient specific data with arrhythmias, wherein the genetic data comprises one or more of BRCA 1, BRCA 2, PTEN, PALB 2, TP53, ATM, RB, CDH1, CDH2, CHEK2, NF1, NBN, STK11, MSI, BARD, BRIPRAD, POLE; and wherein the clinical data comprises vitals, BMI, family history, past CAD, CVD NASH, retinopathy, cancer treatment, CEA, CA19.9, CA15.3, CA125, PSA, Estradiol, CBC RFT, LFT, TFT, lipid; and wherein the system further determines a calcification vector from a diagnostic image and augments the data; and outputs a disease relapse score and a disease relapse assessment from the disease relapse score.

Figure 19:
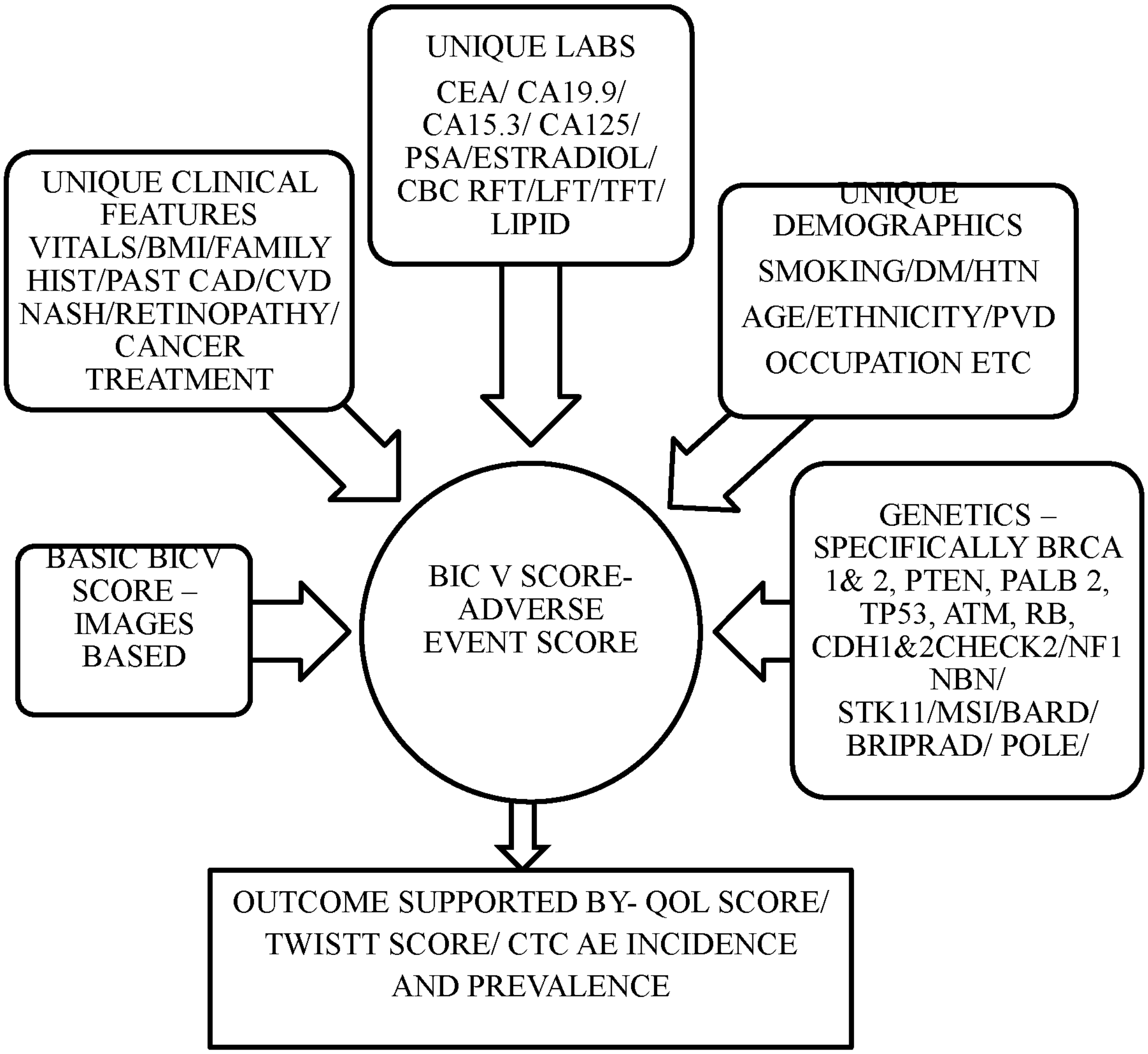
FIG. 19 shows individual level score for adverse event in BIC-B sub score according to an embodiment.

According to an embodiment, it is a disease relapse assessment method for predicting disease relapse, comprising creating a calcification vector from diagnostic images taken during remission phases of a previously treated disease; augmenting the vector with data on genetic relapse markers and historical clinical data comprising genetic markers input comprising one or more of BRCA 1, BRCA 2, PTEN, PALB 2, TP53, ATM, RB, CDH1, CDH2, CHEK2, NF1, NBN, STK11, MSI, BARD, BRIPRAD, POLE; clinical data comprising one or more of Vitals, BMI, family history, past CAD, CVD NASH, retinopathy, cancer treatment; CEA, CA19.9, CA15.3, CA125, PSA, Estradiol, CBC RFT, LFT, TFT, Lipid; and analyzing the augmented vector with a machine learning model to predict the likelihood of disease relapse; and outputting a relapse probability score to enable proactive patient management and preventive care strategies. FIG. 19 shows individual level score for adverse event in BIC-B sub score according to an embodiment. According to an embodiment of the system, the system determines the adverse event by augmenting the calcification and the calcification pattern with the genetic data, the clinical data, a classification vector indicative of adverse events s; patient specific data with arrhythmias, wherein the genetic data comprises one or more of BRCA 1, BRCA 2, PTEN, PALB 2, TP53, ATM, RB, CDH1, CDH2, CHEK2, NF1, NBN, STK11, MSI, BARD, BRIPRAD, POLE; and wherein the clinical data comprises vitals, BMI, family history, past CAD, CVD NASH, retinopathy, cancer treatment, CEA, CA19.9, CA15.3, CA125, PSA, Estradiol, CBC RFT, LFT, TFT, lipid; and wherein the system further determines a calcification vector from a treatment evaluation image taken during a treatment cycle and augments the data; and outputs an adverse event score and an adverse event assessment from the adverse event score.

According to an embodiment, it is an adverse events monitoring method for monitoring adverse events in patients undergoing treatment, comprising collecting a calcification vector from routine imaging performed during treatment cycles; augmenting this vector with patient specific data comprising genetic markers input comprising one or more of BRCA 1, BRCA 2, PTEN, PALB 2, TP53, ATM, RB, CDH1, CDH2, CHEK2, NF1, NBN, STK11, MSI, BARD, BRIPRAD, POLE; clinical data comprising one or more of Vitals, BMI, family history, past CAD, CVD NASH, retinopathy, cancer treatment; CEA, CA19.9, CA15.3, CA125, PSA, Estradiol, CBC RFT, LFT, TFT, Lipid; and processing the data through a machine learning model to generate an adverse event risk score; and deploying the risk score to adjust treatment protocols and mitigate potential side effects in patient care.

Figure 20:
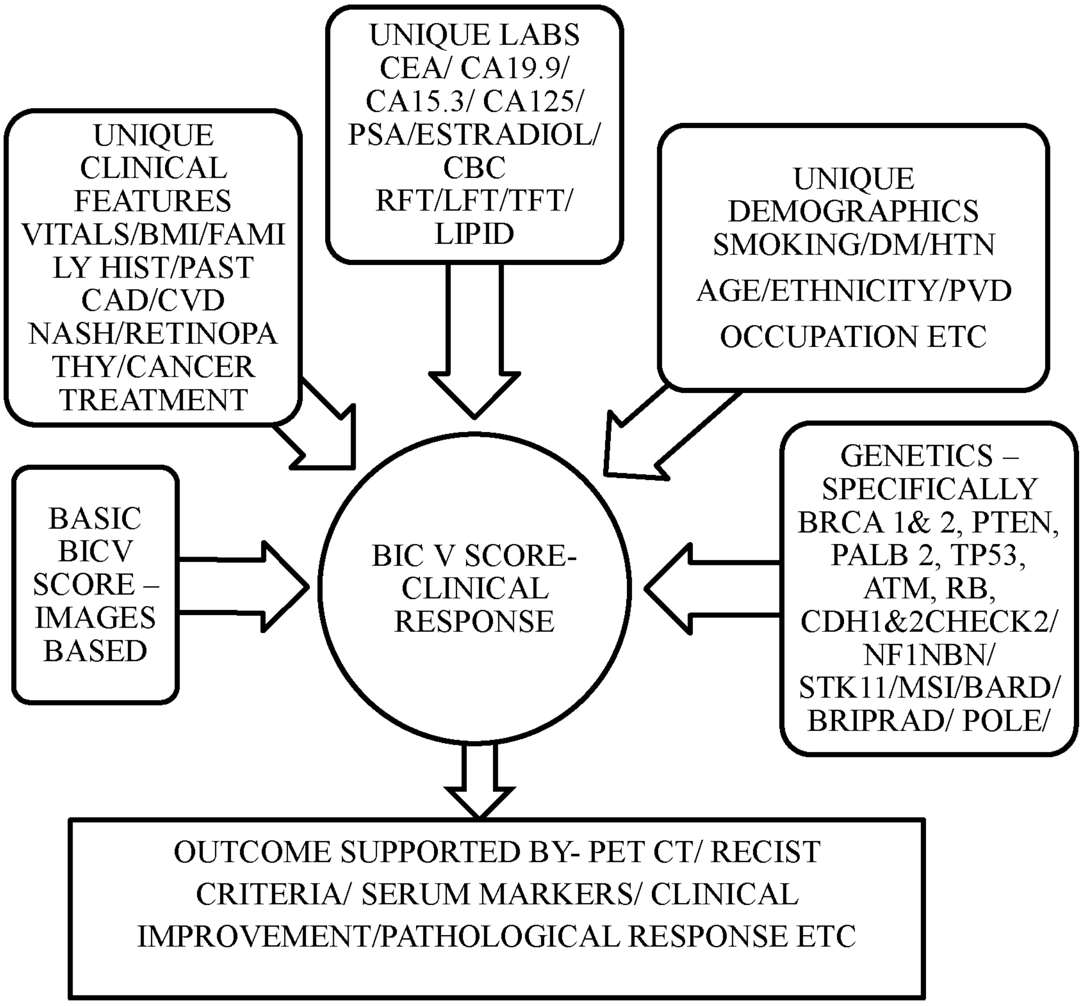
FIG. 20 shows individual level score for clinical response in BIC-V sub score according to an embodiment.

FIG. 20 shows individual level score for clinical response in BIC-V sub score according to an embodiment. According to an embodiment of the system, the system determines the clinical response by augmenting the calcification and the calcification pattern with the genetic data, the clinical data, a classification vector indicative of electrical pathways and clinical responses; patient specific data with arrhythmias, wherein the genetic data BRCA 1, BRCA 2, PTEN, PALB 2, TP53, ATM, RB, CDH1, CDH2, CHEK2, NF1, NBN, STK11, MSI, BARD, BRIPRAD, POLE; and wherein the clinical data comprises vitals, BMI, family history, past CAD, CVD NASH, retinopathy, cancer treatment, CEA, CA19.9, CA15.3, CA125, PSA, Estradiol, CBC RFT, LFT, TFT, lipid; and wherein the system further determines a calcification vector from a post treatment evaluation image and augments the data; and outputs an clinical response score and an clinical response assessment from the clinical response score.

According to an embodiment, it is a clinical response evaluation method for assessing clinical response to treatments, comprising deriving a calcification vector from imaging data pre- and post-treatment; enhancing the vector with patient specific markers comprising genetic markers input comprising one or more of BRCA 1, BRCA 2, PTEN, PALB 2, TP53, ATM, RB, CDH1, CDH2, CHEK2, NF1, NBN, STK11, MSI, BARD, BRIPRAD, POLE; clinical data comprising one or more of Vitals, BMI, family history, past CAD, CVD NASH, retinopathy, cancer treatment; CEA, CA19.9, CA15.3, CA125, PSA, Estradiol, CBC RFT, LFT, TFT, Lipid; and utilizing a machine learning framework to calculate a clinical response score that quantifies the effectiveness of the treatment; providing the score to healthcare providers to tailor ongoing or future treatment regimens based on patient response.

FIG. 21A shows genetic markers input for BIC-V group according to an embodiment. The provided table lists various health conditions and their associated genetic markers that contribute to the calculation of the BRICC-G score, a comprehensive risk assessment metric. Each sub-score is based on the analysis of specific genetic markers that have been identified to influence the respective health conditions. The sub-scores for different health conditions are combined to determine the overall BRICC-G score.

FIG. 21B shows individual level score for BIC-B group according to an embodiment. The table shows the list of health conditions with additional sub-scores focused on healing, tumor dynamics, and other critical aspects of patient health. These sub-scores, identified as BIC-B, utilize specific genetic markers to assess various medical conditions and predict outcomes. The integration of these genetic markers with the BIC-V scores contributes to the comprehensive BRICC-G score.

FIG. 22A shows clinical data input for BIC-V group according to an embodiment. The table shows a detailed description of clinical and laboratory inputs used to evaluate various health conditions. Each sub-score, identified as BIC-V, incorporates specific clinical and laboratory data, contributing to the comprehensive BRICC-G score.

Clinical and Laboratory Inputs Used for BIC-V Sub-Scores

Cardiovascular:
- Clinical Data: Vitals, BMI, Family History, past CAD/CVD, NASH, retinopathy
- Laboratory Data: Hemoglobin (Hb), Neutrophil to Lymphocyte Ratio (NLR), Neutrophil to Platelet Ratio (NPR), C-reactive protein (CRP), Lipid profile, Apolipoprotein LipoA & B, Erythrocyte Sedimentation Rate (ESR), Creatine Phosphokinase (CPK), Serum Creatinine (S. Creat), ALT/AST ratio, Serum Potassium (S. K), Calcium (S. CA), Sodium (S. Na), Troponin levels, Brain Natriuretic Peptides (BNPs)

Cardiac Contractile:
- Clinical Data: Vitals, BMI, Family History, past CAD/CVD, NASH, retinopathy, 6-minute walk test
- Laboratory Data: Same as Cardiovascular with the addition of Treadmill Test (TMT)

Cardiac Rhythm:
- Clinical Data: Vitals, BMI, Family History, past CAD/CVD, NASH, retinopathy
- Laboratory Data: Same as Cardiovascular Renovascular & Renal Perfusion:
- Clinical Data: Vitals, BMI, Family History, past CAD/CVD, NASH, retinopathy, edema, urine output, mental status, skin changes
- Laboratory Data: Hemoglobin (Hb), Neutrophil to Lymphocyte Ratio (NLR), Neutrophil to Platelet Ratio (NPR), C-reactive protein (CRP), Lipid profile, Erythrocyte Sedimentation Rate (ESR), Urea, Uric acid, Serum Creatinine (S. Creat), Serum Potassium (S. K), Calcium (S. CA), Sodium (S. Na), Brain Natriuretic Peptides (BNPs), Complete Urine Examination (CUE), 24-hour urine protein, Protein to Creatinine ratio, Erythropoietin (EPO), Vanillylmandelic Acid (VMA), Catecholamines Retinopathy:
- Clinical Data: Vitals, BMI, Family History, past CAD/CVD, NASH
- Laboratory Data: Hemoglobin (Hb), Neutrophil to Lymphocyte Ratio (NLR), Neutrophil to Platelet Ratio (NPR), C-reactive protein (CRP), Lipid profile, Apolipoprotein LipoA & B, Erythrocyte Sedimentation Rate (ESR), Creatine Phosphokinase (CPK), Serum Creatinine (S. Creat), Hemoglobin A1C (HbA1C), Bilirubin Pancreatic:
- Clinical Data: Vitals, BMI, Family History, past CAD/CVD, NASH, abdominal findings, food habits
- Laboratory Data: Hemoglobin (Hb), Neutrophil to Lymphocyte Ratio (NLR), Neutrophil to Platelet Ratio (NPR), C-reactive protein (CRP), Lipid profile, Apolipoprotein LipoA & B, Erythrocyte Sedimentation Rate (ESR), Amylase, Lipase, CA 19.9, Serum Creatinine (S. Creat), ALT/AST ratio, Serum Bilirubin Cerebrovascular & CNS:
- Clinical Data: Vitals, BMI, Family History, past CAD/CVD, NASH, retinopathy, seizures, stroke, neuropathy
- Laboratory Data: Same as Cardiovascular Pulmonary/COPD:
- Clinical Data: Vitals, BMI, Family History, past CAD/CVD, NASH, retinopathy
- Laboratory Data: Same as Cardiovascular Chronic Disease:
- Clinical Data: Vitals, BMI, Family History, past CAD/CVD, NASH, retinopathy
- Laboratory Data: Same as Cardiovascular Critical Vascular Perfusion:

Clinical Data: Vitals, BMI, Family History, past CAD/CVD, NASH, retinopathy

Laboratory Data: Same as Cardiovascular

This detailed compilation of clinical and laboratory inputs is utilized to evaluate various health conditions associated with the BIC-V sub-scores. Each sub-score integrates specific clinical and laboratory data to provide a comprehensive assessment of cardiovascular, renal, retinal, pancreatic, cerebrovascular, pulmonary, chronic disease, and critical vascular perfusion health. These inputs contribute to the overall BRICC-G score, enhancing the accuracy and depth of patient health evaluation.

FIG. 22B shows clinical data input for BIC-V group according to an embodiment.

The table shows the list of clinical and laboratory inputs, focusing on healing, tumor dynamics, relapse, adverse events, clinical response, and inflammation or degeneration. Each sub-score, labelled as BIC-B, involves specific clinical and laboratory data essential for comprehensive health assessments.

Clinical and Laboratory Inputs which are used for BIC-B Sub-Scores

For Healing, Tumor Flow and Growth, Relapse, Adverse Event, and Clinical Response:

Clinical Data: Vitals, BMI, Family History, past CAD/CVD, NASH, retinopathy, cancer treatment.

Laboratory Data: Carcinoembryonic Antigen (CEA), CA19.9, CA15.3, CA125, Prostate-Specific Antigen (PSA), Estradiol, Complete Blood Count (CBC), Renal Function Tests (RFT), Liver Function Tests (LFT), Thyroid Function Tests (TFT), Lipid profile.

For Inflammation/Degeneration:

Clinical Data: Vitals, BMI, Family History, past CAD/CVD, NASH, retinopathy, cancer treatment, Joint pains, Osteopenia.

Laboratory Data: C-reactive protein (CRP), Tumor Necrosis Factor (TNF), Interleukin 6 (IL6), Erythrocyte Sedimentation Rate (ESR), Inflammation markers, Renal Function Tests (RFT), Liver Function Tests (LFT), Thyroid Function Tests (TFT), Neutrophil to Lymphocyte Ratio (NLR), Neutrophil to Platelet Ratio (NPR), Hemoglobin (Hb), Mean Corpuscular Volume (MCV).

This list of clinical and laboratory inputs encompasses data for assessing healing processes, tumor progression, relapse potential, adverse events, clinical response, and inflammation or degeneration. Each BIC-B sub-score leverages specific clinical and laboratory inputs, contributing to a thorough evaluation of patient health in various contexts, particularly those related to cancer and inflammatory conditions. These inputs enhance the overall BRICC-G score, ensuring a nuanced and detailed health assessment.

Figure 23:
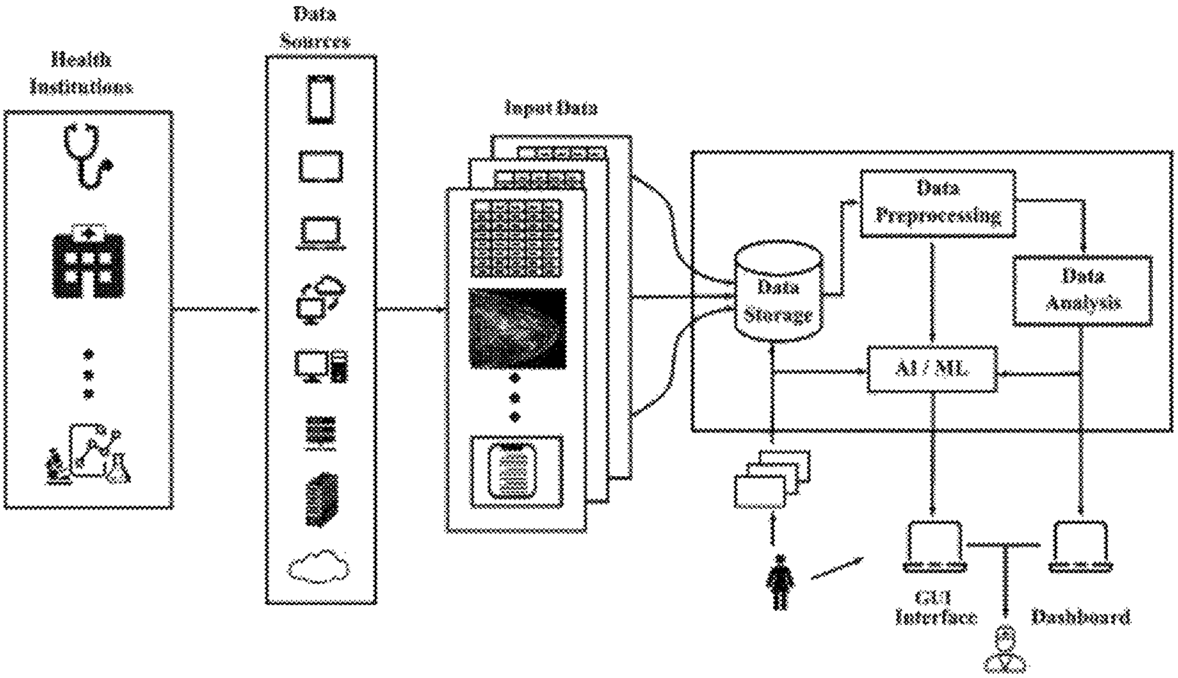
FIG. 23 shows the overview of the Artificial Intelligence System for generating BRICC-G score according to an embodiment.

FIG. 23 shows the overview of the Artificial Intelligence System for generating BRICC-G score according to an embodiment. Designing and developing a complex computation system for predicting risks utilizes a software ecosystem/platform with robust computational infrastructure encompassing components for:

- Gathering data from multiple data sources such as health institutions, databases, electronic health records, and image data from clinics, data generated or observations/notes made by Nurses, Doctors, Clinicians, Labs, Hospitals, health institutions etc.;
- Using diverse technologies for collection, processing, storage and distribution of data such as Smartphones, iPad®s, Desktop/Personal Computers, Stand-alone/On-Premise/Cloud Servers etc.;
- Organizing data in a data storage system and in auxiliary storage devices, wherein auxiliary storage devices include hard disk drives (HDDs), solid-state drives (SSDs), optical discs (CDs, DVDs, Blu-ray discs), USB flash drives, external hard drives, memory cards (SD cards, microSD cards), network attached storage (NAS), and cloud storage;
- Data preprocessing analytics; Cleansing of data stored in databases is known to improve performance of subsequent processes (analytics and prediction) in the pipeline;
- Dashboard for rendering insights from analytics;
- A suite of Artificial Intelligence (AI) and Machine Learning (ML) models for learning knowledge to predict risks; and
- Web interface that displays various risks and overall health risk given the image data and input data comprising genetics and clinical data of the patient using the knowledge from AI algorithms.

Input-Data Acquisition

Artificial Intelligence System acquires data from multiple sources as the patient's characteristics are captured and stored by different entities at various places, multiple times. In general, characteristics are categorized under medical, clinical, demographic, lifestyle, and genetic.

Each of these characteristics are captured in different data formats. Some of these characteristics are stored in a structured format/represented tabularly. However, information about laboratory tests and results are represented as reports while Clinicians' notes are often textual, audio, video files. Furthermore, all of the patients' medical scans are in image format. Some of the clinical characteristics can be captured and stored in a data format such as CSV/Excel/JSON/XML/PDF/TXT, but image scans are stored in unstructured image format. Further, summarization of textual data from laboratory reports and clinical notes can be performed by applying pre-processing techniques.

The Artificial Intelligence System leverages a suite of Machine/Deep Learning algorithms for exploration of factors associated with risks and subsequently computes the scores for various types of risks. The system adopts and stacks numerous techniques for performing the tasks such as pre-processing, exploratory analysis and prediction of risk score.

Figure 24:
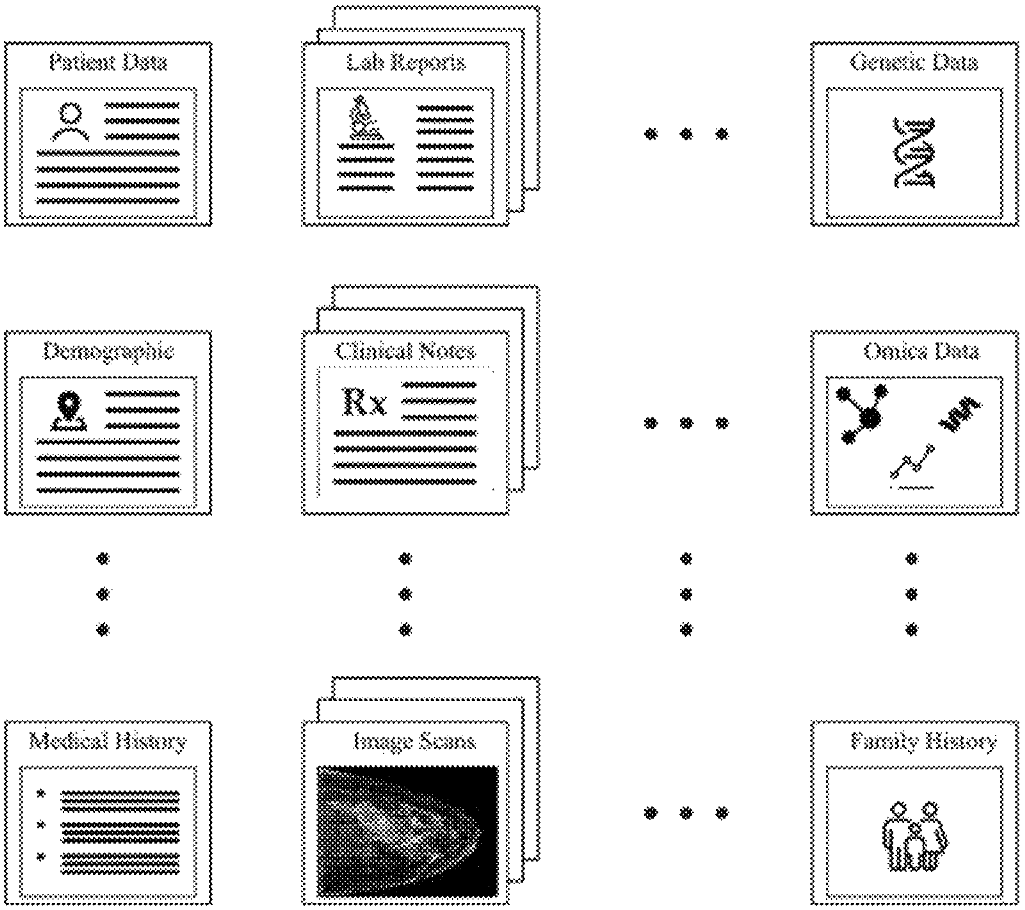
FIG. 24 shows the patient records and patient data obtained from multiple sources according to an embodiment.

FIG. 24 shows the patient records and patient data obtained from multiple sources according to an embodiment. The data formats vary between sources depending upon how the data is stored and organized. Medical data may be inconsistent due to the nature of data acquisition processes and diversity of the nature of data. Further, data may contain noise, which refers to irrelevant, redundant, or erroneous information that can obscure meaningful insights and affect the accuracy and quality of data analysis.

Therefore, the Artificial Intelligence System runs its preprocessing algorithms that deal with processing both structured and unstructured data. These algorithms pre-process the structured, unstructured, and image data and then forward the cleaned data to the subsequent modules for further processing and analysis. Some of the challenges in cleaning medical data and pre-processing approaches are:

Structured Data

Data Inaccuracy—handling the incomplete, missing values can be done using traditional techniques such as imputation with mean, normal values and also with model-based approaches such as multivariate regression and k-nearest neighbor.

Data Noise—reducing noise by removing erroneous data and outliers from the data by multivariate approaches using different similarity measures such as Mahalanobis and Cook.

Data Inconsistency—identified when data is input from various sources. During this time the source with the most inconsistent data can be identified and can be addressed using correlation analysis.

Unstructured Data

Dr. Notes/Text: For textual data the normalization can be a task for analysis of clinical notes and patient's laboratory reports. With normalization, Artificial Intelligence System handles some of the challenges in text processing such as:

Format/Code Conversion—data from multiple sources in various formats/codes can be collected and converted to simple format. Artificial Intelligence System incorporates Scripts for converting files in different formats to one standard format.

Eliminating Stop Words/Punctuations/Non-ASCII characters—Artificial Intelligence System incorporates regular expression scripts to eliminate the stop words, punctuations and non-ascii characters.

Identifying Stem Words—reducing each word in the text to base or root will improve the analysis of textual data. Artificial Intelligence System comprises modules for performing stemming on clinical and laboratory notes.

Lemmatization—as used herein can refer to reducing words to base form by considering the context along with the content. This is known as lemmatization and can be useful in identifying clinical, biological entities in notes or reports. Alternatively, lemmatization of words helps to tag the text.

Medical Scans/Images

For processing medical images, the Artificial Intelligence System can provide modules to perform the following tasks:

Image Resize & Normalization—Images of different patients collected from different sources usually have different dimensions that are to be resized. According to various embodiments the Artificial Intelligence System encompasses methods such as nearest neighbor and neural networks to perform up-scaling and down-scaling of images and also methods for transformation.

Noise Reduction—Noise in the medical images occurs due to variations in capturing and can be undesirable for image analysis. Therefore, the Artificial Intelligence System comprises techniques that support reduction of various types of noises including, but not limited to, Pepper, Gaussian and Poisson. According to various embodiments the Artificial Intelligence System comprises Neural networks-based modules to suppress the noise in scanned images.

Blur—Along with noise the other major distorter for quality of an image is blur which results in affecting the accuracy of the prediction models. According to an embodiment the Artificial Intelligence System comprises Kernel filters such as gaussian blur, deep neural networks, to sharpen and blur the images during the training of the prediction model. Consequently, during real time prediction, the model will have acquired resistance to blurring in the medical images.

EDA—Exploratory Data Analysis Artificial Intelligence System also considers the synthesized results pertaining to the factors associated with cancer or any other organ risk and progression of cancer/healing etc. These results can show the incidence and prevalence of the factors for risks besides providing deep insights into understanding the behavior of risk factors for different cohorts. Clinicians can use such an exploratory analysis in designing the prevention and intervention strategies. Results can be rendered by rich graphical presentations through a dashboard that enables easy interpretation and assessment of risk indicators. Some of the visualizations rendered in the dashboard include, but are not limited to:

Visualization of indicators for breast cancer and/or its progression may particularly show factors such as Genetic Factors, Hormonal Factors, Environmental Factors, Lifestyle Factors, Reproductive History, Biological Factors, Systemic Health, and Medical History. These factors are typically depicted using speedometers, gauge meters, and horizontal bar charts or any relevant chart that can present the information clearly and concisely. The prevalence of certain risk factors by demographic, genetic, and lifestyle factors of patients can be illustrated using distribution charts, box plots, violin plots, pie charts, and bar charts; although not shown in the figures, these methods are within the knowledge of a person skilled in the art.

Genetic Factors such as BRCA1, BRCA2, TP53, PALB2, and PTEN can be visualized using speedometers and gauge meters. Hormonal Factors, including estrogen and progesterone levels or hormone replacement therapy (HRT), are best depicted with horizontal bar charts and gauge meters. Environmental Factors like radiation exposure and pollutants are represented through speedometers and bar charts. Lifestyle Factors, including diet, alcohol consumption, and physical activity, can be visualized using pie charts and gauge meters. Reproductive History, such as age at first menstruation or childbirth and the number of pregnancies, is effectively shown with box plots and horizontal bar charts. Biological Factors like breast density and menopausal status are depicted with violin plots and gauge meters. Systemic Health, encompassing overall health status and comorbid conditions, is illustrated using distribution charts and horizontal bar charts. Medical History, including previous cancer diagnoses and family history of cancer, can be visualized through pie charts and bar charts.

These visualization techniques—speedometers, gauge meters, horizontal bar charts, distribution charts, box plots, violin plots, pie charts, and bar charts-offer a comprehensive and clear depiction of various factors influencing breast cancer risk and progression, facilitating thorough understanding and analysis of the data.

The Artificial Intelligence System is designed to enhance the prediction and management of users' cancer and related risks data through the integration of diverse data sources and advanced machine learning techniques.

Figure 25:
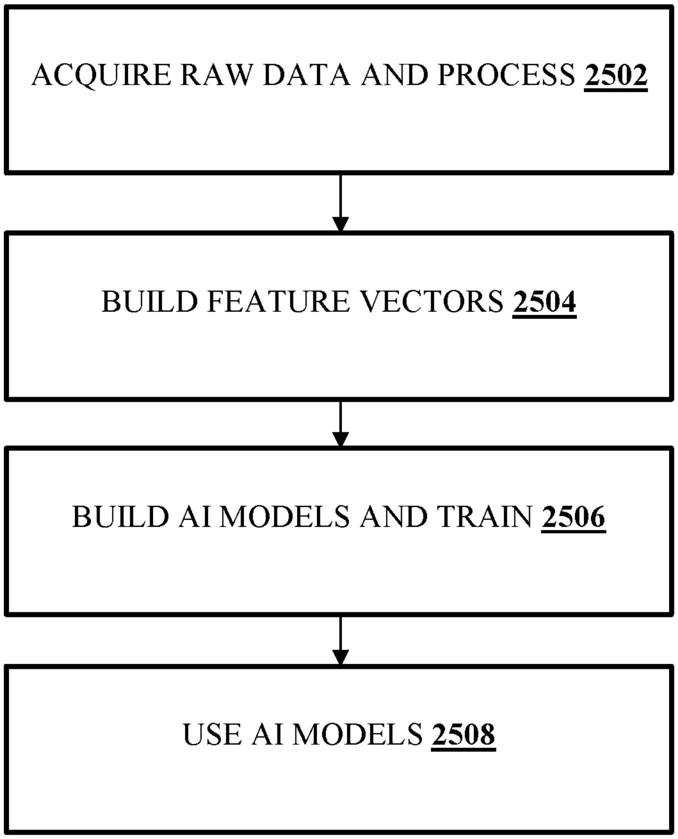
FIG. 25 shows the overall process of the AI model building according to an embodiment.

FIG. 25 shows the overall process of the AI model building according to an embodiment. The process comprise acquiring raw data and processing the data at step 2502; building a feature vector or feature vectors at step 2504; build one or more AI models and train at step 2506; and using the AI models for predicting the outputs given a set of inputs via patient record data at step 2508.

Figure 26A:
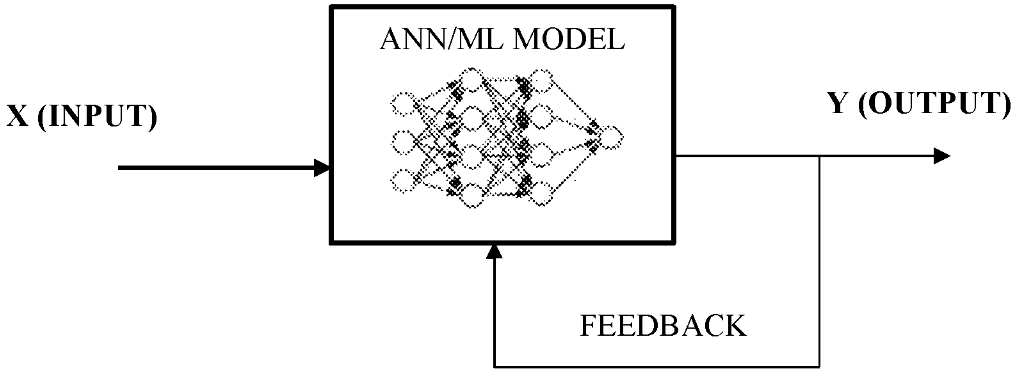
FIG. 26A shows a structure of the neural network/machine learning model with a feedback loop.

FIG. 26A shows a structure of the neural network/machine learning model with a feedback loop. Artificial neural networks (ANNs) model comprises an input layer, one or more hidden layers, and an output layer. Each node, or artificial neuron, connects to another and has an associated weight and threshold. If the output of any individual node is above the specified threshold value, that node is activated, sending data to the next layer of the network. Otherwise, no data is passed to the next layer of the network. A machine learning model or an ANN model may be trained on a set of data to take a request in the form of input data, make a prediction on that input data, and then provide a response. The model may learn from the data. Learning can be supervised learning and/or unsupervised learning and may be based on different scenarios and with different datasets. Supervised learning comprises logic using at least one of a decision tree, logistic regression, and support vector machines. Unsupervised learning comprises logic using at least one of a k-means clustering, a hierarchical clustering, a hidden Markov model, and an apriori algorithm. The output layer may predict or detect a health issue and the severity of the health issue based on the input data.

In an embodiment, ANNs may be a Deep-Neural Network (DNN), which is a multilayer tandem neural network comprising Artificial Neural Networks (ANN), Convolution Neural Networks (CNN) and Recurrent Neural Networks (RNN) that can recognize features from inputs, do an expert review, and perform actions that require predictions, creative thinking, and analytics.

In an embodiment, ANNs may be Recurrent Neural Network (RNN), which is a type of Artificial Neural Networks (ANN), which uses sequential data or time series data. Deep learning algorithms are commonly used for ordinal or temporal problems, such as language translation, Natural Language Processing (NLP), speech recognition, and image recognition, etc. Like feedforward and convolutional neural networks (CNNs), recurrent neural networks utilize training data to learn. They are distinguished by their "memory" as they take information from prior input via a feedback loop to influence the current input and output. An output from the output layer in a neural network model is fed back to the model through the feedback. The variations of weights in the hidden layer(s) will be adjusted to fit the expected outputs better, while training the model. This will allow the model to provide results with far fewer mistakes.

The neural network is featured with the feedback loop to adjust the system output dynamically as it learns from the new data. In machine learning, backpropagation and feedback loops are used to train an AI model and continuously improve it upon usage. As the incoming data that the model receives increases, there are more opportunities for the model to learn from the data. The feedback loops, or backpropagation algorithms, identify inconsistencies and feed the corrected information back into the model as an input.

Even though the AI/ML model is trained well, with large sets of labelled data and concepts, after a while, the models' performance may decline while adding new, unlabelled input due to many reasons which include, but not limited to, concept drift, recall precision degradation due to drifting away from true positives, and data drift over time. A feedback loop to the model keeps the AI results accurate and ensures that the model maintains its performance and improvement, even when new unlabelled data is assimilated. A feedback loop refers to the process by which an AI model's predicted output is reused to train new versions of the model.

Initially, when the AI/ML model is trained, a few labelled samples comprising both positive and negative examples of the concepts (for e.g., breast cancer with calcifications or no breast cancer with calcifications) are used that are meant for the model to learn. Afterward, the model is tested using unlabelled data. By using, for example, deep learning and neural networks, the model can then make predictions on whether the desired concept/s (for e.g., cancer or disease condition for an organ) are in unlabelled images. Each image is given a probability score where higher scores represent a higher level of confidence in the models' predictions. Where a model gives an image a high probability score, it is auto labelled with the predicted concept. However, in the cases where the model returns a low probability score, this input may be sent to a controller (maybe a physician) which verifies and, as necessary, corrects the result. The human moderator may be used only in exception cases. The feedback loop feeds labelled data, auto-labelled or controller-verified data back to the model dynamically and is used as training data so that the system can improve its predictions in real-time and dynamically.

Figure 26B:
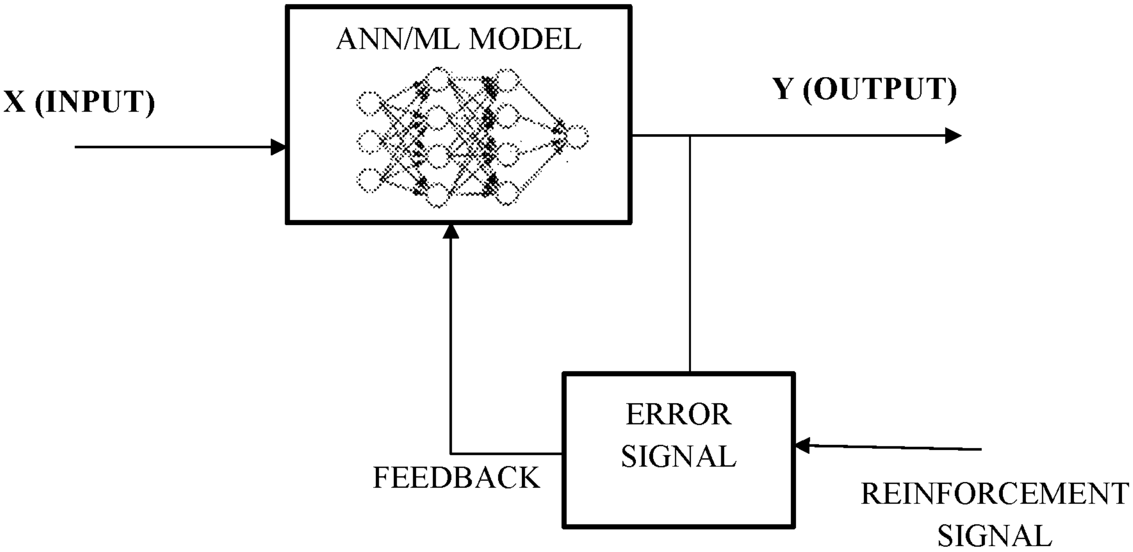
FIG. 26B shows a structure of the neural network/machine learning model with reinforcement learning.

FIG. 26B shows a structure of the neural network/machine learning model with reinforcement learning. The network receives feedback from authorized networked environments. Though the system is similar to supervised learning, the feedback obtained in this case is evaluative not instructive, which means there is no teacher as in supervised learning. After receiving the feedback, the network performs adjustments of the weights to get better predictions in the future. Machine learning techniques, like deep learning, allow models to take labelled training data and learn to recognize those concepts in subsequent data and images. The model may be fed with new data for testing, hence by feeding the model with data it has already predicted over, the training gets reinforced. If the machine learning model has a feedback loop, the learning is further reinforced with a reward for each true positive of the output of the system. Feedback loops ensure that AI results do not stagnate. By incorporating a feedback loop, the model output keeps improving dynamically and over usage/time.

All the image data, medical, clinical, historical, genetic data, external factor, SDOH and other data captured about the patient is considered as input X to the AI model and outcome of the AI model is denoted by Y which is one or more of risk to an organ of the body of the patient for example, breast, heart, lung, kidney, pancreas, eyes, brain, central nervous system, etc. The output may further comprise treatment strategies, treatment options, appointment schedule generation.

In an embodiment, graphs on a graphical user interface (GUI) for the physicians are re-arranged based on a priority score of the content of the message. The processor tracks the risk scores and contributing factors for a given patient and generates them on the display based on their contribution. Further, for each risk, the contributing factors may be displayed in decreasing importance. In an embodiment, the top 5 contributors may be shown. In an embodiment, the top 10 contributors may be shown.

According to an embodiment, disclosed is a system comprising a processor executing one or more machine learning models; wherein the processor storing instructions in a non-transitory memory that, when executed, cause the processor to receive a first input comprising an image of a breast of a patient; receive a second input comprising a patient data, wherein the patient data comprises genetic data of the patient; extract features from the image and the patient data, using the machine learning models, wherein the features comprise a presence of a calcification and a calcification pattern to generate a breast calcification vector; augment the breast calcification vector with the genetic data to generate a feature vector; determine, using the machine learning models, a first output comprising a first risk for a breast cancer; determine, using the machine learning models, a second output comprising a second risk to one or more organs of the patient, wherein the organs comprises one or more of heart, kidney, lungs, pancreas, and brain; predict, using the machine learning models, a third output comprising a third risk based on one or more of a healing response, a tumor flow and growth, inflammation and degeneration, a disease relapse, an adverse event, and a clinical response of the patient; and determine, using a statistical model, a fourth output comprising an overall risk to the patient based on the first risk, the second risk, and the third risk; wherein the machine learning models are pre-trained, wherein pre-training comprises training the machine learning models using training data from plurality of patients, wherein the training data corresponding to each patient from the plurality of patients comprises one or more of breast images, chest images, organ images, genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

According to an embodiment of the system, the image comprises one or more of mammogram image, ultrasound image, computed tomography image, and magnetic resonance image. According to an embodiment of the system, the system comprises a deep learning model for image analysis and for extracting of the features from the image.

According to an embodiment of the system, the system comprises a preprocessing module configured to normalize quality of the image across different imaging modalities.

According to an embodiment of the system, the system comprises a feature extraction module configured to extract the features from pre-processed data obtained from the image.

According to an embodiment of the system, the features comprises one or more of a ratio of fat to fiber, connective tissue density, and echogenicity of lumps. According to an embodiment of the system, the system is configured to classify a breast tissue from the image into one of several predefined categories based on the features.

According to an embodiment of the system, the fourth output is a quantified score as BRICC-G score.

According to an embodiment of the system, the presence of the calcification is identified via a calcification detection module. According to an embodiment of the system, the calcification detection module is further configured to identify and classify a type of calcification as one of ductile, vascular, and parenchymal calcification. According to an embodiment of the system, the calcification detection module is further configured to quantify the calcification to provide an assessment of reversibility. According to an embodiment of the system, the calcification pattern comprises one of more modules comprising deep learning models to determine one or more of a location, a spread, a nature, a size, a shape, a density, an anatomy, a distribution, an involvement, a continuity, an etiologic, and a characterization of breast arterial calcifications. Parenchymal calcification refers to the deposition of calcium salts within the parenchyma, the functional tissue of an organ. This condition can occur in various organs, such as the lungs, liver, kidneys, and brain. It is often a sign of previous injury, inflammation, infection, or a metabolic disorder. The calcifications can be detected through imaging techniques like X-rays, CT scans, or MRIs. While they are sometimes incidental findings with no clinical significance, parenchymal calcifications can also indicate underlying pathology that may require further investigation and management.

According to an embodiment of the system, the system further comprises a spread detection module configured to detect the spread of abnormalities within the image and determine a quantifying measure by generating a spread index representing an extent of each abnormality of the abnormalities.

According to an embodiment of the system, the system further comprises a malignant detection module configured to detect the nature of the calcification pattern, wherein the nature is one of a benign and a malignant; and wherein the nature of the calcification pattern is detected based on the features extracted from textural and morphological data; and wherein the nature of the calcification pattern is classified as one of normality and abnormality.

According to an embodiment of the system, the system further comprises a size characterization module, wherein the size characterization module is configured to calculate the size comprising a dimension and output the dimension of the calcification.

According to an embodiment of the system, the system further comprises a shape detection module configured to determine geometric properties that define the shape of abnormalities; and quantify characteristics of the shape of the calcification.

According to an embodiment of the system, the system further comprises a tissue density prediction module for density levels of tissue configured to determine the density by processing the image to evaluate the density of a tissue and determine levels of the density.

According to an embodiment of the system, the system further comprises an anatomy prediction module configured for mapping anatomical features, identify anatomical landmarks and relation of anatomical features and the anatomical landmarks to normalities and abnormalities to determine mapping data of the anatomy. According to an embodiment of the system, the system further comprises an abnormality distribution assessment module for evaluating the distribution of abnormalities within a tissue of the breast and extracting a summary of the distribution.

According to an embodiment of the system, the system further comprises an involvement assessment module for detecting the involvement of abnormalities with surrounding tissues for analyzing the image to determine abnormalities interacting or invading adjacent tissues and output involvement data.

According to an embodiment of the system, the system further comprises a continuity assessment module for assessing the continuity of abnormalities in tissues for determining abnormalities as isolated or continuous with other tissue structures for the image; output continuity data.

According to an embodiment of the system, the system further comprises an etiologic module for determining etiologic factors of abnormalities in the image to determine potential causes or contributing factors of the abnormalities and output etiologic data.

According to an embodiment of the system, the system further comprises a characterizing module for the characterization of abnormalities to provide a profile of the abnormalities and output characterization data.

According to an embodiment of the system, the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A, BRCA 1, BRCA 2, PTEN, PALB 2, TP53, ATM, RB, CDH1, CHDI2, CHEK2, NF1, NBN, STK11, MSI, BARD, BRIPRAD, POLE, TNF, IL6, IL1beta, MMP3, COL2A1, APOE, PSEN1, SNAK, PARKIN, HLA, NOD2.

According to an embodiment of the system, the second risk comprises one or more of cardiovascular risk, cardiac contractile risk, cardiac rhythm risk, renovascular and renal perfusion risk, retinopathy risk, pancreatic risk, cerebrovascular and CNS health risk, pulmonary risk, chronic disease risk, vascular perfusion risk.

Figure 27:
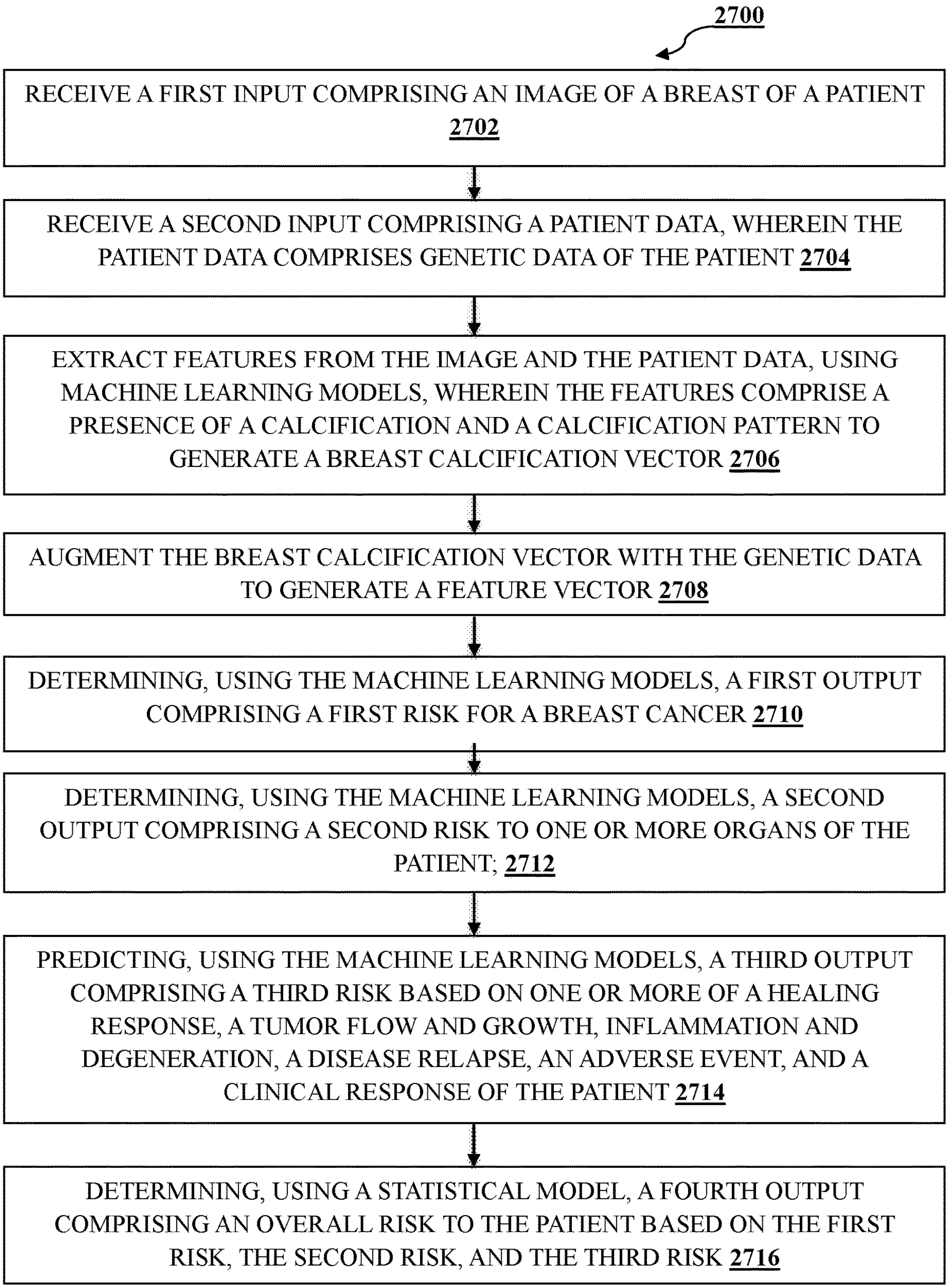
FIG. 27 shows method steps for an AI based comprehensive risk prediction system according to an embodiment

FIG. 27 shows method steps for an AI based comprehensive risk prediction system according to an embodiment. According to an embodiment, disclosed is a method 2700 comprising receiving a first input comprising an image of a breast of a patient at step 2702; receiving a second input comprising a patient data, wherein the patient data comprises genetic data of the patient at step 2704; extracting features from the image and the patient data, using machine learning models, wherein the features comprise a presence of a calcification and a calcification pattern to generate a breast calcification vector at step 2706; augmenting the breast calcification vector with the genetic data to generate a feature vector at step 2708; determining, using the machine learning models, a first output comprising a first risk for a breast cancer at step 2710; determining, using the machine learning models, a second output comprising a second risk to one or more organs of the patient, wherein the organs comprises one or more of a heart, a kidney, lungs, a pancreas, and a brain of the patient at step 2712; predicting, using the machine learning models, a third output comprising a third risk based on one or more of a healing response, a tumor flow and growth, inflammation and degeneration, a disease relapse, an adverse event, and a clinical response of the patient at step 2714; and determining, using a statistical model, a fourth output comprising an overall risk to the patient based on the first risk, the second risk, and the third risk at step 2716; wherein the machine learning models are pre-trained, wherein pre-training comprises training the machine learning models using training data from plurality of patients, wherein the training data corresponding to each patient from the plurality of patients comprises one or more of breast images, chest images, organ images, genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

According to an embodiment of the method, the image comprises one or more of mammogram image, ultrasound image, computed tomography image, and magnetic resonance image. According to an embodiment of the method, the calcification pattern comprises one of more modules comprising deep learning models to determine one or more of a location, a spread, a nature, a size, a shape, a density, an anatomy, a distribution, an involvement, a continuity, an etiologic, and a characterization of breast arterial calcifications. According to an embodiment of the method, the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A, BRCA 1, BRCA 2, PTEN, PALB 2, TP53, ATM, RB, CDH1, CHDI2, CHEK2, NF1, NBN, STK11, MSI, BARD, BRIPRAD, POLE, TNF, IL6&1beta, MMP3, COL2A1, APOE, PSEN1, SNAK, PARKIN, HLA, NOD2.

According to an embodiment of the method, the second risk comprises one or more of cardiovascular risk, cardiac contractile risk, cardiac rhythm risk, renovascular and renal perfusion risk, retinopathy risk, pancreatic risk, cerebrovascular and CNS health risk, pulmonary risk, chronic disease risk, vascular perfusion risk.

According to an embodiment, disclosed is a non-transitory computer-readable medium having stored thereon instructions executable by a computer system to perform operations comprising, receiving a first input comprising an image of a breast of a patient; receiving a second input comprising a patient data, wherein the patient data comprises genetic data of the patient; extracting features from the image and the patient data, using machine learning models, wherein the features comprise a presence of a calcification and a calcification pattern to generate a breast calcification vector; augmenting the breast calcification vector with the genetic data to generate a feature vector; determining, using the machine learning models, a first output comprising a first risk for a breast cancer; determining, using the machine learning models, a second output comprising a second risk to one or more organs of the patient, wherein the organs comprises one or more of a heart, a kidney, lungs, a pancreas, and a brain of the patient; predicting, using the machine learning models, a third output comprising a third risk based on one or more of a healing response, a tumor flow and growth, inflammation and degeneration, a disease relapse, an adverse event, and a clinical response of the patient; and determining, using a statistical model, a fourth output comprising an overall risk to the patient based on the first risk, the second risk, and the third risk; wherein the machine learning models are pre-trained, wherein pre-training comprises training the machine learning models using training data from plurality of patients, wherein the training data corresponding to each patient from the plurality of patients comprises one or more of breast images, chest images, organ images, genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

According to the non-transitory computer-readable medium, the image comprises one or more of mammogram image, ultrasound image, computed tomography image, and magnetic resonance image. According to the non-transitory computer-readable medium, the genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A, BRCA 1, BRCA 2, PTEN, PALB 2, TP53, ATM, RB, CDH1, CHDI2, CHEK2, NF1, NBN, STK11, MSI, BARD, BRIPRAD, POLE, TNF, IL6, IL1beta, MMP3, COL2A1, APOE, PSEN1, SNAK, PARKIN, HLA, NOD2.

Figure 28:
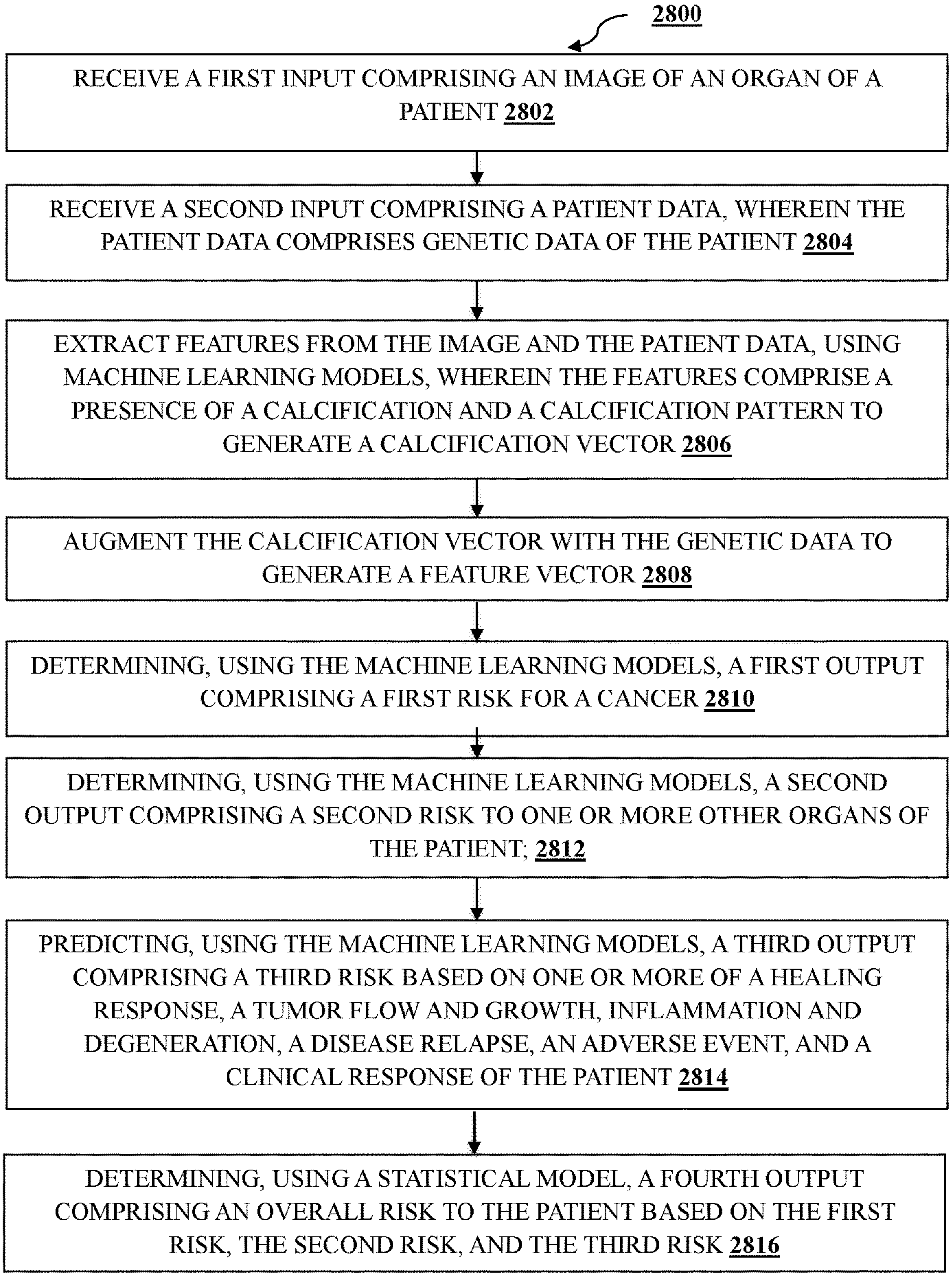
FIG. 28 shows method steps for an AI based comprehensive risk prediction system according to an embodiment

FIG. 28 shows method steps for an AI based comprehensive risk prediction system according to an embodiment. According to an embodiment, disclosed is a method 2800 comprising receiving a first input comprising an image of an organ of a patient at step 2802; receiving a second input comprising a patient data, wherein the patient data comprises genetic data of the patient at step 2804; extracting features from the image and the patient data, using machine learning models, wherein the features comprise a presence of a calcification and a calcification pattern to generate a calcification vector at step 2806; augmenting the calcification vector with the genetic data to generate a feature vector at step 2808; determining, using the machine learning models, a first output comprising a first risk for a cancer at step 2810; determining, using the machine learning models, a second output comprising a second risk to one or more other organs of the patient, wherein the other organs comprises one or more of a breast, a heart, a kidney, lungs, a pancreas, and a brain of the patient at step 2812; predicting, using the machine learning models, a third output comprising a third risk based on one or more of a healing response, a tumor flow and growth, inflammation and degeneration, a disease relapse, an adverse event, and a clinical response of the patient at step 2814; and determining, using a statistical model, a fourth output comprising an overall risk to the patient based on the first risk, the second risk, and the third risk at step 2816; wherein the machine learning models are pre-trained, wherein pre-training comprises training the machine learning models using training data from plurality of patients, wherein the training data corresponding to each patient from the plurality of patients comprises one or more of breast images, chest images, organ images, genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

How Technical Solution is a Technological Advancement:

The technical solution represents a technological advancement by addressing the limitations of existing breast cancer detection methodologies and introducing a comprehensive health assessment capability. The integration of multi-modal data sources and advanced AI techniques into a single diagnostic platform enhances the precision and scope of patient evaluations. This innovation not only improves early cancer detection rates but also empowers healthcare providers with actionable insights into broader health risks, thereby advancing the standard of care in oncology and preventive medicine.

BRICC-G Score Integration: As used herein BRICC-G score, Breast Imaging-Computed Comprehensive—Genomics score that is an overall score from the AI based model. The BRICC-G score leverages a comprehensive framework integrating mammographic image data with genetic markers, clinical data, and laboratory results to assess health status. This multi-faceted approach allows for detailed and accurate cardiovascular health prediction, demonstrating the advantages of an integrated model over isolated independent models. BRICC-G score can be in a predefined range such as 0-1, 0-10, 0-100 etc. It may be quantitative or qualitative measure for example the 0-1 score may be subdivided as 0-3 as low risk; 4-6 as medium risk; 6-8 as high risk; 9-10 as severe risk. The risk stratification is illustrated as an example, but such a stratification is made and used.

In an embodiment, the system comprises at least three machine learning modules, first module to determine a calcification and calcification pattern and predict risk of breast cancer, second module to predict risk to any other organ, and third module predicting healing, clinical response, etc. Each module may comprise one or more machine learning models.

The three modules have certain features unique to each of the groups and have three different sets of outcomes for assessment for each risk. Further, one outcome of the module is passed as input to the other module trained on the same set of features thereby rendering a fine-tuned customized outcome. Within each module, the models may be interconnected and use the same set of features to predict/detect different outcomes, or each model may have unique features and one model passes its output to the other mode.

The assessment of an individual's health status involves a complex interplay of various factors, including genetic markers, clinical parameters, imaging data, and laboratory results. An integrated approach that considers these interconnected elements offers a more comprehensive and accurate assessment of health risks for different conditions. Contextual analysis of the interactions among diverse health indicators can uncover intricate patterns and relationships, providing deeper insights into overall health risks.

By combining multiple data sources within a unified framework, the synergistic effects of these variables are captured, leading to more precise predictions and the elimination of redundancies. This results in a balanced and personalized health score that can be dynamically updated as new data becomes available. Such an integrated model facilitates advanced feature analysis to identify the most influential factors for various health risks, enabling targeted interventions and personalized medicine.

The unified framework ensures methodological consistency and streamlines the generation of the health score, reducing complexity and potential errors associated with using multiple models. This comprehensive assessment can evaluate risks related to cardiovascular health, renovascular health, neurological health, cancer, as well as inflammatory and degenerative conditions, including predicting outcomes such as cardiac contractile issues, cardiac rhythm problems, renal function, cerebrovascular health, cancer progression, and the impact of chronic conditions like diabetes and hypertension.

An integrative approach that combines genomics, proteomics, microbiomics, and clinical data, and applies AI algorithms to extract valuable patterns and insights, can enhance decision-making processes and guide more personalized and effective interventions. This multidisciplinary collaboration between medical practitioners, biologists, data scientists, and other experts is essential in refining AI models and ensuring their robustness, reliability, and ethical soundness. By harnessing the power of AI-driven predictive modeling, healthcare providers can navigate the complexities of precision medicine and offer tailored solutions to improve patient outcomes.

Need for comprehensive model for assessing a health risk in a cancer patient:

1. Holistic Health Assessment

Interconnected Health Indicators: Cardiovascular health is influenced by various interconnected factors, including genetic markers, clinical parameters, imaging data, and laboratory results. An integrated approach ensures that all these factors are considered together, providing a more comprehensive and accurate health assessment.

Contextual Analysis: The interactions between different health indicators can reveal complex patterns and relationships that independent models might miss, ensuring a thorough understanding of cardiovascular health.

2. Improved Predictive Accuracy

Data Integration Synergy: Combining multiple data sources in a single model captures the synergistic effects of these variables, leading to more accurate predictions than independent models.

Reduction of Redundancies: An integrated model can identify and eliminate redundancies across different data sources, ensuring a balanced and accurate health score.

3. Personalized Medicine

Tailored Health Scores: A comprehensive model provides personalized health scores by considering the unique combination of factors present in each individual.

Dynamic Adjustment: This approach allows for dynamic adjustment of the health score as new data becomes available, ensuring relevance and accuracy.

4. Consistency and Cohesion

Unified Framework: Using a single integrated model ensures methodological consistency and cohesive interpretation of results, crucial for clinical decision-making.

Streamlined Process: An integrated approach simplifies the generation of the health score, reducing complexity and potential errors associated with multiple models.

5. Advanced Analytical Capabilities

Comprehensive Feature Analysis: An integrated model performs advanced feature analysis, identifying the most significant predictors of cardiovascular health from a vast array of data inputs.

Complex Interactions: It handles complex interactions between variables, such as the interplay between genetic factors and clinical symptoms, providing nuanced predictions.

6. Resource Efficiency

Optimized Resource Use: Running a single comprehensive model is more resource-efficient than maintaining multiple independent models, reducing computational overhead and simplifying data management.

Centralized Data Management: Centralized processing of data in an integrated model makes it easier to update and maintain as new research and data become available.

7. Enhanced Clinical Utility

Actionable Insights: By integrating diverse data sources, the model provides more actionable insights, aiding clinicians in informed decision-making.

Predictive and Preventive Measures: It enables the development of tailored predictive and preventive measures, improving healthcare interventions' overall effectiveness.

In a comprehensive review of patient records aimed at evaluating mortality and morbidity, a pattern has emerged that warranted further investigation. Regular examinations are conducted to scrutinize any unexplained cases, delving deeply into the medical histories of affected individuals. While the death of a stage four cancer patient may be anticipated, the demise of a stage one patient prompts a critical reassessment of preventive measures. During one such exercise, an unexpected trend was observed where individuals aged 35 to 50 years experienced sudden cardiac arrests despite having no prior indications of heart disease. Detailed examinations, including assessments of heart pumping function and ECG rhythm analyses, revealed that these individuals had hearts in excellent condition, complicating the understanding of their sudden cardiac events. This anomaly suggests the necessity for an expanded scope of investigation to uncover underlying factors that conventional evaluations might overlook. The occurrence of sudden cardiac arrests in these patients was surprising upon reviewing their medical records. Analyzing these records revealed a peculiar pattern, the mammograms indicated the presence of calcium deposits in the blood vessels.

Angiograms are not routinely performed before chemotherapy due to the extensive nature of the investigation and lack of global recommendation. However, a review of patients who experienced sudden cardiac arrests revealed subtle abnormalities, with the blood vessels in the breast having a similar caliber to coronary vessels. This observation prompted an investigation into young deaths among breast cancer patients, finding that 8 out of 10 patients had calcium deposits in their blood vessels. A larger study of 3,800 mammograms showed calcifications in 10-11% of women. Further angiograms on 78 of these women revealed blocked arteries, leading to proactive heart attack prevention measures. This discovery underscores the higher risk of heart attacks in women with calcifications, especially those with specific genetic, lipid, lifestyle, or body mass index factors.

Not every calcification poses a risk for heart attacks, as demonstrated by an extensive analysis of data using clinical information and specific genetic markers. The study revealed that calcifications not only impact heart health but also extend to compromised kidney and brain circulation, predicting risks to these organs. This finding is unprecedented, as prior studies primarily focused on linking calcifications to cardiac risk without delving into the specific characteristics that differentiate true risk factors. For example, when you see deeper calcifications along with other factors, then such cases may have the cardiovascular risk.

Research at the facility is focused on identifying temporal correlations to quantify the risk of developing conditions such as heart attacks, kidney issues, or stroke. There is supporting data on increased risk among breast and cervical cancer patients with calcifications compared to those without, and the conclusion on the risk lies in the combination of genetic factors and clinical laboratory characteristics such as CA15.3, CRP levels, and Cpk levels. The scoring model is based on the levels of these various input factors and associated calcification analysis results.

In an embodiment, alternative imaging methods are suggested for individuals who cannot undergo mammograms due to reasons such as dense breast tissue. This includes utilizing ultrasound and MRI, where the methods and analysis techniques are adapted to detect features analogous to calcifications, termed 'T2-weighted lesions' in MRI scans and utilizing Doppler ultrasound to assess blood flow. Each of these imaging modalities provides valuable insights that, when applied with calcification-equivalent criteria, enriches diagnostic capabilities significantly, calcification equivalent criteria comprises one or more of Coronary artery calcium scoring from Computed Tomography, Time-of-flight (TOF) magnetic resonance angiography (MRA) that visualizes blood flow which might be affected by calcification (therefore obstruction to blood flow can act as a proxy or surrogate for calcification), in case of ultrasound, acoustic shadows that are characteristics of calcified plaques can be used, in PET (Positron Emission Tomography) 18F-Sodium Fluoride can provide signals for calcification. calcification equivalent criteria means any signal captured from other imaging modalities that can be used as proxy for calcification in X-ray imaging/mammograms.

In an embodiment, the calcification or calcification equivalent criteria with the combination of genetic factors and clinical factors of the patient are used to classify the patients into various groups and are assigned risk scores based on these combination factors. Further they can be used to classify the risk at the organ level and at the overall patient level.

The AI model explores the unique genetic contributions and lab parameters and how these combinations work in determining whether a certain organ is at risk or not, whether a patient will heal or not, whether relapse happens or not, etc. There are studies on the correlation between calcification seen in mammograms and coronary artery disease, however, there is no system available to determine whether a specific patient with a given calcification pattern and combination of other factors is a risk (of any organ or as a whole) or not.

The presence and nature of calcifications in patients can be influenced by several factors. Firstly, calcifications may arise due to benign reasons unrelated to any underlying health conditions or treatments. However, if calcifications occur on necrotic/dead cells or inflamed cells, this is termed opportunistic calcification, which is not good and can exacerbate under conditions of inflammation. The type and behavior of calcifications are largely influenced by the individual patient's genetic makeup, lifestyle, and inherent characteristics. It is the uniqueness of the patient that determines what type of calcification the patient is likely to have and how it is going to behave. For instance, genetic predispositions or specific lifestyle factors can determine the likelihood and type of calcification a patient may develop.

In the context of breast cancer treatment, some therapies may induce inflammation, potentially increasing the risk of calcifications. However, this effect is not universal and occurs only in specific subsets of patients. Therefore, while cancer treatments can influence calcification risk, the fundamental determinants remain unique to the patient and are based on genetic and lifestyle traits of the patient.

In an embodiment, it is a system for assessment and monitoring of cancer with projections onto cardiovascular risk. The system takes the breast images as the input, which are called mammograms, which are like the basic fundamental screening element along with other factors such as patient characteristics, medical data, and clinical data.

Artificial Intelligence/Machine learning (AI/ML) models offer enhanced capabilities for analyzing mammograms and categorizing calcifications more effectively. Simultaneously monitoring calcifications over the treatment duration allows for early detection and proactive management.

By monitoring both cancer development and vascular risks concurrently, the system not only is monitoring dual risk but also leveraging insights between these interconnected health indicators. This integrated approach enhances the system's ability to comprehend underlying factors that influence both risks. In an embodiment, instead of dual risk monitoring, the system can be trained for multi risk monitoring and leveraging insights among these interconnected health indicators. This integrated approach enhances the system's ability to comprehend underlying factors that influence multiple risks.

The system is configured to concurrently monitor two risks, while attempting to extrapolate insights from one to inform understanding of the other. Predicting cancer from calcifications is known in prior research. However, investigating how cancer develops and progresses based on specific characteristics of both the cancer and the calcifications, thereby identifying cancer type and progression dynamics is not explored or well known. The AI based system predicts how soon the cancer develops, what specific characteristics of the calcification makes it develop and what type of cancer it is. When examining vascular aspects, they are notably greedy. In an embodiment, image analytics are employed to reveal insights for understanding the origins of calcification, its potential reversibility, and whether it impacts other organs is a domain largely unexplored until now.

In an embodiment, the system determines/predicts the temporal sequence of events, identifies the type of cancer, and assesses whether the wound heals. The first analysis involves characterizing the calcifications and gathering detailed information about them. The next step involves monitoring these elements alongside genetic data and projecting cancer risk to vascular risks. A projection from one risk to the other risk means the information that was collected for one risk, i.e., breast cancer prediction, gives deep insights to manage other risks, for example vascular risks.

BRICC-G is performed to quantify the risks by means of a score. BRICC-G is a score for comprehensive assessment of both cancer, vascular risk, and risk to other organs.

In an embodiment, a patient's digital information is collected, monitored over multiple visits to understand the progression of cardiac risk/any other organ risk and to train the AI model.

In an embodiment, each module may be configured to predict a score for a single risk such as breast cancer risk, cardiovascular risk, pancreatic risk etc., and to have a comprehensive assessment for all the cancers and determine an overall score.

The framework with well-trained AI modules are provided with a mammogram image, to quantify the calcification, to predict the biology of the lesions and embed them with genetic markers, collect the genetic markers from the patient, enter the information, to perform overall health assessment and have an additional support system that can assist the clinicians in preparing treatment plans, as well as the care management.

While most breast imaging has been done using conventional mammograms, the system can also read and analyze images from other imaging modalities. The input can be one or more of imaging or genetic data, such as genetic markers. The system determines each patient's risk of cardiovascular disease. If genetic information is provided, the predictions will be more accurate, but even basic lab data is sufficient to provide a prediction. Basic lab data refers to standard tests like blood counts, metabolic panels, lipid profiles, urinalysis, and other tests that provide essential health information. The models will improve with genetic data but can still predict with just basic data of image and basic health data.

In an embodiment, the input set of features considered for each risk may be determined using a statistical analysis where a p-value threshold is used to determine which factors or features are used to train the AI model. A p-value is a statistical measure used in hypothesis testing to determine the significance of the observed results. It quantifies the probability of obtaining results at least as extreme as those observed, assuming that the null hypothesis is true. The significance of the p-value lies in its ability to help researchers decide whether to reject the null hypothesis. A commonly used threshold is 0.05; if the p-value is below this threshold, it suggests that the observed data is unlikely to have occurred by chance, leading to the rejection of the null hypothesis and indicating a statistically significant result. Conversely, a p-value above 0.05 suggests that there is not enough evidence to reject the null hypothesis, implying that the observed effect could be due to chance. However, the p-value is interpreted in the context of the study, considering factors like sample size, effect size, and study design, to make a well-informed conclusion about the significance of the results.

The issue is not specifically about cancer or heart disease but rather about how calcium behaves. The pattern of calcification helps to determine whether a woman, or even a man, is likely to develop cancer. The system is designed to understand the unique patterns of calcification seen in mammograms and their implications for diseases like cancer and vascular disease. If a calcification pattern is observed in a mammogram, it can indicate potential issues not just in the breast but also in other organs such as the kidneys, heart, or brain. The analysis relies on imaging, with the ability to predict various health issues based on these patterns. Routine breast imaging, commonly done during annual health checks for women, can potentially generate input to predict other cancers automatically at the end of these checkups.

This prediction is based on the calcification patterns in different organs. The approach is generalized to any organ's image to predict cancer risk.

When examining the data, it becomes apparent that there are two distinct streams: one focused on patient-specific data and the other on aggregated patient data. The first stream involves data unique to the individual patient, such as mammograms, genetic information, and other personal health records. The model uses this data to make predictions, monitor the actual outcomes against the predictions, analyze discrepancies, and subsequently refine its predictive capabilities for that specific patient. The second stream encompasses data from a collection of patients. When a new patient arrives with limited personal data, such as only a mammogram, the model relies on the collective data from similar patients to make initial predictions. The model for this patient is then continuously improved based on their specific data over time. Thus, the system operates with two complementary models: a generic model that is enhanced through collective patient data and a personalized model that evolves with the individual patient's data. This dual-stream approach ensures robust predictive accuracy and continuous model improvement.

Further the system provides two streams of analysis: one that is specific to the individual patient and another that is based on collective information from multiple patients, including data from multiple visits. This distinction allows for targeted analysis of demographics to identify which groups are more prone to correlations between cancer and cardiovascular risk. Such demographic analysis serves a different purpose compared to individualized diagnosis and treatment.

According to an embodiment, it is an AI powered System for Assessment and Monitoring of Cancer and Cardio/Vascular Risk using Multimodal Breast Data with emphasis on calcification.

The invention pertains to the field of medical imaging analysis, specifically to an integrated system that applies advanced deep learning techniques to assess breast cancer risk and vascular(coronary) health indicators from various imaging modalities/laboratory tests and Patient Characteristics. The assessment in the form of a BRICC-G score can be used to interpret the health condition and identify individuals with cancer and vascular risk.

According to an embodiment, the system is designed to address several gaps in current breast imaging analysis, including the challenge of diagnosing dense breast tissue, characterizing calcifications, conducting integrated temporal analyses, and creating multi-modal risk assessments.

According to an embodiment, the system is designed as a comprehensive analytical system that employs deep learning algorithms, particularly convolutional neural networks (CNNs), to evaluate breast imaging for cancer diagnostics and vascular(coronary) health assessment. The system utilizes data from multiple imaging techniques, incorporates patient-specific genetic, clinical and biochemical data, and calculates a multi-dimensional risk score to inform clinical decisions. It includes methodologies for data acquisition, model selection, preprocessing, feature extraction, and integration and prediction of histological information, besides vascular health and malignant transformations. The model's validation ensures accurate detection and diagnosis, and its clinical integration allows for timely and improved patient outcomes.

AI powered Analytical System: Incorporating cardio/vascular (coronary) health indicators into breast imaging analysis not only promises to transform breast cancer management but also opens avenues for early detection of vascular (cardiac) issues, allowing for timely interventions.

According to an embodiment, it is a system comprising Advanced Imaging Analysis Encompassing Coronary Health.

Dual-Feature Detection: An advanced system that can not only differentiate between benign and malignant breast lesions but can also classify the breast lesions to predict the biological markers (hormonal status/grade/heal potential) and also identify markers suggestive of vascular disease, such as coronary, renal and cerebral and critical organs having dependency on vascular supply.

Sequential Imaging for Breast and Cardiac Health Monitoring: A comprehensive analytical tool that evaluates sequential imaging to provide insights into both breast lesion dynamics and coronary health, influencing preventive cardiology in cancer patients.

Combined Breast and Coronary Risk Profiling: A sophisticated model that integrates imaging with genomic, demographic, biochemical markers, and lifestyle factors to evaluate and predict breast cancer and coronary health risks.

Comprehensive Decision Support Systems: Decision-making tools that assist clinicians in interpreting complex data to optimize patient management, encompassing both oncological and cardiovascular care.

According to an embodiment, the system performs a multi-modal imaging assessment, integrating advanced imaging techniques with patient-specific genetic and clinical data to determine a nuanced Breast Calcification Score. This BRICC-G score provides insights into malignancy risk and vascular health, guiding personalized treatment strategies. The system is configured to: i) provide diagnostics for breast tissues and associated cardiac risk; ii) characterize calcifications for breast and vascular health; iii) temporal analysis to monitor disease progression and cardiac health; iv) multi-modal data integration for comprehensive risk assessment; v) personalized treatment plans for holistic health management through calcification analysis for pathological insight.

The system computes several Risk Scores

Breast Calcification Score: Evaluates malignancy risk and cardio/vascular health based on imaging and patient data. Derived from factors like calcification size, shape, density, and distribution. Informs on tumor aggressiveness, post-surgery healing, and recurrence risk.

Reversibility Score and Vascular Health: Indicates the potential to reverse cardiovascular risk factors through lifestyle changes. Comprises modifiable cardiovascular risk factors such as hypertension, obesity, and hyperlipidemia. Assessed based on lifestyle interventions like diet, exercise, and medication adherence, rhythm, contractility of heart, renal health, CNS health, Orgon health (having dependency on vascular supply).

The present invention establishes a comprehensive and systematic methodology for evaluating breast imaging, encompassing mammograms, ultrasound, computed tomography (CT) scans, MRI, thermography, and standard clinical photographs. The focus of this analysis is to meticulously quantify breast calcifications, examining parameters such as size, shape, composition, density, and distribution, as well as the accompanying parenchymal alterations, the dynamics of regression or progression, temporal variations, involvement of surrounding tissues, and the overall calcification load. Upon garnering detailed insights into the characteristics of breast calcifications, the method synergistically incorporates additional patient-specific data, including genetic profiles, demographic factors, clinical histories, laboratory biochemistry, and serum oncological markers, alongside indicators of vascular risk (cardio, cerebral, renal, other organs). This integration culminates in the derivation of a nuanced Breast Calcification Score, indicative of lesion biology (grade, Hormonal status, HER-2 status, maligned efficient, healing potential) and cardio/vascular health. The score further encompasses an organ-level perfusion health assessment, contributing to the formulation of personalized preventive and therapeutic strategies. This innovative system empowers clinicians by enabling the prediction of histomorphology features derived from the aforementioned imaging modalities, thereby enhancing the clinical decision-making process for patient care management.

This invention encapsulates a transformative approach in cancer risk modeling, enabling personalized treatment strategies through its multifaceted analysis of tumor behavior, calcification patterns, and integration of patient-specific data.

By harnessing the power of AI and machine learning, the system offers a novel diagnostic tool that enhances the precision of cancer treatment and opens avenues for addressing vascular health, exemplifying a significant advancement in patient-centric healthcare.

The invention is built upon several foundational Techniques

Tumor Growth and Treatment Strategies: The system differentiates tumors, providing insights into their growth rate, calcification characteristics, and metabolic demands, which guide the selection of suitable interventions such as radiation or chemotherapy. Aids in determining post-surgery healing prospects by analyzing calcification patterns, crucial for tailoring post-operative care and improving patient outcomes.

Inflammation and Disease Recurrence: Detects inflammatory calcifications, serving as indicators of ongoing inflammation and potential disease recurrence, enabling early intervention strategies and close monitoring for timely detection of recurrence.

Data acquisition, Model Training and Validation: Employs a rigorous process of data acquisition and preparation, involving the collection of a diverse dataset of mammogram images to train the CNN model. Selects optimal CNN architecture and applies preprocessing techniques to standardize image data, followed by feature extraction that informs cancer indicators. Integrates histological information, enhances model prediction capabilities, and validates performance using accuracy, sensitivity, specificity, and AUC metrics.

Clinical Integration and Potential Impact: Upon validation, the model is set to be integrated into clinical workflows, assisting clinicians and pathologists in making accurate and timely diagnoses, which could significantly improve patient outcomes. The system's potential extends beyond cancer diagnostics by incorporating a reversibility score that addresses cardiovascular risk factors, underscoring its role in preventive healthcare.

An AI powered system comprising a processor executing a deep learning model for Image analysis; a processor executing a machine learning model augmenting data; a processor executing a risk assessment machine learning model; a database comprising a plurality of patient record data; and wherein the system is operable to acquire, by the processor, the plurality of patient record data from the database, wherein the patient record data comprises a demographic, genetics, clinical, clinicians note as text data and a breast image data; pre-process, by the processor, for segregating and preprocessing the patient record data into a structured data with demographic, genetics, clinical information and an unstructured data with clinical notes and breast image to make them ready for machine learning and deep learning operations; and generate, by the processor, the machine learning model including all the structured data.

Train, by the processor, the machine learning model with the patient record data; generate, by the processor, the deep learning model all the breast image data of different image modalities.

Train, by the processor, the deep learning model with the breast image data; generate, by the processor, the cardiovascular risk assessment machine learning model with outcomes from machine learning model and deep learning model.

Train, by the processor, the cardiovascular risk assessment machine learning model with the breast image data augmented with other patient medical, clinical characteristics.

Train, by the processor, the Kidney and the blood vessels risk assessment machine learning model with the breast image data augmented with other patient demographic medical, clinical and genetic characteristics.

Train, by the processor, the Retina risk assessment machine learning model with the breast image data augmented with other patient demographic medical, clinical and genetic characteristics.

Train, by the processor, the Pancreatic Diseases and Cancer risk assessment machine learning model with the breast image data augmented with other patient demographic medical, clinical and genetic characteristics.

Train, by the processor, the Neurological and Cerebrovascular health risk assessment machine learning model with the breast image data augmented with other patient demographic medical, clinical and genetic characteristics.

Train, by the processor, the Lung function and COPD risk assessment machine learning model with the breast image data augmented with other patient demographic medical, clinical and genetic characteristics.

Train, by the processor, the Chronic Disease risk assessment machine learning model with the breast image data augmented with other patient demographic medical, clinical and genetic characteristics.

Train, by the processor, the Critical Vascular Perfusion risk assessment machine learning model with the breast image data augmented with other patient demographic medical, clinical and genetic characteristics.

Train, by the processor, the Healing assessment machine learning model with the breast image data augmented with other patient demographic medical, clinical and genetic characteristics.

Train, by the processor, the Tumor Flow and Growth assessment machine learning model with the breast image data augmented with other patient demographic medical, clinical and genetic characteristics.

Train, by the processor, the Inflammation/Degeneration assessment machine learning model with the breast image data augmented with other patient demographic medical, clinical and genetic characteristics.

Train, by the processor, the Adverse Events assessment machine learning model with the breast image data augmented with other patient demographic medical, clinical and genetic characteristics.

Train, by the processor, the Clinical Response assessment machine learning model with the breast image data augmented with other patient demographic medical, clinical and genetic characteristics.

According to an embodiment, the system comprises a data reception module configured to: receive breast image data from one or more imaging modalities, including at least one of mammograms, ultrasound, computed tomography (CT), and magnetic resonance imaging (MRI).

According to an embodiment, the system comprises a preprocessing module configured to: Normalize image quality across different imaging modalities of the received breast image data, preparing the data for further analysis.

According to an embodiment, the system comprises a feature extraction module configured to: Extract features from the pre-processed breast image data, where the features include, but are not limited to, the ratio of fat to Fiber, connective tissue density, and echogenicity of lumps.

According to an embodiment, the system comprises an AI-based model configured to: classify the breast tissue into one of several predefined categories based on the extracted features using an artificial intelligence (AI) model.

According to an embodiment, the system comprises a calcification detection module configured to: Detect the presence of calcification within the mammogram using the AI model. Further, identify the type of calcification as one of ductile, vascular, or parenchymal calcifications, if calcification is detected. Quantify the detected calcification to provide an assessment of its reversibility.

According to an embodiment, the system comprises a spread detection module configured to: Detect the spread of abnormalities within the mammograms using the AI model. Further, quantifying by generating a spread index representing the extent of each abnormality.

According to an embodiment, the system comprises a malignant (nature) detection module configured to: Employing a machine learning model trained to distinguish between benign and malignant features based on textural and morphological data; thus, classifying the nature of each detected normality or abnormality.

According to an embodiment, the system comprises a size characterization module configured to: utilizing a trained deep learning model to calculate the dimensions and output the measured dimensions (size).

According to an embodiment, the system comprises a shape detection module configured to: Employing a trained neural network to determine geometric properties that define the shape of abnormalities; quantifying the shape characteristics.

According to an embodiment, the system comprises a prediction module for density levels of tissues configured to: process the mammogram image with a deep learning algorithm trained to evaluate tissue density; thus determine the density levels.

According to an embodiment, the system comprises a prediction module for mapping the anatomical features configured to analyze the image with a deep learning model to identify anatomical landmarks and their relation to normalities and abnormalities; rendering anatomical mapping data.

According to an embodiment, the system comprises a module for evaluating the distribution of abnormalities within breast tissue configured to apply a trained deep learning model that assesses the distribution pattern of normalities and/or abnormalities and extracting the summary of distribution data.

According to an embodiment, the system comprises a module for detecting the involvement of abnormalities with surrounding tissues configured to apply a trained deep learning model for analyzing the mammogram image to determine how abnormalities interact with or invade adjacent tissues; and outputting involvement data.

According to an embodiment, the system comprises a module for assessing the continuity of abnormalities tissues configured to apply a trained deep learning model for gaining insights in determining whether abnormalities are isolated or continuous with other tissue structures for the given mammogram image; outputting the continuity data.

According to an embodiment, the system comprises a module for determining etiologic factors of abnormalities in breast tissue configured to employ AI to analyze potential causes or contributing factors of detected abnormalities, outputting etiologic data.

According to an embodiment, the system comprises a module for characterizing abnormalities configured to utilize a deep learning model to provide a detailed profile of abnormalities, including all previously received outcomes from various modules. Outputting comprehensive characterization data as a vector representation for broad applicability. This representation is integrable for each of the assessment modules with trained AI models for generating specific assessment scores.

According to an embodiment, the system comprises a risk assessment module configured to: Estimate the likelihood of disease progression or regression based on the quantified calcification and the classified breast tissue type; Generate a risk score indicative of the patient's risk of vascular calcification based on the analysis.

According to an embodiment, the system comprises an additional data integration module configured to receive additional patient data, including genetic biomarker values, demographic data, and clinical data; Integrate the additional patient data with the outcomes of the breast image data analysis to refine the risk score.

According to an embodiment, the system comprises the processing unit configured to: Apply machine learning techniques to adapt and refine the models based on new incoming data with clinician's feedback. thereby improving the accuracy of future predictions based on the ground truth clinically evaluated.

Figure 29:
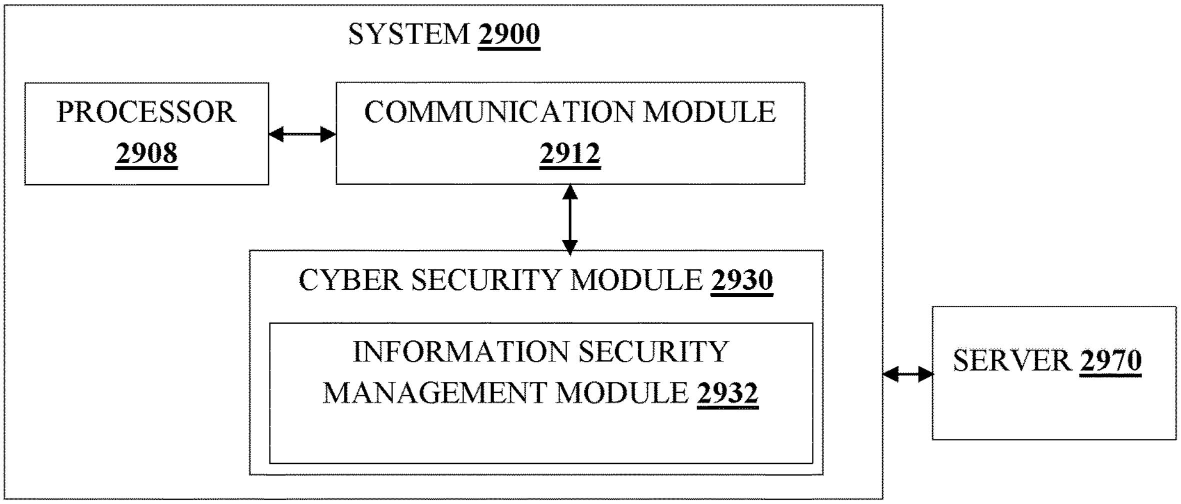
FIG. 29 shows the block diagram of the cyber security module according to an embodiment.

According to an embodiment, the data that is accessed/received via various sources and the data that is transmitted to the cloud via networks is secured using a cybersecurity module. FIG. 29 shows the block diagram of the cyber security module 2930 according to an embodiment. The communication of data between the system 2900 and the server 2970 through the communication module 2912 is first verified by the information security management module 2932 before being transmitted from the system to the server or from the server to the system. The information security management module is operable to analyze the data for potential cyber security threats, to encrypt the data when no cyber security threat is detected, and to receive or transmit the data encrypted to the system or the server.

In an embodiment, the system may comprise a cyber security module. In one aspect, a secure communication management (SCM) computer device for providing secure data connections is provided. The SCM computer device includes a processor in communication with memory. The processor is programmed to receive, from a first device, a first data message. The first data message is in a standardized data format. The processor is also programmed to analyze the first data message for potential cyber security threats. If the determination is that the first data message does not contain a cyber security threat, the processor is further programmed to convert the first data message into a first data format associated with the vehicle environment and transmit the converted first data message to the vehicle system using a first communication protocol associated with the vehicle system.

The descriptions of the one or more embodiments are for purposes of illustration but are not exhaustive or limiting to the embodiments described herein. Many modifications and variations will be apparent to those of ordinary skill in the art without departing from the scope and spirit of the described embodiments. The terminology used herein best explains the principles of the embodiments, the practical application and/or technical improvement over technologies found in the marketplace, and/or to enable others of ordinary skill in the art to understand the embodiments described herein.

Key Components of the AI Model for Breast Cancer Diagnosis are:

1) Data Preprocessing and Feature Extraction

Inputs: This stage uses mammogram images, genetic information, and various clinical and laboratory markers.

Purpose: The system first processes these images to enhance their quality and ensure a consistent format, making it easier to analyze them accurately. It then extracts essential features from the mammograms, such as the characteristics of any calcifications present (including size, density, type, location, volume, growth rate, and cluster pattern). Additionally, it standardizes clinical and laboratory data, which helps in maintaining consistency across different models.

Performance: In a recent evaluation, the feature extraction process achieved around 92% accuracy, while the consistency of data normalization was approximately 90%. These high figures highlight the reliability of the data preparation phase.

2) Calcification Vector Creation

Inputs: This component uses the extracted features from the mammograms.

Purpose: It creates a detailed vector that quantifies calcification attributes like size and density. These vectors are crucial for differentiating between various types of calcifications, which is key in the diagnostic process.

Performance: The system has demonstrated a 93% precision rate in capturing these calcification details, with a 95% completeness rate, ensuring a thorough and accurate representation.

3) Data Integration Layer

Inputs: This layer integrates the calcification vectors with genetic markers (such as BRCA1/BRCA2 status), clinical information (like age and family history), and laboratory markers (including CRP, CA15-3, CPK).

Purpose: It combines these diverse data types into a comprehensive patient profile. This integration is vital for a cohesive and accurate diagnosis, as it ensures all relevant data are considered.

Performance: The integration process has been reported to be 97% accurate, with an error rate of less than 3%, indicating strong performance in handling and merging varied datasets.

4) Machine Learning Model

Inputs: The integrated data from all previous components.

Purpose: This model is responsible for distinguishing between benign and malignant calcifications, assessing the risk of disease progression, and identifying patterns linked to specific conditions. It uses supervised learning algorithms for these classification tasks.

Performance: The model's performance metrics include classification accuracy between 88-93%, sensitivity around 87%, specificity near 90%, AUC-ROC scores ranging from 0.82 to 0.88, and precision around 85%. These results underscore the model's robustness in making accurate diagnoses.

5) Interpretation and Decision Support System

Inputs: The outputs from the machine learning model.

Purpose: This system translates the model's findings into understandable results for clinicians, providing risk assessments and recommendations. It supports clinical decision-making by pointing out significant findings and suggesting potential next steps, such as additional imaging or a biopsy.

Performance: User satisfaction with this component is over 85%, indicating that it offers valuable and actionable insights to healthcare professionals.

The AI model for diagnosing breast cancer shows strong performance across several key areas. The data preprocessing and feature extraction processes are particularly robust, with feature extraction reaching around 92% accuracy and data normalization achieving about 90% consistency. These high standards ensure the model works with quality data. In the calcification vector creation phase, the model demonstrates a 93% precision rate and 95% thoroughness in capturing detailed attributes, essential for accurate analysis.

The system's data integration layer performs exceptionally well, merging different types of data with 97% accuracy and maintaining an error rate below 3%. The machine learning component is effective in distinguishing between benign and malignant cases, with classification accuracy ranging from 88% to 93%, sensitivity around 87%, specificity near 90%, and an AUC-ROC between 0.82 and 0.88. Precision is around 85%, ensuring reliable predictions.

Lastly, the interpretation and decision support system is well-received, achieving over 85% user satisfaction. It offers valuable insights and recommendations, supporting clinicians in making informed decisions. Overall, the model excels in data processing, feature extraction, and predictive analytics, providing reliable support for accurate breast cancer diagnosis.

EXAMPLES

Example 1: BICV Cardiovascular

A 55-year-old woman came to the clinic with a palpable lump in her left breast. She has a notable family history of breast cancer, as both her mother and aunt were previously diagnosed. An AI analysis of her mammogram revealed several concerning calcifications, including a size of 4.1 mm, a density of 0.8, mixed types of calcifications, and an irregular cluster pattern, which raised suspicions of malignancy. Further lab tests showed a moderately elevated C-reactive protein (CRP) level of 6 mg/L, while her CA15-3 and CPK levels were within normal ranges. Genetic testing did not find any known mutations linked to cardiovascular risk.

For assessing cardiovascular risks, the BRICC-G system was used, considering her clinical data: blood pressure of 140/85 mmHg, heart rate of 80 bpm, a BMI of 31 indicating obesity, and a lipid profile showing LDL cholesterol at 150 mg/dL, HDL at 45 mg/dL, and triglycerides at 180 mg/dL. Additionally, elevated B-type natriuretic peptide (BNP) levels at 100 μg/mL and signs of mild diabetic retinopathy were observed. The BRICC-G score of 0.72 placed her in the high-risk category for coronary vascular events.

These findings suggest the need for further diagnostic procedures, including an ECG and stress tests. The recommended treatment plan includes lifestyle modifications, such as quitting smoking, along with medical interventions like statins and antihypertensive medications to manage her cardiovascular risk factors.

Example 2: Cardiac Contractile

A 55-year-old female, presented with a palpable lump in her left breast. The patient has a significant family history of breast cancer and cardiovascular diseases. She has a BMI of 31, indicating obesity, and has a history of hypertension and hyperlipidemia. The AI model analyzed her mammogram, identifying several calcifications with a size of 4.1 mm, density of 0.8, mixed types, and an irregular, diffuse cluster pattern, raising concerns for malignancy. Additional findings included moderately elevated CRP levels (6 mg/L) and normal levels of CA15-3 and CPK. Genetic testing revealed no known mutations.

The Cardiac Contractile Sub score assessment considered clinical data, including blood pressure at 140/85 mmHg, a heart rate of 80 bpm, mild diabetic retinopathy, and a 6-minute walk test result of 450 meters. Laboratory markers showed a hemoglobin level of 13.5 g/dL, an NLR of 3.5, an NPR of 0.2, and elevated BNPs at 100 μg/mL, among other values. The AI model indicated a high risk for cardiac contractile dysfunction, supported by mild exercise intolerance and elevated BNPs. Recommendations include further cardiac testing, lifestyle modifications, potential medical interventions, and regular monitoring to manage the identified risks effectively.

Example 3: Cardiac Rhythm

A 58-year-old woman came to the clinic reporting irregular heartbeats and fatigue. Her family history is notable for cardiovascular diseases, with both her father and grandfather having experienced heart attacks. Her medical background includes hypertension, obesity (BMI: 30), and hyperlipidemia. A recent diagnostic mammogram revealed multiple calcifications with a size of 3.9 mm, a density of 0.75, and a mixed type in an irregular cluster pattern, which is concerning for malignancy. Laboratory tests showed elevated CRP levels at 7 mg/L, with CA15-3 and CPK levels within normal limits, and no genetic mutations were detected.

The Cardiac Rhythm sub score assessment provided additional insights, noting a blood pressure reading of 145/90 mmHg and a heart rate of 95 bpr. Her laboratory markers included hemoglobin at 13.2 g/dL, a neutrophil-to-lymphocyte ratio (NLR) of 3.8, a neutrophil-to-platelet ratio (NPR) of 0.25, and elevated B-type natriuretic peptide (BNP) levels at 110 μg/mL. Her liver enzymes were normal, but her lipid profile showed slightly elevated levels, with LDL cholesterol at 155 mg/dL, HDL at 43 mg/dL, and triglycerides at 210 mg/dL.

The AI model assessed her as having a high risk of arrhythmias, based on her irregular heart rate, family history, and elevated BNP levels. It was recommended that she undergo further testing, including an electrocardiogram (ECG) and Holter monitoring, to better understand her condition.

Example 4: Renovaseular & Renal Perfusion

A 62-year-old woman, presented with leg swelling and generalized fatigue. Her family history is significant for cardiovascular diseases, particularly hypertension in her parents. Her medical history includes obesity (BMI: 29), well-managed type 2 diabetes, and a past history of smoking. A diagnostic mammogram revealed calcifications with specific attributes: a size of 3.8 mm, density of 0.72, and an irregular cluster pattern, which raised concerns about the potential for malignancy. Laboratory tests showed moderately elevated C-reactive protein (CRP) levels at 5 mg/L, while CA15-3 and CPK levels were within normal ranges, and no genetic mutations were detected.

The Renovascular & Renal Perfusion sub score assessment provided further insights, with clinical data showing a blood pressure of 150/95 mmHg, heart rate of 88 bpm, mild edema, reduced urine output, and confusion suggesting mental status changes. Skin changes, such as pallor, were also noted. Laboratory results included a hemoglobin level of 12.5 g/dL, a neutrophil-to-lymphocyte ratio (NLR) of 4.0, a neutrophil-to-platelet ratio (NPR) of 0.28, and elevated B-type natriuretic peptide (BNP) levels at 120 μg/mL. Further renal indicators showed urea at 40 mg/dL, uric acid at 6.8 mg/dL, serum creatinine at 1.2 mg/dL, normal serum potassium and sodium levels, and a 24-hour urine protein measurement of 250 mg.

The AI model indicated a high risk for renal perfusion issues, particularly concerning due to the elevated BNP levels, high blood pressure, and the protein/creatinine ratio. It was recommended that Ms. Morgan undergo a renal ultrasound and consider adjustments to her antihypertensive medications. Lifestyle modifications, including adopting a low-sodium diet and regular monitoring of renal function, were also advised to help prevent further complications.

Example 5: Retinopathy

A 60-year-old woman came in reporting blurred vision and occasional headaches. She has a strong family history of cardiovascular diseases and type 2 diabetes. Her own medical history includes hypertension, obesity (BMI: 30), and hyperlipidemia. A diagnostic mammogram detected calcifications measuring 4.2 mm with a density of 0.78, arranged in an irregular cluster pattern, which may suggest malignancy. Laboratory tests revealed an elevated C-reactive protein (CRP) level of 6 mg/L, while CA15-3 levels were normal, and no genetic mutations were identified.

The Retinopathy sub score assessment provided further insights, noting her vital signs blood pressure at 145/90 mmHg and heart rate at 82 bpm as well as mild retinopathy. Her family history also includes cardiovascular diseases. Laboratory markers showed hemoglobin at 13.0 g/dL, a neutrophil-to-lymphocyte ratio (NLR) of 3.6, a neutrophil-to-platelet ratio (NPR) of 0.22, and an elevated lipid profile with LDL cholesterol at 160 mg/dL, HDL at 42 mg/dL, and triglycerides at 200 mg/dL. Additional findings included elevated APO lipoproteins A&B, an erythrocyte sedimentation rate (ESR) of 22 mm/hr, normal CPK levels, serum creatinine at 1.1 mg/dL, and an HbA1C of 7.5%. Bilirubin levels were within normal ranges.

The AI model highlighted a high risk for progressive retinopathy, particularly due to poor glycemic control (HbA1C 7.5%) and elevated lipid levels. Recommendations for Ms. Adams include optimizing her blood sugar levels, scheduling regular eye exams to monitor her retinopathy, and considering lipid-lowering therapy to manage the risks associated with both retinopathy progression and cardiovascular complications.

Example 6: Pancreatic

A 63-year-old woman, presented with unexplained weight loss and abdominal discomfort. She has a notable family history of cardiovascular diseases and type 2 diabetes. Her medical history includes obesity (BMI: 32), hypertension, and non-alcoholic steatohepatitis (NASH). She also reported a diet high in processed foods. A diagnostic mammogram revealed calcifications measuring 3.5 mm, with a density of 0.74, and a mixed, irregular cluster pattern, raising concerns for possible malignancy. Laboratory tests showed elevated C-reactive protein (CRP) levels at 5.5 mg/L, with normal CA15-3 levels, and no detectable genetic mutations.

The Pancreatic sub score assessment provided further details, including her vital signs—blood pressure at 148/92 mmHg and heart rate at 78 bpm—and physical examination findings of mild tenderness in the upper abdomen. Laboratory results included hemoglobin at 13.7 g/dL, a neutrophil-to-lymphocyte ratio (NLR) of 4.1, a neutrophil-to-platelet ratio (NPR) of 0.25, and an elevated lipid profile with LDL cholesterol at 170 mg/dL, HDL at 40 mg/dL, and triglycerides at 220 mg/dL. Additionally, levels of APO lipoproteins A&B were elevated, as were her erythrocyte sedimentation rate (ESR) at 25 mm/hr. Notably, pancreatic enzymes were also elevated, with amylase at 120 U/L and lipase at 140 U/L. Her serum creatinine was normal at 1.0 mg/dL, the ALT/AST ratio was slightly elevated at 1.2, and bilirubin levels were within normal limits.

The AI model suggested a high risk for pancreatic issues, particularly given the elevated pancreatic enzymes and abnormal lipid profile. Recommendations include conducting further imaging studies, such as a CT scan or MRI, to better assess potential pancreatic pathology. Additionally, dietary modifications to reduce fat intake and regular monitoring of blood glucose and pancreatic enzymes were advised to manage the risks of pancreatitis and other associated complications.

Example 7: Cerebrovascular & CNS

A 59-year-old woman, reported experiencing episodes of dizziness and mild memory loss. Her family has a significant history of cardiovascular diseases, and she herself has a history of hypertension and previous transient ischemic attacks (TIAs). Ms. Thompson is classified as overweight with a BMI of 28 and has mild retinopathy. There is no history of seizures or stroke, A recent diagnostic mammogram revealed calcifications with a size of 3.7 mm, density of 0.76, and an irregular cluster pattern, necessitating further evaluation for possible malignancy. Laboratory tests showed an elevated C-reactive protein (CRP) level of 5 mg/L, with CA15-3 and CPK levels within normal limits, and no genetic mutations were detected.

For the Cerebrovascular & CNS sub score assessment, clinical data included vitals showing a blood pressure of 150/90 mmHg and a heart rate of 84 bpm. Laboratory markers revealed hemoglobin at 13.2 g/dL, a neutrophil-to-lymphocyte ratio (NLR) of 3.5, a neutrophil-to-platelet ratio (NPR) of 0.23, an elevated lipid profile with LDL cholesterol at 165 mg/dL, HDL at 45 mg/dL, and triglycerides at 195 mg/dL. Elevated APO lipoproteins A&B were noted, along with an erythrocyte sedimentation rate (ESR) of 18 mm/hr. Her serum creatinine was normal at 1.0 mg/dL, though there was a slight imbalance in serum potassium and sodium levels. B-type natriuretic peptide (BNP) levels were mildly elevated at 95 μg/mL, and troponin levels were normal.

The AI model indicated an increased risk for cerebrovascular events, supported by Ms. Thompson's history of TIAs, elevated lipid profile, and hypertension. Recommendations include undergoing a brain MRI to check for any ischemic changes, maintaining strict control over blood pressure and lipid levels, considering antiplatelet therapy, and making lifestyle changes to reduce cerebrovascular risks. Regular follow-up and monitoring are crucial for managing these identified risks.

Example 8: Pulmonary/COPD

A 65-year-old male patient, presented with a chronic cough and shortness of breath. He has a significant history of smoking, amounting to 40 pack-years, and occasionally experiences wheezing. Although his family history includes cardiovascular diseases, there is no known history of chronic obstructive pulmonary disease (COPD) or asthma. Mr. Roberts is slightly overweight, with a BMI of 27, and has a history of controlled hypertension. A diagnostic mammogram revealed calcifications measuring 4.0 mm with a density of 0.80 and a mixed type, which warrants further investigation. Laboratory results showed an elevated C-reactive protein (CRP) level of 7 mg/L, normal CA15-3 levels, and no significant genetic mutations.

The Pulmonary/COPD sub score assessment provided additional details, including vitals with a blood pressure of 140/88 mmHg and a heart rate of 80 bpm. Laboratory markers revealed a hemoglobin level of 13.8 g/dL, a neutrophil-to-lymphocyte ratio (NLR) of 4.2, a neutrophil-to-platelet ratio (NPR) of 0.20, and an elevated lipid profile with LDL cholesterol at 160 mg/dL, HDL at 42 mg/dL, and triglycerides at 190 mg/dL. Additionally, elevated APO lipoproteins A&B and an erythrocyte sedimentation rate (ESR) of 20 mm/hr were noted. His serum creatinine was normal at 1.1 mg/dL, as were his ALT/AST ratio and CPK levels. The B-type natriuretic peptide (BNP) level was slightly elevated at 105 μg/mL. Genetic screening found no high-risk mutations among the genes tested, including APOL and LPA.

The AI model indicated a high risk for COPD, supported by Mr. Roberts's smoking history, chronic respiratory symptoms, and elevated inflammatory markers. The recommendations include performing a pulmonary function test (PFT) to assess lung capacity, advising smoking cessation, and considering pharmacotherapy to manage COPD symptoms and prevent disease progression. Regular monitoring of both respiratory and cardiovascular markers is crucial for managing patient's overall health.

Example 9: Chronic Disease

A 60-year-old woman came in with persistent fatigue and joint pain. She has a family history of cardiovascular diseases and type 2 diabetes, and her own medical history includes hypertension and obesity (BMI: 29). She also has mild retinopathy. A diagnostic mammogram detected calcifications measuring 4.1 mm, with a density of 0.78 and a mixed, irregular cluster pattern, raising concerns about potential malignancy. Laboratory tests revealed an elevated C-reactive protein (CRP) level of 6 mg/L, with normal CA15-3 levels, and no significant genetic mutations were identified.

For the Chronic Disease sub score, clinical data showed a blood pressure of 145/92 mmHg and a heart rate of 82 bpm. Additional laboratory markers included a hemoglobin level of 12.9 g/dL, a neutrophil-to-lymphocyte ratio (NLR) of 3.8, a neutrophil-to-platelet ratio (NPR) of 0.22, and an elevated lipid profile with LDL cholesterol at 165 mg/dL, HDL at 44 mg/dL, and triglycerides at 195 mg/dL. APO lipoproteins A&B levels were noted, and the erythrocyte sedimentation rate (ESR) was 25 mm/hr. Creatine phosphokinase (CPK) was within normal limits at 110 U/L, while serum creatinine was 1.0 mg/dL. The ALT/AST ratio was slightly elevated at 1.3, and troponin levels were normal. B-type natriuretic peptide (BNP) levels were slightly elevated at 105 pg/mL. Genetic screening identified high-risk mutations in genes such as APOE, LPA, and PCSK9.

The AI model suggested a high risk for the development of chronic diseases, supported by elevated inflammatory markers, lipid abnormalities, and her family history. The recommendations include managing inflammation and lipid levels, monitoring for potential diabetes onset, and scheduling regular follow-ups to assess and manage the progression of any chronic conditions.

Example 10: Critical Vascular Perfusion 60-year-old women came in with complaints of leg pain and intermittent claudication. Her medical history includes a previous myocardial infarction (CAD), controlled hypertension, and obesity, with a BMI of 30. She also has a significant family history of cardiovascular diseases and displays mild retinopathy. A diagnostic mammogram showed calcifications measuring 4.0 mm in size, with a density of 0.76 and a mixed, irregular cluster pattern, raising concerns about potential malignancy. Laboratory tests revealed an elevated C-reactive protein (CRP) level of 5.5 mg/L, normal CA15-3 levels, and no significant genetic mutations.

The Critical Vascular Perfusion sub score assessment highlighted several key clinical data points: blood pressure was 150/95 mmHg, and heart rate was 85 bpm. Laboratory results showed hemoglobin at 13.0 g/dL, a neutrophil-to-lymphocyte ratio (NLR) of 4.0, a neutrophil-to-platelet ratio (NPR) of 0.24, and an elevated lipid profile with LDL cholesterol at 170 mg/dL, HDL at 43 mg/dL, and triglycerides at 210 mg/dL. Elevated levels of APO lipoproteins A&B were noted, as well as an erythrocyte sedimentation rate (ESR) of 22 mm/hr. Creatine phosphokinase (CPK) was 115 U/IL, serum creatinine was 1.1 mg/dL, and the ALT/AST ratio was 1,1. Potassium and sodium levels were within normal ranges, troponin levels were normal, and B-type natriuretic peptide (BNP) levels were slightly elevated at 110 pg/mL. Genetic testing did not reveal significant mutations in genes such as APOE, LPA, and PCSK9.

The AI model indicated a high risk for critical vascular perfusion issues, which is supported by here history of coronary artery disease, elevated BNP levels, and inflammatory markers. The recommendations include conducting vascular imaging studies, such as a Doppler ultrasound, to assess blood flow, aggressively managing lipid levels and blood pressure, and making lifestyle changes to improve vascular health. Regular monitoring and the possibility of surgical consultation for vascular interventions were also advised.

Example 11: Healing

A 55-year-old woman, came to the clinic worried about slow healing following recent surgery. She has a family history of cardiovascular diseases and has previously been treated for breast cancer with chemotherapy and radiation therapy. Her medical history includes hypertension and obesity (BMI: 32), along with signs of mild retinopathy. A diagnostic mammogram revealed calcifications measuring 3.6 mm in size, with a density of 0.74 and an irregular cluster pattern, raising concerns about potential malignancy. Laboratory tests showed an elevated CA15.3 level at 45 U/mL, while CA125 and CEA levels were normal, and no significant genetic mutations were detected.

For the Healing Subscore assessment, clinical data included blood pressure at 145/90 mmHg and a heart rate of 82 bpm. Additional laboratory markers showed CEA at 4.2 ng/mL (normal), CA19.9 at 35 U/mL (normal), and PSA at 0.5 ng/mL (normal for females). Estradiol levels were within normal limits. A complete blood count (CBC) indicated mild anemia, with hemoglobin at 11.8 g/dL. Both renal function tests (RFT) and liver function tests (LFT) were normal, while thyroid function tests (TFT) suggested mild hypothyroidism. The lipid profile revealed elevated LDL cholesterol at 150 mg/dL, with HDL cholesterol at 50 mg/dL. Genetic testing showed no high-risk mutations in BRCA1 & 2, PTEN, or other relevant genes.

The AI model indicated a moderate risk for impaired healing, which is likely exacerbated by patient's previous cancer treatments, anemia, and mild hypothyroidism. The recommendations include optimizing her thyroid function and addressing anemia, along with closely monitoring her wound healing progress. It was also advised that she seek additional support from wound care specialists and consider nutritional support to aid in recovery.

Example 12: Tumor Flow and Growth

A 52-year-old woman reported experiencing recurrent abdominal pain and noticed a palpable lump in her left breast. She has a significant family history of cardiovascular diseases and has previously undergone surgery and chemotherapy for breast cancer. Her BMI is 28, and she has mild retinopathy. A recent diagnostic mammogram revealed calcifications measuring 4.2 mm with a density of 0.80, arranged in an irregular cluster pattern, raising concerns about possible tumor recurrence. Laboratory tests showed an elevated CA15.3 level at 50 U/mL, while CEA, CA19.9, and CA125 levels were within normal ranges. Genetic testing found high-risk mutations in markers such as BRCA1 & 2, PTEN, or TP53.

For the Tumor Flow and Growth Subscore assessment, her vital signs included a blood pressure of 140/85 mmHg and a heart rate of 78 bpm. The laboratory profile included normal PSA levels, estradiol within normal ranges, a complete blood count (CBC) indicating mild anemia with a hemoglobin level of 11.5 g/dL, and normal results for renal and liver function tests (RFT and LFT). The lipid profile showed slightly elevated LDL cholesterol at 160 mg/dL. Thyroid function tests (TFT) were normal.

The AI model assessed a high risk for tumor recurrence and progression, supported by the elevated CA15.3 levels and patient's history of breast cancer. The recommendations include conducting advanced imaging studies, such as a PET-CT scan, to check for potential metastasis, considering a biopsy for any new lesions, and closely monitoring tumor markers. Regular follow-ups with her oncologist and possible adjustments in treatment strategies are crucial to managing the risk of recurrence and progression.

Example 13: Relapse

A 58-year-old woman, came in with concerns about recurring fatigue and a new palpable mass in her right breast. She has a family history of cardiovascular diseases and has previously been treated for breast cancer with a lumpectomy and radiation therapy. Her BMI is 27, and she has mild retinopathy. A recent diagnostic mammogram revealed calcifications measuring 3.9 mm, with a density of 0.82 and an irregular cluster pattern, raising concerns about possible cancer recurrence. Laboratory tests showed an elevated CA15.3 level at 55 U/mL, while CEA, CA19.9, and CA 125 levels were normal. Genetic testing did not detect mutations in BRCA1 & 2, PTEN, or other relevant markers.

The Relapse Subscore assessment included vital signs such as a blood pressure of 135/80 mmHg and a heart rate of 76 bpm, along with the patient's cancer treatment history. The laboratory profile revealed mild anemia with a hemoglobin level of 12.0 g/dL, normal renal and liver function tests, and normal thyroid function. The lipid profile showed elevated LDL cholesterol at 155 mg/dL.

The AI model indicated a high risk of cancer relapse, supported by the elevated CA15.3 levels and the mammogram findings. The recommendations include further diagnostic imaging, such as MRI or PET-CT scans, to assess the extent of potential recurrence, as well as a biopsy of the new mass. Close monitoring of tumor markers, regular oncological follow-ups, and potential adjustments to the treatment regimen are crucial for managing the risk of recurrence and ensuring timely intervention.

Example 14: Adverse Events

A 61-year-old man, presented with recent symptoms of fatigue and slight jaundice. He has a family history of cardiovascular diseases and has previously been treated for colorectal cancer with chemotherapy. His BMI is 29, and he shows signs of mild retinopathy and has been experiencing joint pains. A recent diagnostic evaluation, including imaging, identified calcifications measuring 3.8 mm with a density of 0.80 and an irregular pattern. Laboratory tests revealed elevated CA19.9 at 40 U/mL, while CEA, CA15.3, CA125, and PSA levels were normal. Genetic testing did not detect significant mutations in BRCA1 & 2, PTEN, or other relevant genes.

The Adverse Events Subscore assessment included clinical data such as a blood pressure of 140/85 mmHg and a heart rate of 80 bpm, along with patient's history of cancer treatments. Laboratory results showed mild anemia with a hemoglobin level of 12.5 g/dL, normal renal function tests (RFT), but elevated liver enzymes on liver function tests (LFT). His lipid profile indicated increased LDL cholesterol at 160 mg/dL, while thyroid function tests (TFT) were within normal limits.

The AI model highlighted a high risk of adverse events, including potential hepatotoxicity, due to the elevated liver enzymes and CA19.9 levels. The recommendations include comprehensive liver imaging, possibly an MRI, to assess liver health, close monitoring of liver function, and adjustments to any medications that may be contributing to liver strain. Ongoing follow-ups are essential to manage and mitigate the risk of further adverse events, considering cancer history and overall health status.

Example 15: Clinical Response

A 57-year-old woman expressed concerns about her response to her current breast cancer treatment. She has a significant family history of cardiovascular diseases and a history of hypertension. With a BMI of 28, she also has mild retinopathy and has previously undergone surgery and chemotherapy for breast cancer. A recent diagnostic mammogram revealed calcifications measuring 3.7 mm, with a density of 0.78 and a mixed, irregular cluster pattern. Laboratory tests showed an elevated CA15.3 level at 52 U/mL, while CEA, CA19.9, CA125, and PSA levels were normal. Genetic testing did not detect mutations in BRCA1 & 2, PTEN, or other associated genes.

For the Clinical Response Subscore assessment, her clinical data included vital signs such as blood pressure at 135/85 mmHg and a heart rate of 75 bpm, as well as her cancer treatment history. Laboratory markers showed a complete blood count (CBC) indicating mild anemia with a hemoglobin level of 12.8 g/dL, normal renal and liver function tests (RFT and LFT), and normal thyroid function tests (TFT). The lipid profile indicated elevated LDL cholesterol at 150 mg/dL.

The AI model suggested that Ms. Lee's clinical response to her treatment was not optimal, as evidenced by elevated tumor markers (CA15.3) and ongoing symptoms. Recommendations include considering adjustments to her therapeutic regimen, possibly incorporating targeted therapies, and closely monitoring tumor markers. Further imaging studies, such as a PET-CT scan, may be necessary to assess disease progression and refine the treatment plan. Regular follow-ups and comprehensive management are crucial to optimizing clinical outcomes.

Example 16

A 50-year-old female with a BMI of 28 kg/m$^2$, presents with a 10 mm low-density microcalcification in the central region of the left breast. The calcification volume is 40 mm$^3$ with a growth rate of 10% over six months, and it appears in a clustered pattern. Laboratory results show CRP levels at 3 mg/L, CA15-3 at 20 U/mL, and Cpk at 120 U/L. Notably, the patient is BRCA1 negative and has no family history of breast cancer. These inputs have been analyzed to predict risk scores for a variety of potential health concerns.

The risk scores reveal significant insights into the patient's health profile. Cardiovascular and cerebrovascular risks are notably high, with scores of 85 and 82 respectively, indicating a strong correlation with breast arterial calcifications, inflammation, and age. Other risks such as contractile (60), rhythm (55), renovascular (58), and inflammation (68) display moderate correlations, reflecting a complex interplay of cardiovascular risks, BMI, and inflammation markers. Lower scores are observed for retinopathy (40), pancreatic (38), tumor growth (35), and relapse (30), suggesting a less pronounced risk in these areas. The overall sensitivity analysis underscores the critical need to prioritize cardiovascular and cerebrovascular interventions, while other risks should be monitored as part of a holistic health management plan.

Example 17

A 55-year-old female patient with a BMI of 30 kg/m$^2$, presenting with a 5 mm medium-density macrocalcification located in the lower inner quadrant of the right breast. The calcification has a volume of 30 mm$^3$ and a growth rate of 5% over 12 months, appearing in a scattered pattern. Laboratory results indicate CRP levels at 2 mg/L, CA15-3 at 25 U/mL, and Cpk at 100 U/L. The patient is BRCA2 negative and has no family history of breast cancer. These parameters are analyzed to predict risk scores for various health conditions.

The risk scores provide significant insights into the patient's health profile. Cardiovascular risk is high with a score of 80, reflecting a strong correlation with breast arterial calcifications and medium CRP levels. Other high-risk scores include contractile (75), rhythm (70), renovascular (72), cerebrovascular (78), chronic disease (85), vascular perfusion (82), inflammation (88), adverse events (82), and clinical response (83). These scores indicate strong correlations with cardiovascular risks, BMI, and systemic inflammation. Moderate risk scores are observed for retinopathy (55), pancreatic (50), COPD (52), and healing (60), reflecting moderate correlations with inflammation and BMI. The lowest scores are seen in tumor growth (35) and relapse (38), suggesting less pronounced risks in these areas. This stratification assists in understanding the patient's health risks and prioritizing medical interventions based on their specific health profile and existing medical knowledge.

Example 18

A 45-year-old female patient with a BMI of 25 kg/m$^2$, presents with an 8 mm high-density microcalcification in the upper outer quadrant of the left breast. The calcification has a volume of 50 mm$^3$ and a growth rate of 15% over six months, appearing in a clustered pattern. Laboratory results show CRP levels at 5 mg/L, CA15-3 at 30 U/mL, and Cpk at 150 U/L. The patient is BRCA1 positive and has a family history of breast cancer. These inputs were analyzed to predict risk scores for various health conditions, based on their correlation levels.

The risk scores provide critical insights into the patient's health profile. High correlation scores indicate significant risks for cardiovascular (85), contractile (80), rhythm (75), renovascular (78), cerebrovascular (82), chronic disease (88), vascular perfusion (84), inflammation (90), adverse events (85), and clinical response (87). These scores reflect strong correlations with factors such as breast arterial calcifications, genetic predispositions, inflammation, and comprehensive health profiles. Moderate risk scores include retinopathy (60), pancreatic (55), COPD (50), and healing (65), highlighting moderate correlations with systemic conditions like inflammation and BMI. Lower scores in tumor growth (30) and relapse (40) suggest less pronounced risks in these areas.

INCORPORATION BY REFERENCE

All references, including granted patents and patent application publications, referred herein are incorporated herein by reference in their entirety.

U.S. patent Ser. No. 11/246,550B2, titled, "Method for detection and quantification of arterial calcification"

US Patent Application Publication, US20200005901A1, titled, "Cancer classifier models, machine learning systems and methods of use"

US Patent Application Publication, US20200335179A1, titled, "Clinical decision model"

Chen, D. H., Tyebally, S., Malloupas, M. et al. Cardiovascular Disease Amongst Women Treated for Breast Cancer: Traditional Cytotoxic Chemotherapy, Targeted Therapy, and Radiation Therapy. Curr Cardiol Rep 23, 16 (2021). https://doi.org/10.1007/s11886-021-01446x

PRIOR PUBLICATIONS BY THE INVENTORS

Suresh, A. V. S., Sharma, R., Dadireddy, P. K., Bunga, R., Lalukota, K. M., Reddy, P. K., & Reddy, G. N. (2022). Vascular calcifications in mammogram and correlate them with coronary artery diseases: a retrospective study. *International Journal of Community Medicine and Public Health/International Journal of Community Medicine and Public Health,* 9(7), 2961. https://doi.org/10.18203/2394-6040.ijcmph20221766

Kistampally, P., & Attili, S. (2022). 419P Breast arterial calcifications on mammogram and its clinical implications. *Annals of Oncology,* 33, S1605. https://doi.org/10.1016/j.annonc.2022.10.450

Dusi, V. S., Attili, S. V., Vutukuru, A., Peri, S. V., & Sharma, R. (2023). Correlation of breast arterial calcification with overall survival in patients with breast cancer. *Journal of Clinical Oncology,* 41(16_suppl), e12501. https://doi.org/10.1200/jco.2023.41.16_suppl.e12501

OTHER REFERENCED PUBLICATIONS

Fatima, G., Allami, R H., & Yousif, M G. (2023, January 1). Integrative AI-Driven Strategies for Advancing Precision Medicine in Infectious Diseases and Beyond: A Novel Multidisciplinary Approach. Cornell University. https://doi.org/10.48550/arxiv. 2307. 15228

Harris, K M. (2010, February 1). An integrative approach to health. Springer Science+Business Media, 47(1), 1-22. https://doi.org/10.1353/dem. 0.0091

Williams, V J. (2010, March 17). An Analysis of Health Care Assessments Used for Sustaining Communities. Canadian Center of Science and Education, 2(1). https://doi.org/10.5539/gjhs.v2n1p89

McClintock, M K., Dale, W., Laumann, E O., & Waite, L J. (2016, May 16). Empirical redefinition of comprehensive health and well-being in the older adults of the United States. National Academy of Sciences, 113(22). https://doi.org/10.1073/pnas. 1514968113

Fuellen, G., Jansen, L., Cohen, A A., Luyten, W., Gogol, M., Simm, A., Saul, N., Cirulli, F., Berry, A., Antal, P., Köhling, R., Wouters, B H., & Möller, S. (2019, January 1). Health and Aging: Unifying Concepts, Scores, Biomarkers and Pathways. Buck Institute for Research on Aging, 10(4), 883-883. https://doi.org/10.14336/ad.2018.1030

What is claimed is:

1. A system comprising:

a processor executing one or more machine learning models;

wherein the processor storing instructions in a non-transitory memory that, when executed, cause the processor to:

receive a first input comprising an image of a breast of a patient;

receive a second input comprising a patient data, wherein the patient data comprises a first genetic data of the patient;

extract features from the image and the patient data, using the machine learning models, wherein the features comprise a presence of a calcification and a calcification pattern to generate a breast calcification vector;

augment the breast calcification vector with the first genetic data to generate a feature vector;

determine, using the machine learning models, a first output comprising a first risk for a breast cancer;

determine, using the machine learning models, a second output comprising a second risk to one or more organs of the patient, wherein the organs comprises one or more of heart, kidney, lungs, pancreas, and brain;

predict, using the machine learning models, a third output comprising a third risk based on one or more of a healing response, a tumor flow and growth, inflammation and degeneration, a disease relapse, an adverse event, and a clinical response of the patient; and determine, using a statistical model, a fourth output comprising an overall risk to the patient based on the first risk, the second risk, and the third risk;

wherein the machine learning models are pre-trained, wherein pre-training comprises training the machine learning models using training data from plurality of patients, wherein the training data corresponding to each patient from the plurality of patients comprises one or more of breast images, chest images, organ images, second genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

2. The system of claim 1, wherein the image comprises one or more of mammogram image, ultrasound image, computed tomography image, and magnetic resonance image.

3. The system of claim 1, wherein the system comprises a feature extraction module comprising a deep learning model for image analysis and for extracting of the features from the image.

4. The system of claim 1, wherein the system comprises a preprocessing module configured to normalize quality of the image across different imaging modalities.

5. The system of claim 1, wherein the features comprises one or more of a ratio of fat to fiber, connective tissue density, and echogenicity of lumps.

6. The system of claim 1, wherein the fourth output is a quantified score as BRICC-G score.

7. The system of claim 1, wherein the presence of the calcification is identified via a calcification detection module; and wherein the calcification detection module is further configured to identify and classify a type of calcification as one of ductile, vascular, and parenchymal calcification.

8. The system of claim 1, wherein the calcification pattern comprises one of more modules comprising deep learning models to determine one or more of a location, a spread, a nature, a size, a shape, a density, an anatomy, a distribution, an involvement, a continuity, an etiologic, and a characterization of breast arterial calcifications.

9. The system of claim 8, wherein the system further comprises a spread detection module configured to detect the spread of abnormalities within the image and determine a quantifying measure by generating a spread index representing an extent of each abnormality of the abnormalities.

10. The system of claim 8, wherein the system further comprises a malignant detection module configured to detect the nature of the calcification pattern, wherein the nature is one of a benign and a malignant; and wherein the nature of the calcification pattern is detected based on the features extracted from textural and morphological data; and wherein the nature of the calcification pattern is classified as one of normality and abnormality.

11. The system of claim 8, wherein the system further comprises a size characterization module and a shape detection module, wherein the size characterization module is configured to calculate the size comprising a dimension and output the dimension of the calcification; and wherein the shape detection module configured to determine geometric properties that define the shape of abnormalities; and quantify characteristics of the shape of the calcification.

12. The system of claim 8, wherein the system further comprises a tissue density prediction module and an anatomy prediction module, wherein the tissue density prediction module is configured for detecting density levels of tissue and determine the density by processing the image to evaluate the density of a tissue and determine levels of the density, and wherein the anatomy prediction module is configured for mapping anatomical features, identifying anatomical landmarks and relation of the anatomical features and the anatomical landmarks as normalities and abnormalities to determine mapping data of the anatomy.

13. The system of claim 8, wherein the system further comprises a characterizing module and an abnormality distribution assessment module, wherein the characterizing module is configured for characterization of abnormalities to provide a profile of the abnormalities and output characterization data; and the abnormality distribution assessment module is configured for evaluating the distribution of the abnormalities within a tissue of the breast and extracting a summary of the distribution.

14. The system of claim 8, wherein the system further comprises an involvement assessment module for detecting the involvement of abnormalities with surrounding tissues for analyzing the image to determine abnormalities interacting or invading adjacent tissues and output involvement data.

15. The system of claim 8, wherein the system further comprises a continuity assessment module and an etiologic module, wherein the continuity assessment module is configured for assessing the continuity of abnormalities in tissues for determining abnormalities as isolated or continuous with other tissue structures for the image; and output continuity data; and the etiologic module is configured for determining etiologic factors of abnormalities in the image to determine potential causes or contributing factors of the abnormalities; and output etiologic data.

16. The system of claim 1, wherein the first genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A, BRCA 1, BRCA 2, PTEN, PALB 2, TP53, ATM, RB, CDH1, CHDI2, CHECK2, NF1NBN, STK11, MSI, BARD, BRIPRAD, POLE, TNF, IL6&1beta, MMP3, COL2A1, APOE, PSEN1SNAK, PARKIN, HLA, NOD2.

17. The system of claim 1, wherein the second risk comprises one or more of cardiovascular risk, cardiac contractile risk, cardiac rhythm risk, renovascular and renal perfusion risk, retinopathy risk, pancreatic risk, cerebrovascular and CNS health risk, pulmonary risk, chronic disease risk, vascular perfusion risk.

18. A method comprising:

receiving a first input comprising an image of a breast of a patient;

receiving a second input comprising a patient data, wherein the patient data comprises a first genetic data of the patient;

extracting features from the image and the patient data, using one or more machine learning models, wherein the features comprise a presence of a calcification and a calcification pattern to generate a breast calcification vector;

augmenting the breast calcification vector with the first genetic data to generate a feature vector;

determining, using the machine learning models, a first output comprising a first risk for a breast cancer;

determining, using the machine learning models, a second output comprising a second risk to one or more organs of the patient, wherein the organs comprises one or more of a heart, a kidney, lungs, a pancreas, and a brain of the patient;

predicting, using the machine learning models, a third output comprising a third risk based on one or more of a healing response, a tumor flow and growth, inflammation and degeneration, a disease relapse, an adverse event, and a clinical response of the patient; and determining, using a statistical model, a fourth output comprising an overall risk to the patient based on the first risk, the second risk, and the third risk;

wherein the machine learning models are pre-trained, wherein pre-training comprises training the machine learning models using training data from plurality of patients, wherein the training data corresponding to each patient from the plurality of patients comprises one or more of breast images, chest images, organ images, second genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

19. The method of claim 18, wherein the calcification pattern comprises one of more modules comprising deep learning models to determine one or more of a location, a spread, a nature, a size, a shape, a density, an anatomy, a distribution, an involvement, a continuity, an etiologic, and a characterization of breast arterial calcifications; and wherein the first genetic data comprises one or more of APOE, LPA, LDLR, PCSK9, TNF-alpha, VDR, TCF7L2, KCNJ11, PPARG, CAPN10, ACE, AGT, AGTR1, NOS3, CYP11B2, APOB, CETP, LIPC, APOA5, HMGCR, IL6, MMP9, CDKN2A, AGER, SPP1, COL1A1, MGP, OPN, SLC20A, BRCA 1, BRCA 2, PTEN, PALB 2, TP53, ATM, RB, CDH1, CHDI2, CHECK2, NF1NBN, STK11, MSI, BARD, BRIPRAD, POLE, TNF, IL6&1beta, MMP3, COL2A1, APOE, PSEN1SNAK, PARKIN, HLA, NOD2.

20. A non-transitory computer-readable medium having stored thereon instructions executable by a computer system to perform operations comprising:

receiving a first input comprising an image of a breast of a patient;

receiving a second input comprising a patient data, wherein the patient data comprises a first genetic data of the patient;

extracting features from the image and the patient data, using one or more machine learning models, wherein the features comprise a presence of a calcification and a calcification pattern to generate a breast calcification vector;

augmenting the breast calcification vector with the first genetic data to generate a feature vector;

determining, using the machine learning models, a first output comprising a first risk for a breast cancer;

determining, using the machine learning models, a second output comprising a second risk to one or more organs of the patient, wherein the organs comprises one or more of a heart, a kidney, lungs, a pancreas, and a brain of the patient;

predicting, using the machine learning models, a third output comprising a third risk based on one or more of a healing response, a tumor flow and growth, inflammation and degeneration, a disease relapse, an adverse event, and a clinical response of the patient; and determining, using a statistical model, a fourth output comprising an overall risk to the patient based on the first risk, the second risk, and the third risk;

wherein the machine learning models are pre-trained, wherein pre-training comprises training the machine learning models using training data from plurality of patients, wherein the training data corresponding to each patient from the plurality of patients comprises one or more of breast images, chest images, organ images, second genetic data, demographic data, social determinants of health, clinical data, and clinicians' notes; and wherein the machine learning models comprise a feedback loop to consider one or more of the first input, the second input, and a clinicians' input and improve one or more of the first output, the second output, the third output, and the fourth output in real-time.

* * * * *